(12) United States Patent
Bradbury et al.

(10) Patent No.: US 12,082,907 B2
(45) Date of Patent: Sep. 10, 2024

(54) SYSTEMS, METHODS, AND APPARATUS FOR MULTICHANNEL IMAGING OF FLUORESCENT SOURCES IN REAL-TIME

(71) Applicants: Memorial Sloan Kettering Cancer Center, New York, NY (US); Cornell University, Ithaca, NY (US); Quest Medical Imaging B.V., Middenmeer (NL)

(72) Inventors: Michelle S. Bradbury, New York, NY (US); Ulrich Wiesner, Ithaca, NY (US); Richard J. C. Meester, Middenmeer (NL); Snehal G. Patel, New York, NY (US); Nadeem R. Abu-Rustum, Tenafly, NJ (US); Mohan Pauliah, New York, NY (US)

(73) Assignees: Memorial Sloan Kettering Cancer Center, New York, NY (US); Cornell University, Ithaca, NY (US); Quest Medical Imaging B.V., Middenmeer (NL)

( * ) Notice: Subject to any disclaimer, the term of this patent is extended or adjusted under 35 U.S.C. 154(b) by 991 days.

(21) Appl. No.: 16/787,112

(22) Filed: Feb. 11, 2020

(65) Prior Publication Data
US 2020/0214571 A1 Jul. 9, 2020

Related U.S. Application Data

(62) Division of application No. 14/588,066, filed on Dec. 31, 2014, now Pat. No. 10,986,997.
(Continued)

(51) Int. Cl.
*A61B 5/00* (2006.01)
*A61B 1/00* (2006.01)
(Continued)

(52) U.S. Cl.
CPC ........ *A61B 5/0071* (2013.01); *A61B 1/00006* (2013.01); *A61B 1/000094* (2022.02);
(Continued)

(58) Field of Classification Search
CPC ........... A61B 5/00; A61B 5/0071; A61B 6/00; A61B 6/56; C12Q 1/00
See application file for complete search history.

(56) References Cited

U.S. PATENT DOCUMENTS

| 5,776,427 A | 7/1998 | Thorpe et al. |
| 6,254,852 B1 | 7/2001 | Glajch et al. |

(Continued)

FOREIGN PATENT DOCUMENTS

| JP | 2012-050511 A | 3/2012 |
| JP | 2012-050633 A | 3/2012 |

(Continued)

OTHER PUBLICATIONS

_Image guided oncologic surgery using invisible light; Tanaka; 2006. (Year: 2006).*

(Continued)

*Primary Examiner* — Luis Perez-Fuentes
(74) *Attorney, Agent, or Firm* — Choate, Hall & Stewart LLP; William R. Haulbrook; Margo R. Monroe

(57) ABSTRACT

Presented herein is a multichannel imaging system capable of detecting and distinguishing multiple fluorescent light sources simultaneously. Also described herein are methods of using the system to image disease or cellular abnormalities, e.g., for diagnostic and/or intraoperative purposes.

21 Claims, 49 Drawing Sheets

Related U.S. Application Data

(60) Provisional application No. 61/987,426, filed on May 1, 2014, provisional application No. 61/922,619, filed on Dec. 31, 2013.

(51) Int. Cl.
*A61B 1/04* (2006.01)
*A61B 1/045* (2006.01)
*A61B 1/05* (2006.01)
*A61B 1/06* (2006.01)
*A61B 1/07* (2006.01)
*A61B 1/313* (2006.01)
*A61B 6/03* (2006.01)

(52) U.S. Cl.
CPC .............. *A61B 1/000095* (2022.02); *A61B 1/000096* (2022.02); *A61B 1/0005* (2013.01); *A61B 1/00096* (2013.01); *A61B 1/00105* (2013.01); *A61B 1/00186* (2013.01); *A61B 1/00188* (2013.01); *A61B 1/042* (2013.01); *A61B 1/043* (2013.01); *A61B 1/045* (2013.01); *A61B 1/051* (2013.01); *A61B 1/0646* (2013.01); *A61B 1/0669* (2013.01); *A61B 1/07* (2013.01); *A61B 1/3132* (2013.01); *A61B 5/0084* (2013.01); *A61B 5/742* (2013.01); *A61B 6/037* (2013.01)

(56) References Cited

U.S. PATENT DOCUMENTS

| | | |
|---|---|---|
| 6,293,911 B1 | 9/2001 | Imaizumi et al. |
| 6,545,264 B1 | 4/2003 | Stern |
| 6,593,558 B1 | 7/2003 | Edgar |
| 7,601,355 B2 | 10/2009 | Howard et al. |
| 7,787,121 B2 | 8/2010 | Tsujita et al. |
| 8,062,215 B2 | 11/2011 | Voegele et al. |
| 8,239,007 B2 | 8/2012 | Voegele et al. |
| 8,298,677 B2 | 10/2012 | Wiesner et al. |
| 8,389,679 B2 | 3/2013 | Eckert et al. |
| 8,409,876 B2 | 4/2013 | Wiesner et al. |
| 10,394,008 B2* | 8/2019 | Bares ................ G01J 3/0208 |
| 10,986,997 B2* | 4/2021 | Bradbury ......... A61B 1/000096 |
| 2003/0044353 A1* | 3/2003 | Weissleder .......... C12Q 1/6816 424/178.1 |
| 2003/0219785 A1 | 11/2003 | Hallahan et al. |
| 2004/0067503 A1 | 4/2004 | Tan et al. |
| 2004/0101822 A1 | 5/2004 | Wiesner et al. |
| 2004/0248856 A1 | 12/2004 | Lanza et al. |
| 2005/0252062 A1 | 11/2005 | Scrogin et al. |
| 2005/0255485 A1 | 11/2005 | Livak et al. |
| 2006/0068371 A1 | 3/2006 | Ortyn et al. |
| 2006/0106306 A1 | 5/2006 | Essner et al. |
| 2006/0183246 A1 | 8/2006 | Wiesner et al. |
| 2006/0245971 A1 | 11/2006 | Burns et al. |
| 2006/0251726 A1 | 11/2006 | Lin et al. |
| 2006/0257884 A1 | 11/2006 | Brawley et al. |
| 2007/0146873 A1 | 6/2007 | Ortyn et al. |
| 2008/0097225 A1 | 4/2008 | Tearney et al. |
| 2008/0139787 A1 | 6/2008 | De Jesus et al. |
| 2008/0213377 A1 | 9/2008 | Bhatia et al. |
| 2008/0292556 A1 | 11/2008 | Texier-Nogues et al. |
| 2009/0236541 A1* | 9/2009 | Lomnes ............... A61B 1/0646 250/362 |
| 2009/0317806 A1* | 12/2009 | Hasson ................ C12Q 1/686 435/286.1 |
| 2010/0036203 A1 | 2/2010 | Nakaoka et al. |
| 2010/0262017 A1 | 10/2010 | Frangioni |
| 2011/0028662 A1 | 2/2011 | Wiesner et al. |
| 2011/0152692 A1* | 6/2011 | Nie ..................... A61B 5/0077 600/473 |
| 2011/0199500 A1 | 8/2011 | Shimizu et al. |
| 2011/0282870 A1 | 11/2011 | Herzenberg et al. |
| 2012/0123205 A1 | 5/2012 | Nie et al. |
| 2012/0200694 A1 | 8/2012 | Garsha et al. |
| 2012/0330129 A1 | 12/2012 | Awdeh |
| 2013/0039848 A1 | 2/2013 | Bradbury et al. |
| 2013/0046173 A1* | 2/2013 | Hyde .................. A61B 5/4833 600/431 |
| 2013/0201317 A1 | 8/2013 | Ortyn et al. |
| 2014/0242600 A1 | 8/2014 | Xing et al. |
| 2015/0343091 A1 | 12/2015 | Yoo et al. |
| 2016/0169801 A1 | 6/2016 | Rogacs et al. |

FOREIGN PATENT DOCUMENTS

| | | |
|---|---|---|
| WO | WO-2004/108902 A2 | 12/2004 |
| WO | WO-2006/099445 A2 | 9/2006 |
| WO | WO-2007/002540 A2 | 1/2007 |
| WO | WO-2007/149062 A2 | 12/2007 |
| WO | WO-2009/029870 A2 | 3/2009 |
| WO | WO-2009/064964 A2 | 5/2009 |
| WO | WO-2011/084620 A2 | 7/2011 |
| WO | WO-2012/159205 A1 | 11/2012 |
| WO | WO-2013/192609 A1 | 12/2013 |

OTHER PUBLICATIONS

_Artemis handheld system; 2013. (Year: 2013).*

Ashitate, Y. et al., Simultaneous Mapping of Pan and Sentinel Lymph Nodes for Real-Time Image-Guided Surgery, Theranostics, 4(7):693-700 (2014).

Bae, S. et al., Fluorescent dye-doped silica nanoparticles: new tools for bioapplications, Chemical Communications, 25:48(17):2270-2282, (2012).

Baecker, V., Workshop: Image processing and analysis with ImageJ and MRI Cell Image Analyzer, Montpellier RIO Imaging, 93 pages (2010).

Ballou, B. et al., Sentinel Lymph Node Imaging Using Quantum Dots in Mouse Tumor Models, Bioconjugate Chem. 18:389-396 (2007).

Bogush, G. H. et al., Preparation of Monodisperse Silica Particles: Control of Size and Mass Fraction, J. Non-Cryst. Solids, 104:95-106 (1988).

Bradbury et al., Clinically-Translated Silica Nanoparticles as Dual-Modality Cancer-Targeted Probes for Image-Guided Surgery and Interventions, Integr. Biol., vol. 5:74-86, (2013).

Brien, J. F. et al., A Study of the Calcium Carbimide-Ethanol Interaction in Man, Europ. J. Clin. Pharmacol. 14(2):133-41 (1978).

Burns, et al., Fluorescent Silica Nanoparticles with Efficient Urinary Excretion for Nanomedicine, Nano Letters 9(1):442-8 (2009).

Cho, Y. S. et al., Cetuximab-conjugated magneto-fluorescent silica nanoparticles for in vivo colon cancer targeting and imaging, Cancer Letters, 299:63-71 (2010).

Crespi, M. D. et al., Mitroxantrone Affects Topoisomerase Activities in Human Breast Cancer Cells, Biochemical and Biophysical Research Communications, 136(2):521-8 (1986).

Cressman, S. et al., Binding and Uptake of RGD-Containing Ligands to Cellular $^{X}v^{\beta}3$ Integrins, Int J Pept Res Ther, 15:49-59 (2009).

Cristy, M. and Eckerman, K. F., Specific absorbed fractions of energy at various ages from internal photon sources (I-VII). Oak Ridge National Laboratory Report ORNL/TM-8381N1-7. Springfield, VA: National Technical Information Service, Dept. of Commerce (1987).

Crow, R. T. and Crothers, D. M., Inhibition of Topoisomerase I by Anthracycline Antibiotics: Evidence for General Inhibition of Topoisomerase I by DNA-Binding Agents, J. Med. Chem. 37(19):3191-3194 (1994).

Dejong, M. et al., Comparison of $^{111}$In-Labeled Somatostatin Analogues for Tumor Scintigraphy and Radionuclide Therapy, Cancer Res., 58:437-41 (1998).

De Jong, M. et al., Internalization of radiolabelled [DTPA$^0$]octreotide and [DOTA0,Tyr$^3$]ocetreotide:peptides for somatostatin receptor-targeted scintigraphy and radionuclide therapy, Nucl. Med. Commun., 19(3):283-288 (1998).

Denny, W. A. and Baguley, B. C., Dual Topoisomerase I/II Inhibitors in Cancer Therapy, Curr. Top. Med. Chem., 3(3):339-353 (2003).

(56) References Cited

OTHER PUBLICATIONS

Ding, Y. et al., The performance of thiol-terminated PEG-paclitaxel-conjugated gold nanoparticles, Biomaterials, 34:10217-10227 (2013).
Doronina, S. O. et al., Novel Peptide Linkers for Highly Potent Antibody Auristatin Conjugate, Bioconjugate Chem., 19(10):1960-1963, (2008).
Foglesong, P. D. et al., Doxorubicin inhibits human DNA topoisomerase I, Cancer Chemother. Pharmacol., 30(2):123-125 (1992).
Gatto, B. et al., Identification of Topoisomerase I as the Cytotoxic Target of the Protoberberine Alkaloid Coralyne, Cancer Res., 15(12):2795-2800 (1996).
Gladson, C. A. and Cheresh, D. A., Glioblastoma Expression of Vitronectin and Alpha v Beta 3 Integrin, Adhesion Mechanism for Transformed Glial Cells, J. Clin. Invest. 88:1924-1932 (1991).
Herz et al., Dye Structure-Optical Property Correlations in Near-Infrared Fluorescent Core-Shell Silica Nanoparticles, J. Mater. Chem., vol. 19:6341-6347, (2009).
Herz, E. et al., Large Stokes-Shift Fluorescent Silica Nanoparticles with Enhanced Emission over Free Dye for Single Excitation Multiplexing, Macromol Rapid Commun., 30(22):1907-1910 (2009).
Hilderbrand, S. A. and Weissleder, R., Near-infrared fluorescence: application to in vivo molecular imaging, Curr. Opin. Chem. Bioi., 14:71-9 (2010).
International Search Report, PCT/US2014/073053, 5 pages, dated Mar. 25, 2015.
Kim, S. et al., Near-infrared fluorescent type II quantum dots for sentinel lymph node mapping, Nature Biotechnology 22(1):93-97 (2004).
Koole et al., Paramagnetic lipid-coated silica nanoparticles with a fluorescent quantum dot core: a new contrast agent platform for multimodality imaging, Bioconjugate Chem., 19(12):2471-2479 (2008).
Krenning, E. P. et al, Somatostatin Receptor Scintigraphy with Indium-111-DTPA-D-Phe-1-Octreolide in Man: Metabolism, Dosimetry and Comparison with Iodine-123-Tyr-3-Octreotide, J Nucl. Med. 33:652-8 (1992).
Larson, D. R. et al., Silica Nanoparticle Architecture Determines Radiative Properties of Encapsulated Fluorophores, Chem. Mater. 20:2677-2684 (2008).
Lewis et al. Comparison of Four 64Cu-labeled Somatostatin Analogs in Vitro and in a Tumor-Bearing Rat Model: Evaluation of New Derivatives for Positron Emission Imaging and Targeted Radiotherapy. J Med Chem., 42:1341-7 (1999).
Li, T. et al., Human Topoisomerase I Poisoning by Protoberberines: Potential Roles for Both Drug-DNA and Drug-Enzyme Interactions, Biochemistry, 39(24):7107-7116 (2000).
Li, Z. et al., $^{64}$Cu-labeled Tetrameric and Octomeric RGD Peptides for Small-Animal PET of Tumor $\alpha_v\beta_3$ Integrin Expression, J. Nucl Med. 48:1162-1171 (2007).
Loir, B. et al., Expression of the MC1 Receptor Gene in Normal and Malignant Human Melanocytes. A Semiquantitative RT-PCR Study, Cell Mol. Biol., 45(7):1083-1092 (1999).
Makhey et al., Sbustitute Benzo[i]phenanthridines as Mammalian Topoisomerase-Targeting Agents, Bioorg. Med. Chem. 11(8):1809-1820 (2003).
Matlab, Image Processing Toolbox™, User's Guide, MathWorks, Inc., R2016b, 828 pages, (2016).
McKeage et al., Phase I and Pharmacokinetic Study of an Oral Platinum Complex Given Daily for 5 Days in Patients With Cancer, Journal of Clinical Oncology, 15(7):2691-2700 (1997).
Montet, X. et al., Multivalent Effects of RGD Peptides Obtained by Nanoparticle Display, J. Med. Chem. 49:6087-6093 (2006).
Ohnishi, S. et al., Organic Alternatives to Quantum Dots for Intraoperative Near-Infrared Fluorescent Sentinel Lymph Node Mapping, Molecular Imaging 4(3):172-181 (2005).
Ow, H. et al., Bright and Stable Core-Shell Fluorescent Silica Nanoparticles, Nano Letters, 5(1):113-117 (2005).
Papamicheal, D., The Use of Thymidylate Synthase Inhibitors in the Treatment of Advanced Colorectal Cancer: Current Status, the Oncologist, 4:478-487 (1999).
Patel, K. N. et al., MUC1 plays a role in tumor maintenance in aggressive thryroid carcinomas, Surgery 138(6):994-1002 (2005).
Piatyszek, M.A. et al., Iodo-Gen-Mediated Radioiodination of Nucleic Acids, J. Anal. Biochem. 172(2):356-359 (1988).
Pommier, Y., Topoisomerase I inhibitors: camptothecins and beyond, Nat. Rev. Cancer, 6(10):789-802 (2006).
Promet, Prostate cancer molecular-oriented detection and treatment of minimal residual disease, the Promet Consortium, 20 pages (2008).
Quest Medical Imaging, Instructions for Use, Artemis Handheld System, Quest Group, Version 2.5, (2013).
Reubi, J.C. et al., Distribution of Somatostatin Receptors in Normal and Tumor Tissue, Metabolism, 39(9)(2):78-81 (1990).
Reubi, J.C. et al., Somatostatin Receptors and Their Subtypes in Human Tumors and in Peritumoral Vessels, Metabolism, 45(8)(1):39-41 (1996).
Ruoslahti, E. and Pierschbacher, M. D., New Perspectives in Cell Adhesion: RGD and Integrins, Science 238:491 (1987).
Sadasivan, et al., Alcoholic Solvent Effect on Silica Synthesis—NMR and DLS Investigation, J. Sol-Gel Science and Technology, 12:5-14 (1998).
Santra, S. et al., Fluorescent nanoparticle probes for cancer imaging, Technology in Cancer Research & Treatment, 4(6):593-602, (2005).
Seftor, R. E. B. et al., Role of the alpha v beta 3 integrin in human melanoma cell invasion, Proc. Natl. Acad. Sci., 89:1557-1561 (1992).
Seymour, L.W., Passive Tumor Targeting of Soluble Macromolecules and Drug Conjugates, Critical Reviews in Therapeutic Drug Carrier Systems, 9(2):135-187 (1992).
Soster, M. et al., Targeted dual-color silica nanoparticles provide univocal identification of micrometastases in preclinical models of colorectal cancer, International Journal of Nanomedicine, 7:4797-4807 (2012).
Stabin, M. G. et al., OLINDA/EXM: The Second-Generation Personal Computer Software for Internal Dose Assessment in Nuclear Medicine, J Nucl Med. 46:1023-1027 (2005).
Tanaka, E. et al, Image-Guided Oncologic Surgery Using Invisible Light: Completed Pre-Clinical Development for Sentinel Lymph Node Mapping, Annals of Surgical Oncology 13(12):1671-1681 (2006).
Tran, H. N. et al., Dye-doped silica-based nanoparticles for bioapplications, Adv. Nat. Sci.:Nanosci. Nanotechnol. 4:13 pages, (2013) doi:10.1088/2043-6262/4/4/043001.
Vejayakumaran, P. et al., Structural and thermal characterizations of silica nanoparticles grafted with pendant maleimide and epoxide groups, Journal of Colloid and Interface Science, 328:81-91 (2008).
Vorst, S. et al., Dose Optimization for Near-Infrared Fluorescence Sentinel Lymph Node Mapping in Melanoma Patients, BR J Dermatol. 168(1)93-98 (2013).
Wang, X. et al., Folate Receptor-Targeted Aggregation-Enhanced Near-IR Emitting Silica Nanoprobe for One-Photon in Vivo and Two-Photon ex Vivo Fluorescence Bioimaging, Bioconjugate Chemistry, 22:1438-1450 (2011).
Wang, Y. et al., Tumor cell targeted delivery by specific peptide-modified mesoporous silica nanoparticles, J. Mater. Chem., 22:14608-14616, (2012).
Webb, et al., Sphingomyelin-cholesterol liposomes significantly enhance the pharmacokinetic and therapeutic properties of vincristine in murine and human tumour models, British J. of Cancer 72:896-904 (1995).
Webster, A. et al., Optical calcium sensors: development of a generic method for their introduction to the cell using conjugated cell penetrating peptides, Analyst, 130:163-70 (2005).
Written Opinion, PCT/US2014/073053, 7 pages, dated Mar. 25, 2015.
Wu, P. et al., Imaging Breast Cancer Cells and Tissues Using Peptide-Labeled Fluorescent Silica Nanoparticles, Journal of Nanoscience and Nanotechnology, 8(5):2483-2487 (2008).
Xu, Z. et al., DNA Minor Groove Biding-Directed Poisoning of Human DNA Topoisomerase I by Terbenzimidazoles, Biochemistry 37(10):3558-3566 (1998).

\* cited by examiner

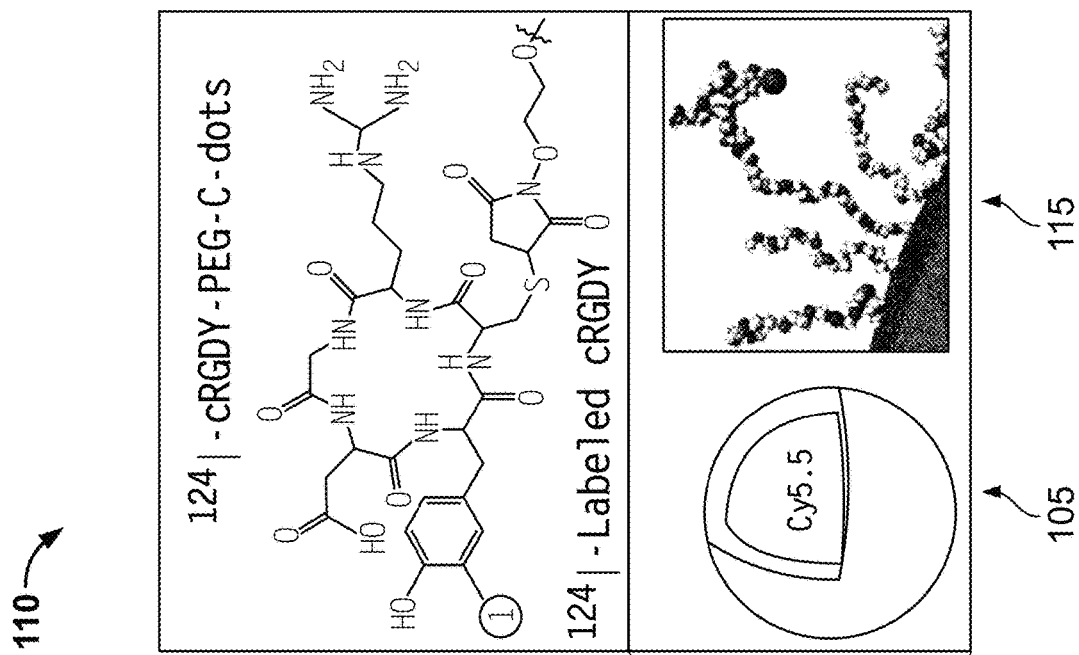
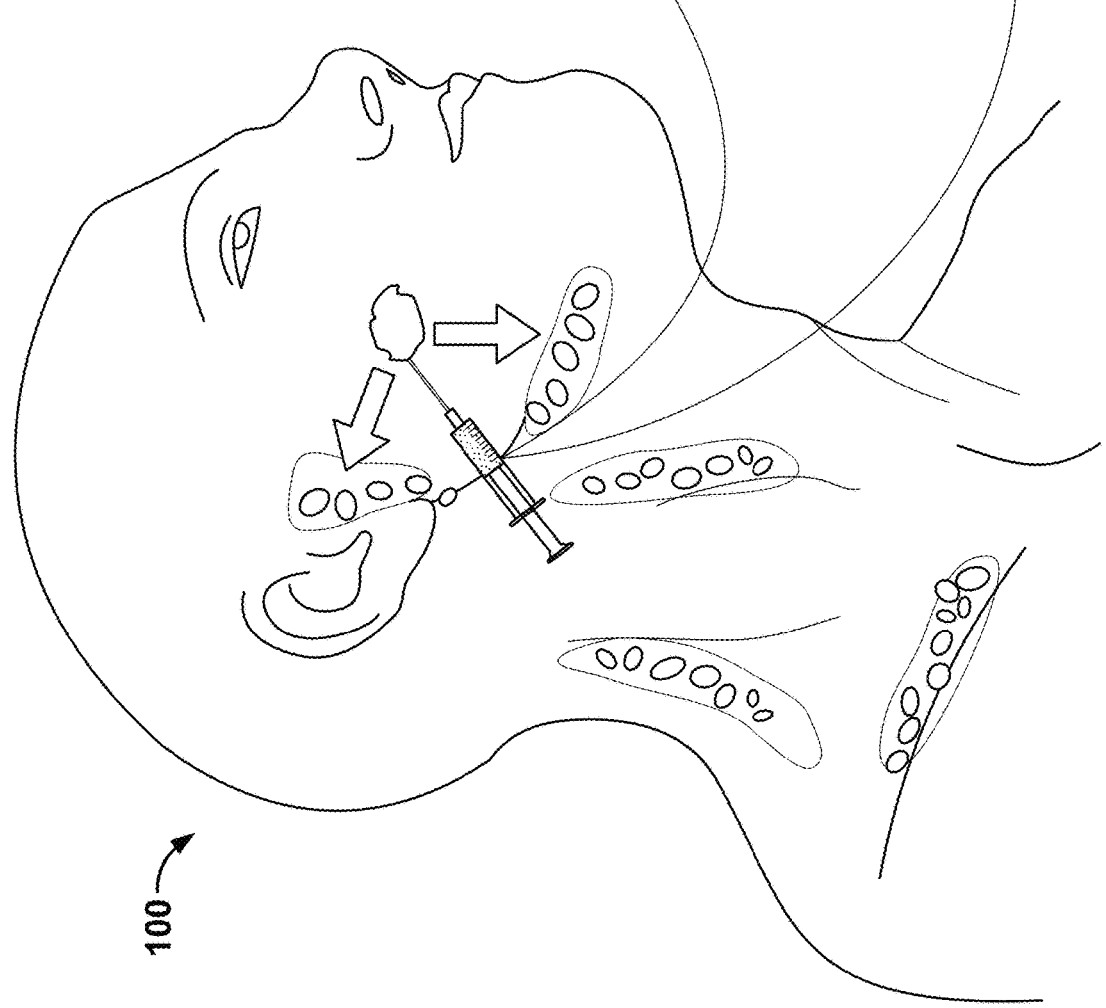
FIG. 1A
FIG. 1B

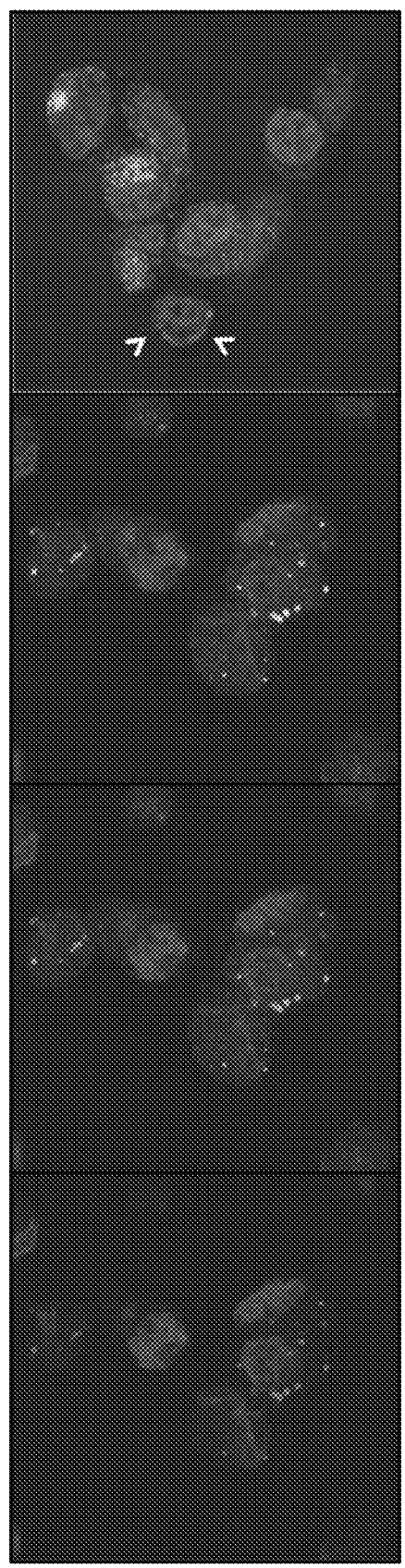

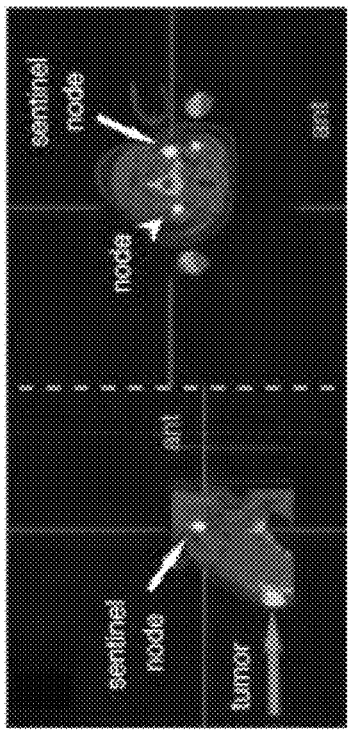
FIG. 6A
FIG. 6B
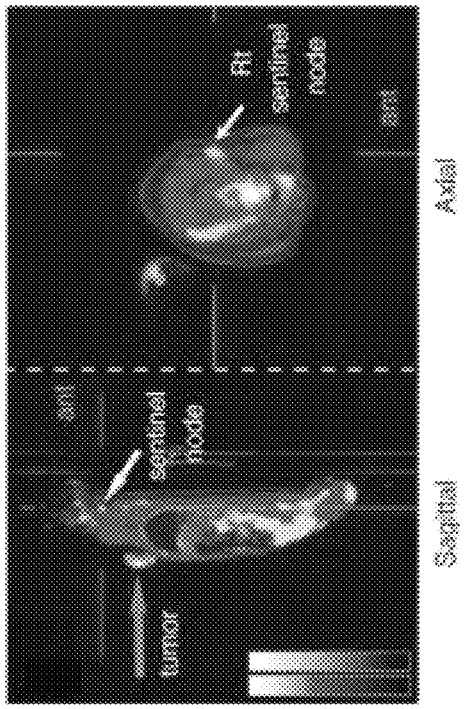
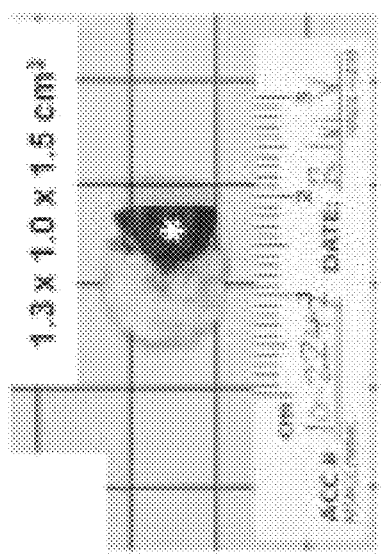
FIG. 6C
FIG. 6D

FIG. 6K
FIG. 6I
FIG. 6G
FIG. 6E
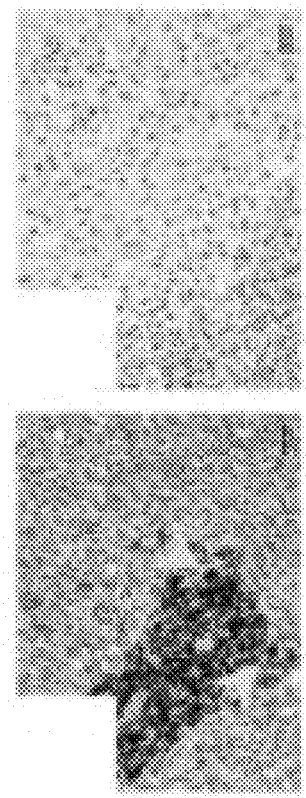
FIG. 6L
FIG. 6J
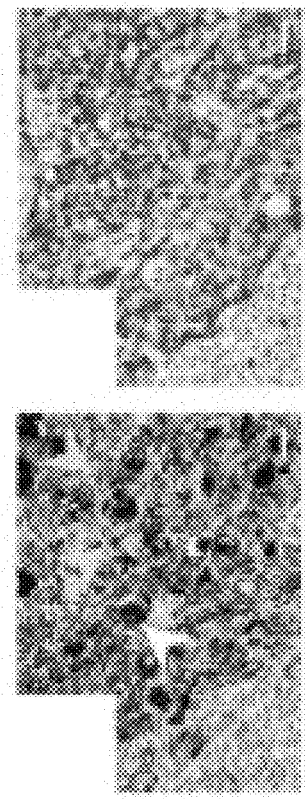
FIG. 6H
FIG. 6F

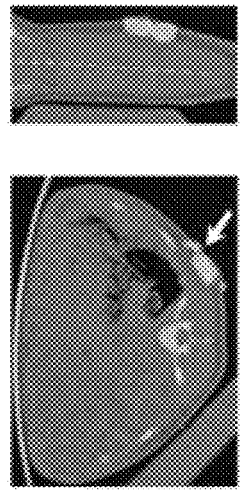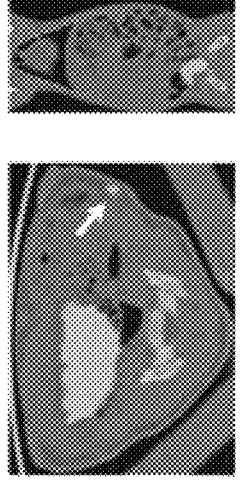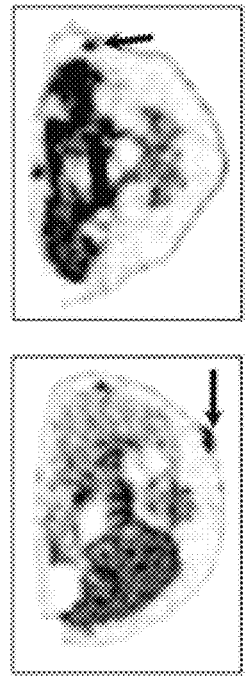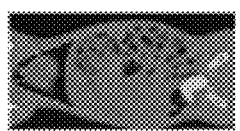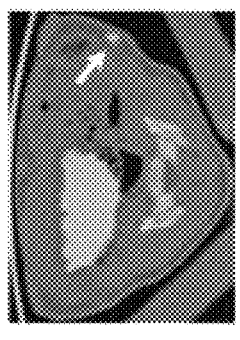
FIG. 7A FIG. 7B FIG. 7E FIG. 7F
FIG. 7C FIG. 7D FIG. 7G FIG. 7H
FIG. 7I

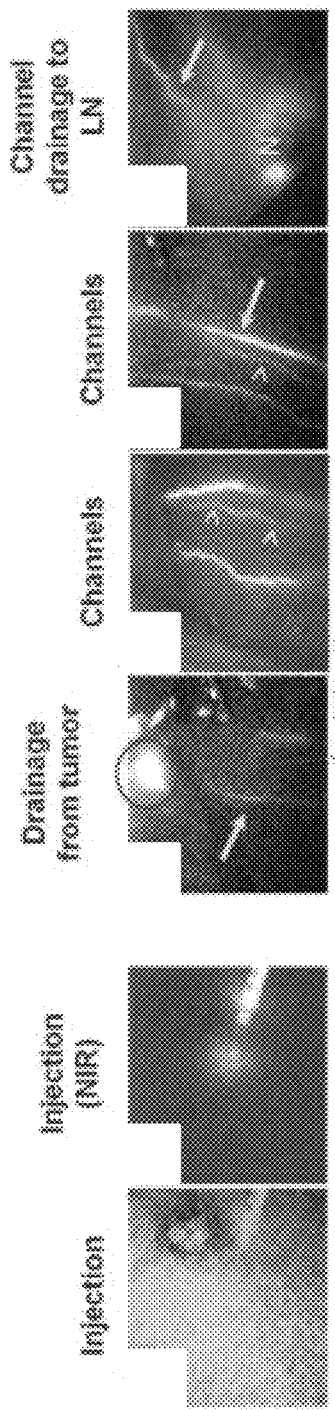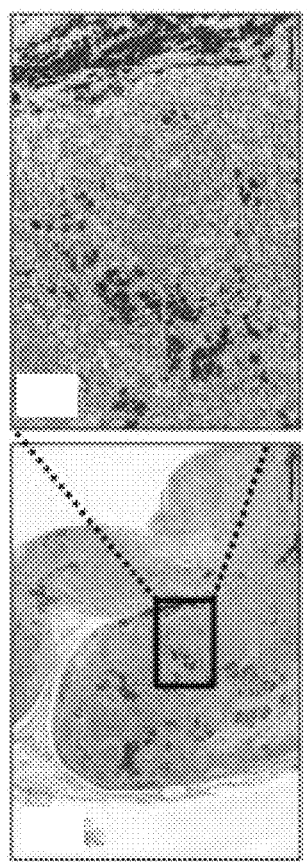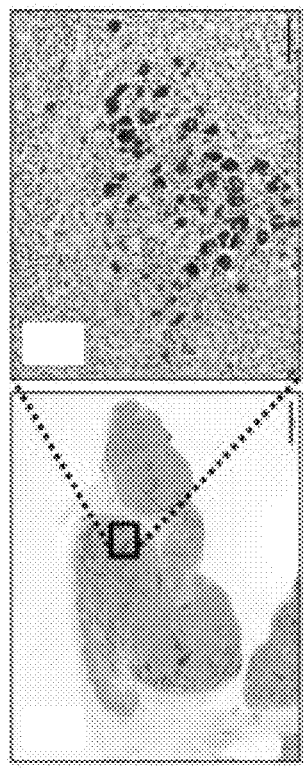

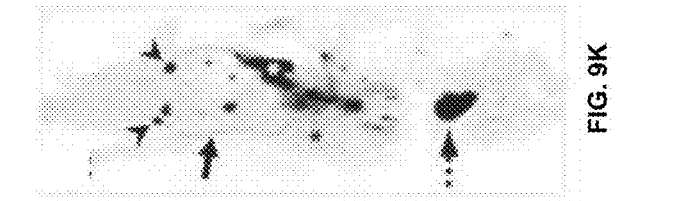
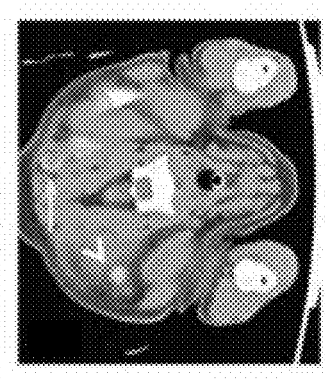 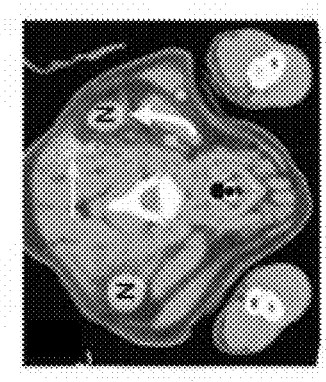
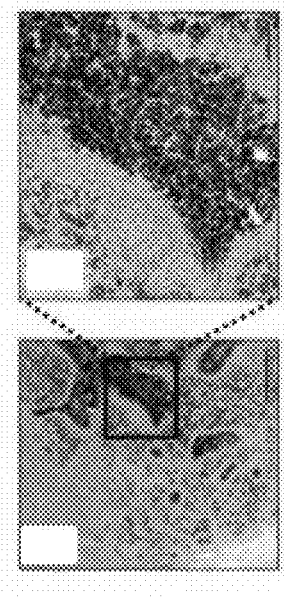
 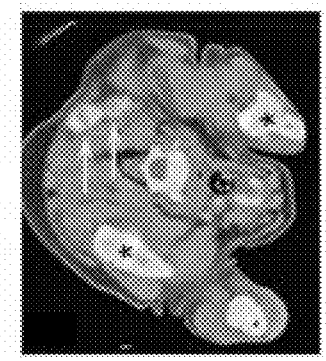
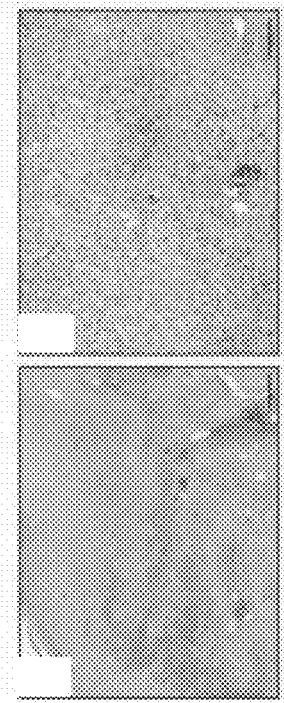
FIG. 9A FIG. 9B FIG. 9C FIG. 9D FIG. 9E FIG. 9F FIG. 9G FIG. 9H FIG. 9I FIG. 9J FIG. 9K

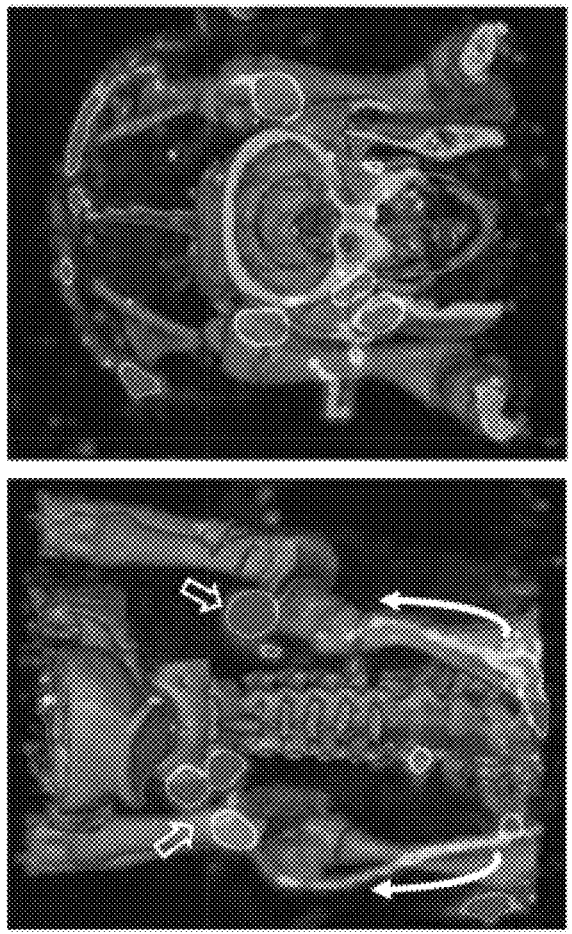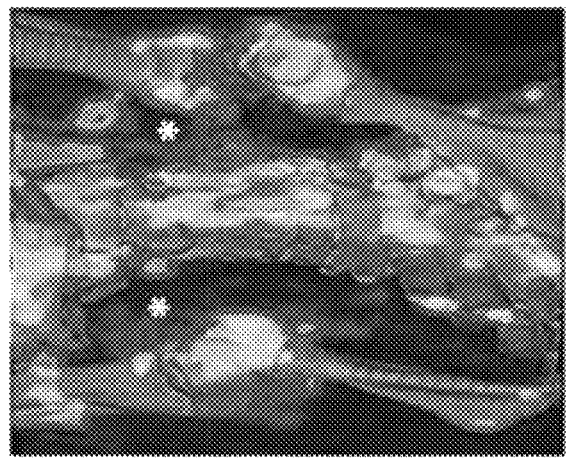

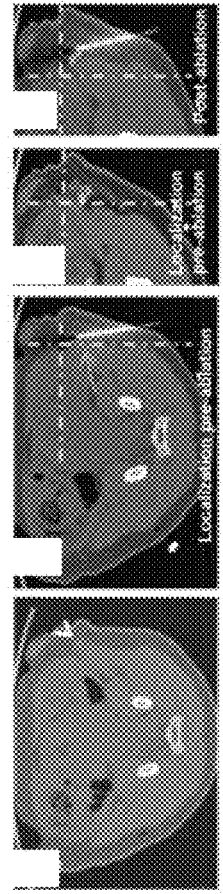
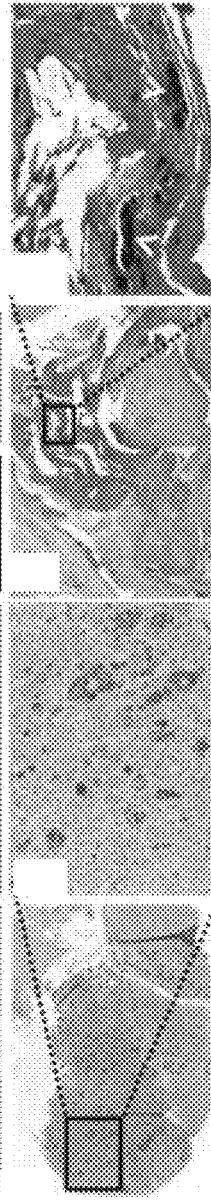
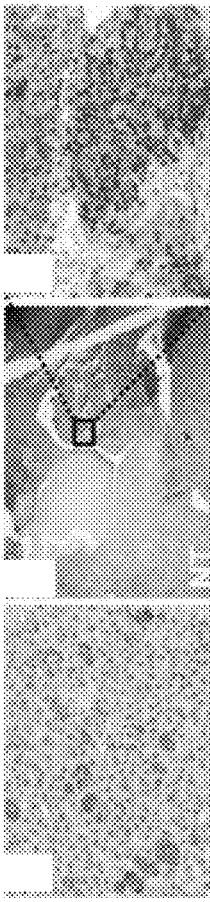
FIG. 11A FIG. 11B FIG. 11C FIG. 11D
FIG. 11E FIG. 11F FIG. 11G FIG. 11H
FIG. 11I FIG. 11J FIG. 11K FIG. 11L
FIG. 11M FIG. 11N FIG. 11O

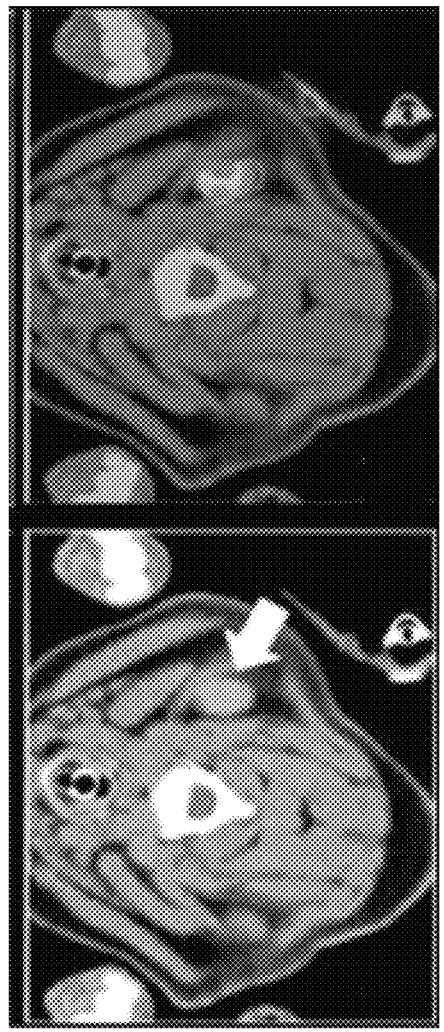

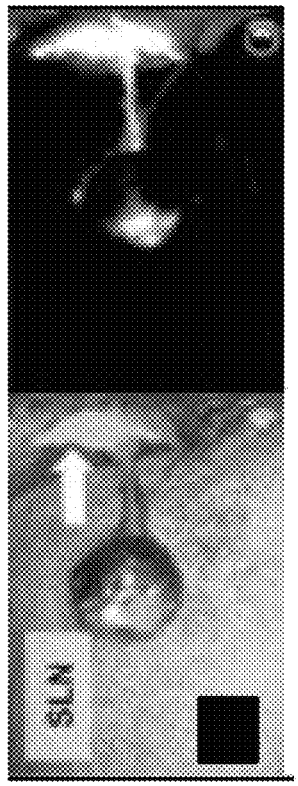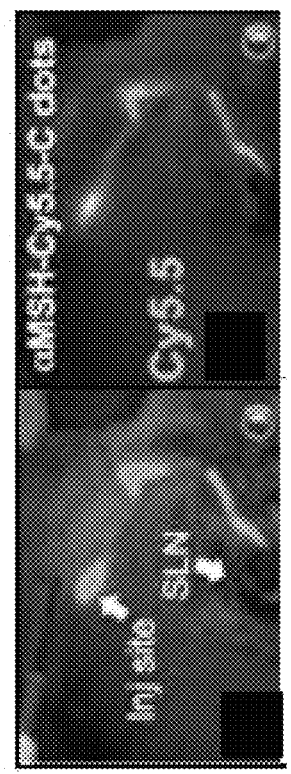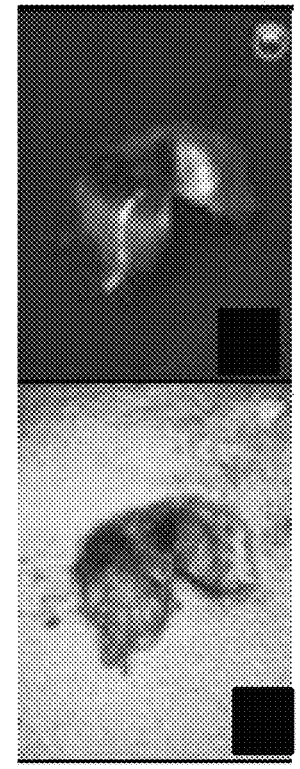

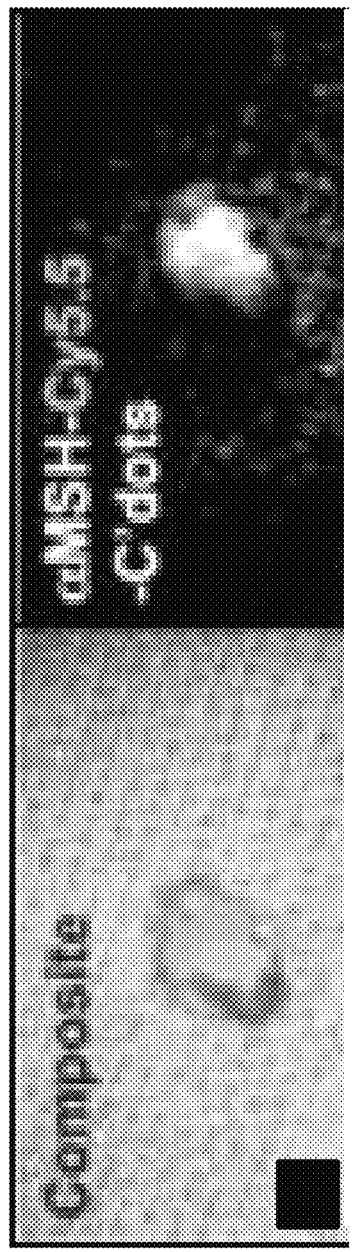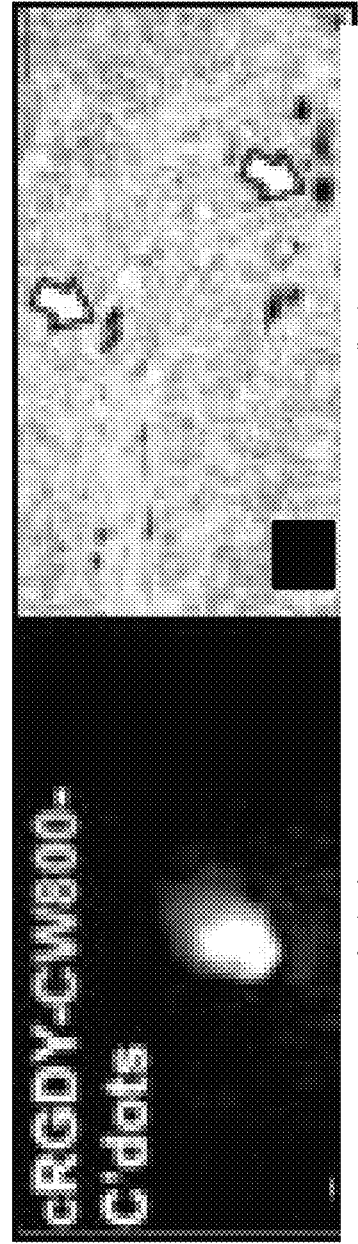
FIG. 14A  FIG. 14B  FIG. 14C  FIG. 14D

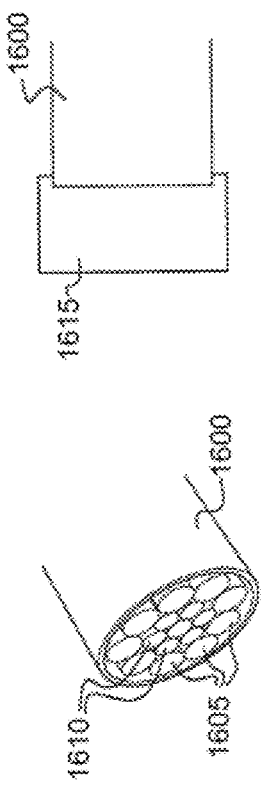
FIG. 16A
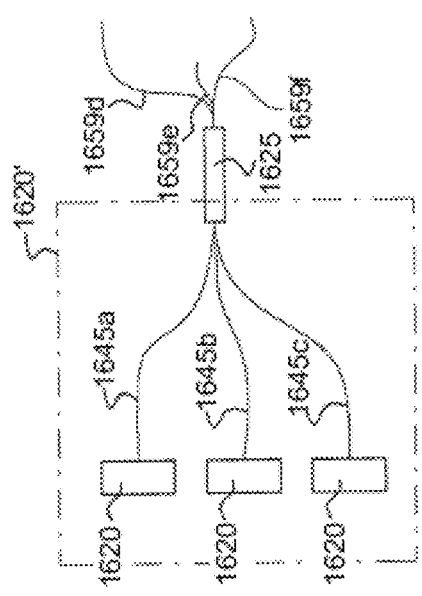
FIG. 16B
FIG. 16C
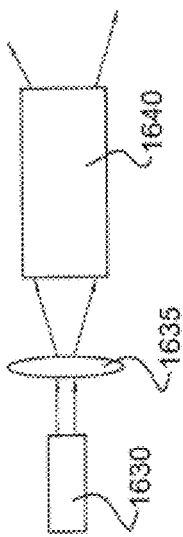
FIG. 16D

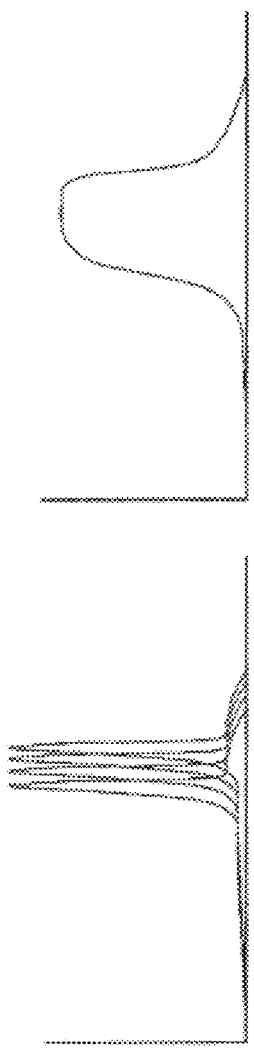
FIG. 18B
FIG. 18A
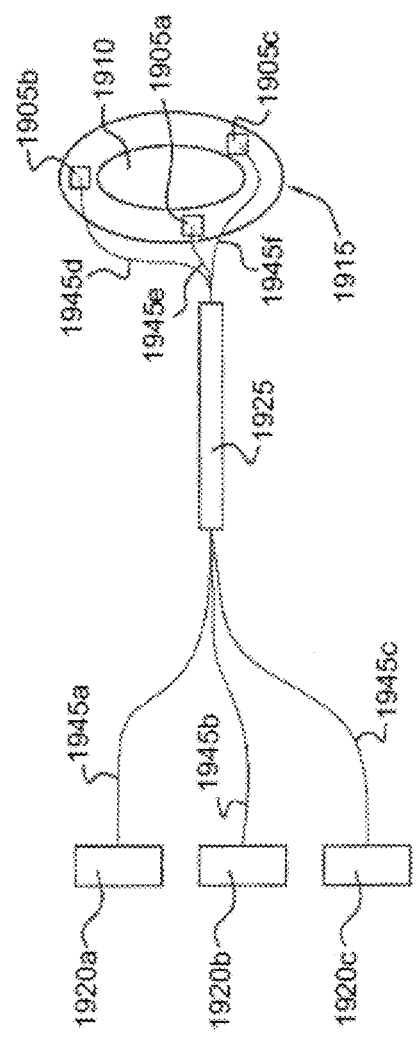
FIG. 19

**Blocking Filters
to Match Light Engine**

Output Spectrum

Filter Blocks Chemical Emission Wave Lengths of C-Dots

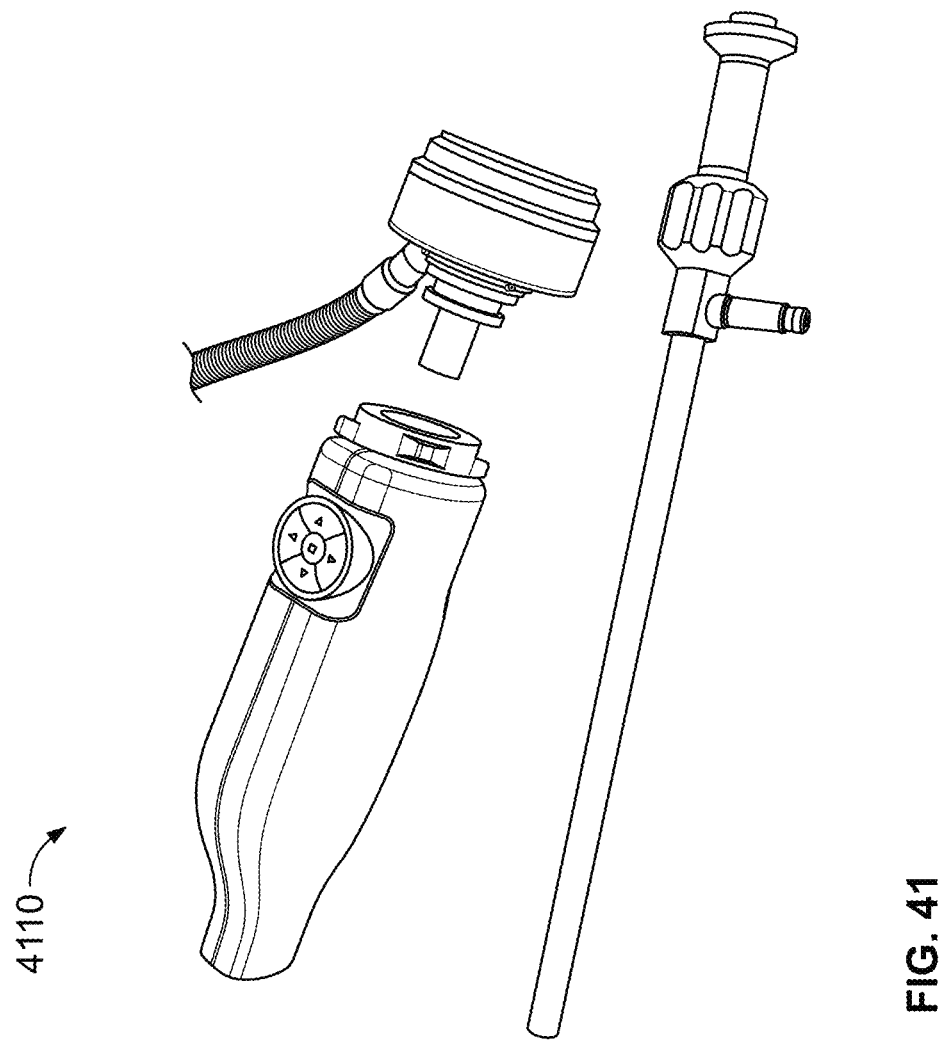
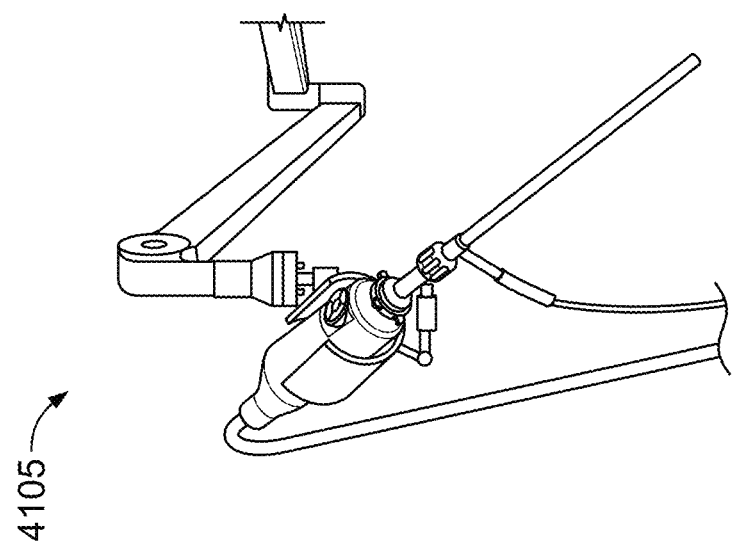
FIG. 41

Video Image Processing Block Diagram

```
5005
┌─────────────────────────────────────────────────────────┐
│ A Light Source Configured to Deliver Multiple Excitation │
│ Wavelengths of Light to Excite a Plurality of Fluorescent│
│   Reporters, Thereby Producing Fluorescent Light at     │
│         Two or More Distinguishable Wavelengths          │
└─────────────────────────────────────────────────────────┘
                            │
                            ▼
5010
┌─────────────────────────────────────────────────────────┐
│        A Prism Configured to Direct Light Received       │
│   Through a Lens onto a Plurality of Spatially-separated │
│     Detectors Such that Said Detectors can Measure,      │
│   in Real Time, Different Emitted Signals Simultaneously │
└─────────────────────────────────────────────────────────┘
                            │
                            ▼
5015
┌─────────────────────────────────────────────────────────┐
│       A Processor Configured to Process Signals          │
│ Corresponding to the Detected Fluorescent Light at the   │
│ Two or More Distinguishable Wavelengths to Provide       │
│        Images of Fluorescence Within a Subject           │
└─────────────────────────────────────────────────────────┘
```

FIG. 50

SYSTEMS, METHODS, AND APPARATUS FOR MULTICHANNEL IMAGING OF FLUORESCENT SOURCES IN REAL-TIME

CROSS REFERENCE TO RELATED APPLICATIONS

This application is a divisional of U.S. application Ser. No. 13/588,066 filed on Dec. 31, 2014, which claims the benefit of U.S. Application Ser. No. 61/987,426 filed on May 1, 2014 and 61/922,619 filed on Dec. 31, 2013, the disclosures of which are hereby incorporated by reference in their entireties.

FIELD OF THE INVENTION

The invention relates generally to in vivo imaging systems and methods. More particularly, in certain embodiments, the invention relates to a multichannel imaging system capable of detecting and distinguishing multiple fluorescent light sources simultaneously.

BACKGROUND OF THE INVENTION

The pharmaceutical industry faces increasing pressure to provide accurate and effective information and therapy. New imaging technologies are central to the response to this pressure, and significant strides have been made, for example, in the development of detectable moieties and systems that image them. Particular effort is directed toward imaging technologies that can support cancer therapy, for example, in hopes of improving the mapping of surgical margins, identifying metastatic lymph nodes, and sparing normal vital tissues and neurovascular structures. Effort is also directed toward stratifying or monitoring patient populations, identifying those who are responding particularly well or poorly to a given therapeutic regimen. With the developments of imaging technologies including new systems and probes, there is a growing need to detect numerous signals and input simultaneously for the most accurate and conclusive diagnoses.

Malignant melanoma is one of the fastest rising cancers in the US, and is estimated to rise by 1% every year. The incidence rate of melanoma has risen 3-fold in the US over the past 3 decades, with similar rates reported in Europe. The highest incidence rates have been reported from Australia and New Zealand (40 to 60 cases per 100 000 inhabitants and year). The American Cancer Society estimated that there were will be 76250 new melanoma cases diagnosed in 2012, resulting in 12 190 deaths (*ACS Cancer Facts & Figs.*, Atlanta Ga., 2012); in the United States, it now ranks the fifth most common cancer in males and sixth most common in females. Prognosis is largely determined by thickness and ulceration of primary tumor. However, the presence of lymph node metastases is the most important prognostic predictor (Balch, *J. Clin. Oncol.*, (2001)) and considerable effort goes into examining the regional lymph nodes for the presence of lymphatic metastasis.

Early diagnosis and treatment are essential to minimizing morbidity and mortality. Definitive treatment for primary cutaneous melanoma is surgical resection in the form of a wide local excision. Adjuvant radiation is added for specific indications including locally invasive tumors and/or spread to multiple regional lymph nodes. There are no currently accepted standard-of-care systemic treatment options available. However, systemic treatment of melanoma is available in the clinical trials setting and is only offered to patients based on regional node risk stratification (i.e., SLN mapping). It is therefore essential to accurately stage melanoma in its earlier phases by carefully examining regional nodes for metastatic disease spread. The use of molecular imaging tools (Weissleder, *Science*, (2006)), may aid in this process, improving disease visualization and staging during SLN biopsy procedures, while reducing the risk of lymphedema and other side effects of more extensive node dissection by harvesting only disease-bearing nodes. The presence of lymph node metastases is a vital prognostic predictor, and accurate identification by imaging has important implications for disease staging, prognosis, and clinical outcome. Sentinel lymph node (SLN) mapping procedures are limited by a lack of intraoperative visualization tools that can aid accurate determination of disease spread and delineate nodes from adjacent critical neural and vascular structures.

In addition to sentinel lymph node mapping, other disease areas or biological abnormalities would greatly benefit from improved in vivo imaging technologies. There is a critical need for better intraoperative visualization of peripheral nerves and nodal disease in prostate cancer. The ability to evaluate residual disease in prostate cancer intraoperatively is also another unmet need that would benefit from new in vivo imaging techniques.

Presented herein are systems and methods that circumvent limitations of previous imaging technologies by employing biocompatible particle-based platforms coupled with a portable device capable of multichannel imaging with improved signal-to-noise ratio. In addition to diagnostic imaging, the technologies can be used with image-guided surgical and interventional procedures.

SUMMARY OF THE INVENTION

Described herein are systems, apparatus, and methods for simultaneously imaging, in real-time, different fluorescent sources within a subject using a portable multichannel fluorescent camera. Also described are portable imaging systems capable of detecting light from multiple probes species simultaneously with high signal-to-noise ratio. These systems offer advantages over pre-existing systems that cannot simultaneously detect and distinguish more than one fluorescent probe species in real-time.

In some embodiments, the imaging systems of the present invention are used to image disease or cellular abnormalities for diagnostic as well as intraoperative purposes. An exemplary intraoperative imaging device, the ArteMIS™ handheld fluorescence camera system (Quest Medical Imaging, Middenmeer, The Netherlands) (FIG. 5A), is adapted for both minimally invasive laparoscopic (FIGS. 5B and 5C) and open surgical procedures, (FIG. 5C). The system is a hand-held, multi-channel fluorescence imaging camera for intraoperative imaging guidance, producing high-resolution visible (color) images and fine-tuned near-infrared (NIR) fluorescent signals, which are simultaneously acquired in real-time. This capability allows for motion-free overlaying. This hand-held device is advantageous for SLN mapping procedures, for example, as it can be easily positioned to view otherwise difficult anatomic locations, such as the head and neck.

The capability of acquiring simultaneous images of different fluorescence wavelengths (i.e., multispectral imaging) allows use of fluorescence imaging guidance for surgical and interventional procedures. In certain embodiments, the sensors in the device are physically aligned such that a single axis lens delivers images of the specifically tuned wavelength to the appropriate sensor. Filtering out the required wavelength of interest, as well as being able to individually control each of these sensors, which are triggered to start acquiring photons at exactly the same time and same viewing position, is of great importance. The tight integration of the light engine, controllable from the camera system, allows optimization based on imaging feedback.

Thus, presented herein is an in vivo (or in vitro) imaging system comprising a light engine to deliver multiple excitation wavelengths to one or more dye-containing nanoparticles (such as C dots), which can be excited by the multiple wavelengths, and further distinguished by their different emitted signals, by a device capable of measuring, in real-time, the different emitted signals simultaneously in vitro and/or in vivo (e.g., intraoperatively).

Embodiments presented herein include, for example, use of the in vivo imaging system to evaluate metastatic melanoma by visualizing different tumor lymphatic drainage pathways and nodal distributions following local injection of probe species. Real-time intraoperative visualization of peripheral nerves and nodal disease in prostate cancer, and other cancers, can be performed using targeted dual-modality probe species. The real-time visualization for intraoperative visualization of nerves can also be conducted for parotid tumors, and for tumors of the larynx for mapping laryngeal nerves. In some embodiments, the system is used to perform real-time intraoperative evaluation of residual disease in prostate cancer using dual-modality probe species surface-modified with multiple cancer-directed ligands.

The apparatus and systems differ from previous imaging systems in their ability to carry out simultaneous detection of light signals at different wavelengths in real-time. In some embodiments, the imaging apparatus comprises a multichannel fluorescence camera system that simultaneously detects multiple wavelengths from multiple dyes in real-time. In some embodiments, the imaging apparatus comprises a hand-held fluorescent imaging system that uses multiple detectors and associated circuitry that can collect distinguishable signals from the multiple types of probe species with higher signal-to-noise ratio. In some embodiments, the system does not distinguish multiple signal types received at a single detector with optical time division multiplexing, as do other previous imaging systems.

Furthermore, in certain embodiments, presented herein is a clinically-translated, integrin-targeting platform, for use with both PET and optical imaging, that meets a number of key design criteria for improving SLN tissue localization and retention, target-to-background ratios, and clearance from the site of injection and the body. The use of such agents for selectively probing critical cancer targets may elucidate important insights into cellular and molecular processes that govern metastatic disease spread. Coupled with portable, real-time optical camera systems, it can be shown that pre-operative PET imaging findings for mapping metastatic disease in clinically-relevant larger-animal models can be readily translated into the intraoperative setting for direct visualization of the draining tumor lymphatics and fluorescent SLNs with histologic correlation. Also discussed herein is the specificity of this platform, relative to the standard-of-care radiotracer, $^{18}$F-FDG, for potentially discriminating metastatic disease from inflammatory processes in the setting of surgically-based or interventionally-driven therapies.

In one aspect, the invention provides a method for optical imaging of a region within a subject, the method comprising: (a) administering to the subject two or more different probe species each comprising a fluorescent reporter; (b) directing excitation light into the subject, thereby exciting the fluorescent reporters; (c) simultaneously detecting fluorescent light of different wavelengths, the detected fluorescent light having been emitted by the fluorescent reporters of the probe species in the subject as a result of excitation by the excitation light so as to discriminate between signals received from each probe species; and (d) processing signals corresponding to the detected fluorescent light to provide one or more images (e.g. a real-time video stream) of the region within the subject. In some embodiments, step (c) is performed without optical time division multiplexing.

In some embodiments, at least one of the probe species comprises nanoparticles. In some embodiments, the average diameter of the nanoparticle is less than about 20 nm, and more preferably less than 15 nm, and more preferably less than 10 nm, e.g., where the average diameter is as measured in vitro or in vivo (e.g., in saline solution, or in use). Additionally, in certain embodiments, the nanoparticles are advantageously no smaller than 3 nm in size, as discussed in more detail below. In certain embodiments, the nanoparticles are substantially monodisperse (e.g., all particles have diameter less than about 20 nm, less than about 15 nm, or less than about 10 nm, and/or all particles are within a range of +/−5 nm, +/−4 nm, or +/−3 nm in diameter of each other). In some embodiments, the nanoparticles have a silica architecture and dye-rich core. In some embodiments, the dye rich core comprises a fluorescent reporter. In some embodiments, the fluorescent reporter is a near infrared or far red dye. In some embodiments, the fluorescent reporter is selected from the group consisting of a fluorophore, fluorochrome, dye, pigment, fluorescent transition metal, and fluorescent protein. In some embodiments, the fluorescent reporter is selected from the group consisting of Cy5, Cy5.5, Cy2, FITC, TRITC, Cy7, FAM, Cy3, Cy3.5, Texas Red, ROX, HEX, JA133, AlexaFluor 488, AlexaFluor 546, AlexaFluor 633, AlexaFluor 555, AlexaFluor 647, DAPI, TMR, R6G, GFP, enhanced GFP, CFP, ECFP, YFP, Citrine, Venus, YPet, CyPet, AMCA, Spectrum Green, Spectrum Orange, Spectrum Aqua, Lissamine and Europium.

In some embodiments, following step (c), a fluorescent reporter is also present in the subject at one or more locations not substantially co-located with another fluorescent reporter.

In some embodiments, the subject is a human.

In some embodiments, the method further comprises the step of detecting or monitoring a cellular abnormality or disease using the one or more images from the subject and/or detecting or monitoring normal tissue structures (e.g., marking and discriminating normal tissue structures such as glandular tissues (e.g., parathyroid gland), neural tissues, and/or vascular structures that are present within or lie adjacent to the surgical bed (e.g., are near, or mixed in with, disease or tumor tissue).

In some embodiments, the cellular abnormality or disease comprises at least one member selected from the group consisting of inflammation, cancer, cardiovascular disease, respiratory disease, dermatologic disease, ophthalmic disease, infectious disease, immunologic disease, central nervous system disease, inherited diseases, metabolic diseases, environmental diseases, bone-related disease, neurodegenerative disease, and surgery-related complications. In some embodiments, the cellular abnormality or disease is sentinel lymph nodes in metastatic melanoma. In some embodiments, the cellular abnormality or disease is an abnormality of peripheral nerves or nodal disease in prostate cancer. In some embodiments, the cellular abnormality or disease is residual disease in prostate cancer.

In certain embodiments, processing signals in step (d) comprises performing, by a processor of a computing device, one or more operations on the signal, the one or more operations selected from the group consisting of scaling, interlacing, chroma resampling, alpha blend mixing, color plane sequencing, frame buffering, test pattern generation, 2D media filtering, color space conversion, control synchronization, and frame reading.

In certain embodiments, the method further comprises analyzing, by a processor of a computing device, processed signals based upon information retrieved from a medical imaging data repository (e.g., Nanomed).

In certain embodiments, the method further comprises graphically augmenting, by a processor of a computing device, the one or more images (e.g., video streams) using (additional) data retrieved from the medical imaging data repository, wherein graphically augmenting comprises graphically rendering the images with the additional data (e.g., superimposing text or other information from the medical imaging data repository onto the video stream); and displaying, on a display of a computing device, the one or more graphically augmented images (e.g., graphically augmented video streams).

In certain embodiments, the additional data comprises one or more data selected from the group consisting of text (i.e., particle type/composition, ligand, animal model, dose/volume of injectate), optical/PET imaging parameters (i.e., max pixel intensity, % ID/g), camera performance parameters (i.e., gain, exposure time), nodal fluorescence spectral signature (e.g., signal distribution), and histology (e.g., tumor burden).

In certain embodiments, the method comprises visually enhancing, by a processor of a computing device, the one or more images (e.g., video streams); and displaying, on a display of a computing device, the one or more visually enhanced images. In certain embodiments, visually enhancing the one or more images comprises enhancing the graphical contrast between two or more different fluorescent reporters. In certain embodiments, processing signals in step (d) further comprises performing spectral deconvolution of the images. In certain embodiments, the method further comprises performing, by the processor, texture-based classification of the images.

In another aspect, the invention provides a portable imaging apparatus comprising: a light source configured to deliver multiple excitation wavelengths of light to excite a plurality of different fluorescent reporters that produce fluorescent light at two or more distinguishable wavelengths; a prism configured to direct light received through a lens onto a plurality of spatially-separated detectors such that said detectors can measure, in real-time, different emitted signals simultaneously; and a processor configured to process signals corresponding to the detected fluorescent light at the two or more distinguishable wavelengths to provide images of fluorescence of the two or more different fluorescent reporters within a subject.

In some embodiments, the light source comprises two or more lasers and/or a light engine. In some embodiments, the lens is a single axis optical lens. In some embodiments, the apparatus further comprises a multi-band filter positioned in front of the lens wherein the multi-band filter is configured to block any high power excitation light coming from the light source (and therefore the filter is tuned to the light engine laser light), but will be transparent for all other light (i.e. the visible light and all emission wavelengths of interest). In some embodiments, the apparatus comprises narrow band filters each positioned between the prism and a respective detector. In certain embodiments, the prism is a dichroic prism. In certain embodiments, the prism comprises at least two surfaces each having a different coating.

In another aspect, the invention is directed to an imaging apparatus, comprising: optics and a plurality of detectors for simultaneously receiving a plurality of signals, each signal corresponding to a unique fluorescent reporter within a subject (e.g., patient); a first signal pre-conditioning module for performing a first set of image processing operations on a first signal of the plurality of signals, the first signal corresponding to a first unique reporter (e.g., fluorescent reporter) within the subject; a second signal pre-conditioning module for performing the first set of image processing operations on a second signal of the plurality of signals, the second signal corresponding to a second unique reporter (e.g., fluorescent reporter) within the subject, wherein the first and second signal conditioning modules are configured to synchronously (e.g., simultaneously) perform image processing on their respective signals (e.g., configured to perform the operations at the same time; e.g., wherein each signal comprises a video stream and wherein each frame of the video stream is processed by both the first and second signal pre-conditioning device at the same time as each other, followed by the respective next video frames being processed at the same time as each other); optionally, a third and/or subsequent signal pre-conditioning modules for performing the first set of image processing operations on a third and/or subsequent signal of the plurality of signals, each signal corresponding to a unique reporter; and a monitor for displaying the processed signals (e.g., the signals may be further processed prior to display).

In certain embodiments, each of the first and second signal pre-conditioning modules (and, optionally, the third and/or subsequent signal pre-conditioning modules) is a member selected from the group consisting of a field programmable gate array, an application-specific integrated circuit, and a central processing unit. In certain embodiments, the first and second signal pre-conditioning modules (and, optionally, the third and/or subsequent signal pre-conditioning modules) exist on a single physical device. In certain embodiments, the first set of image processing operations comprises one or more members selected from the group consisting of fast Fourier transformation, discrete Fourier transformation, finite impulse response filtering, and infinite impulse response filtering.

In certain embodiments, the apparatus further comprises: a first signal post-conditioning module for performing a second set of image processing operations on the first signal; a second signal post-conditioning module for performing the second set of image processing operations on the second signal, wherein the first and second signal post-conditioning modules are configured to synchronously (e.g., simultaneously) perform image processing on their respective signals (e.g., configured to perform the operations at the same time; e.g., wherein each signal comprises a video stream and wherein each frame of the video stream is processed by both the first and second signal post-conditioning device at the same time as each other, followed by the respective next video frames being processed at the same time as each other); and, optionally, a third and/or subsequent signal post-conditioning module for performing the second set of image processing operations on a third and/or subsequent signal of the plurality of signals, wherein the second set of image processing operations comprises one or more members selected from the group consisting of scaling, interlacing chroma resampling, alpha blend mixing, color plane sequencing, frame buffering, test pattern generation, 2D media filtering, color space conversion, control synchronization, and frame reading.

In certain embodiments, each of the first and second signal post-conditioning modules (and, optionally the third and/or subsequent signal post-conditioning module(s)) is a member selected from the group consisting of a field programmable gate array, an application-specific integrated circuit, and a central processing unit. In certain embodiments, the first and second signal post-conditioning modules (and, optionally the third and/or subsequent signal post-conditioning module(s)) exist on a single board unit. In certain embodiments, the apparatus further comprises a multiplexing module configured to multiplex the first signal and second signal (e.g., as received, as pre-conditioned, or, preferably, as post-conditioned). In certain embodiments, the multiplexing module is additionally configured to multiplex the third and/or subsequent signals. In certain embodiments, the apparatus comprises a processor configured to retrieve (additional) data from a medical imaging data repository and graphically render the additional data with the multiplexed signals (e.g., superimpose and/or graphically augment the additional data with the multiplexed signals).

In certain embodiments, features described in Bradbury et al. *Integr. Biol.* (2013) 5:74-86, which is hereby incorporated herein by reference, may be used. In certain embodiments, features (e.g., probe species) described in Herz et al. *J. Mater. Chem.* (2009) 19:6341-6347, which is incorporated herein by reference, can be used.

In certain embodiments, features (e.g., nanoparticles) described in Bradbury et al., International PCT patent application numbers PCT/US2010/040994 and PCT/US2014/030401, published as WO2011/003109 on Jan. 6, 2011, and WO2014/145606 on Sep. 18, 2014, which are both hereby incorporated herein by reference in their entireties, can be used.

In some embodiments, features (e.g., post processing modules for deconvolution) described in Pauliah et al. *Magnetic Resonance Imaging* (2007), 25:1292-1299, which is incorporated herein by reference in its entirety, can be used.

Elements from embodiments of one aspect of the invention may be used in other aspects of the invention (e.g., elements of claims depending from one independent claim may be used to further specify embodiments of other independent claims). Other features and advantages of the invention will be apparent from the following figures, detailed description, and the claims.

The objects and features of the invention can be better understood with reference to the drawings described below, and the claims. In the drawings, like numerals are used to indicate like parts throughout the various views.

Definitions

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Peptide" or "Polypeptide": The term "peptide" or "polypeptide" refers to a string of at least two (e.g., at least three) amino acids linked together by peptide bonds. In some embodiments, a polypeptide comprises naturally-occurring amino acids; alternatively or additionally, in some embodiments, a polypeptide comprises one or more non-natural amino acids (i.e., compounds that do not occur in nature but that can be incorporated into a polypeptide chain; see, for example, http://www.cco.caltech.edu/~dadgrp/Unnatstruct-.gif, which displays structures of non-natural amino acids that have been successfully incorporated into functional ion channels) and/or amino acid analogs as are known in the art may alternatively be employed). In some embodiments, one or more of the amino acids in a protein may be modified, for example, by the addition of a chemical entity such as a carbohydrate group, a phosphate group, a farnesyl group, an isofarnesyl group, a fatty acid group, a linker for conjugation, functionalization, or other modification, etc.

"Contrast agent": The term "contrast agent" refers to a substance, molecule or compound used to enhance the visibility of structures or fluids in medical or biological imaging. The term "contrast agent" also refers to a contrast-producing molecule.

"Administration": The term "administration" refers to introducing a substance into a subject. In general, any route of administration may be utilized including, for example, parenteral (e.g., intravenous), oral, topical, subcutaneous, peritoneal, intra-arterial, inhalation, vaginal, rectal, nasal, introduction into the cerebrospinal fluid, or instillation into body compartments. In some embodiments, administration is oral. Additionally or alternatively, in some embodiments, administration is parenteral. In some embodiments, administration is intravenous.

"Biocompatible": The term "biocompatible", as used herein is intended to describe materials that do not elicit a substantial detrimental response in vivo. In certain embodiments, the materials are "biocompatible" if they are not toxic to cells. In certain embodiments, materials are "biocompatible" if their addition to cells in vitro results in less than or equal to 20% cell death, and/or their administration in vivo does not induce inflammation or other such adverse effects. In certain embodiments, materials are biodegradable.

"Biodegradable": As used herein, "biodegradable" materials are those that, when introduced into cells, are broken down by cellular machinery (e.g., enzymatic degradation) or by hydrolysis into components that cells can either reuse or dispose of without significant toxic effects on the cells. In certain embodiments, components generated by breakdown of a biodegradable material do not induce inflammation and/or other adverse effects in vivo. In some embodiments, biodegradable materials are enzymatically broken down. Alternatively or additionally, in some embodiments, biodegradable materials are broken down by hydrolysis. In some embodiments, biodegradable polymeric materials break down into their component polymers. In some embodiments, breakdown of biodegradable materials (including, for example, biodegradable polymeric materials) includes hydrolysis of ester bonds. In some embodiments, breakdown of materials (including, for example, biodegradable polymeric materials) includes cleavage of urethane linkages.

"Detector": As used herein, the term "detector" includes any detector of electromagnetic radiation including, but not limited to, CCD camera, photomultiplier tubes, photodiodes, and avalanche photodiodes.

"Sensor": As used herein, the term "sensor" includes any sensor of electromagnetic radiation including, but not limited to, CCD camera, photomultiplier tubes, photodiodes, and avalanche photodiodes, unless otherwise evident from the context.

"Image": The term "image", as used herein, is understood to mean a visual display or any data representation that may be interpreted for visual display. For example, a three-dimensional image may include a dataset of values of a given quantity that varies in three spatial dimensions. A three-dimensional image (e.g., a three-dimensional data representation) may be displayed in two-dimensions (e.g., on a two-dimensional screen, or on a two-dimensional printout). The term "image" may refer, for example, to an optical image, an x-ray image, an image generated by: positron emission tomography (PET), magnetic resonance, (MR) single photon emission computed tomography (SPECT), and/or ultrasound, and any combination of these.

"Substantially": As used herein, the term "substantially", and grammatic equivalents, refer to the qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result.

"Subject": As used herein, the term "subject" includes humans and mammals (e.g., mice, rats, pigs, cats, dogs, and horses). In many embodiments, subjects are be mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

Figures are presented herein for illustration purposes only, not for limitation.

BRIEF DESCRIPTION OF DRAWINGS

FIG. 1A depicts the injection of $^{124}$I-cRGDY-PEG-C dots about an oral cavity lesion with drainage to preauricular and submandibular nodes, in accordance with an embodiment of the present disclosure. FIG. 1B depicts a $^{124}$I-cRGDY-PEGylated core-shell silica nanoparticle (105, 115) with surface-bearing radiolabels and peptides and core-containing reactive dye molecules (110), in accordance with an embodiment of the present disclosure.

FIG. 4B depicts uptake of cRGDY-PEG-C dots into M21 cells (red puncta) with Hoechst counterstaining (blue), in accordance with an embodiment of the present disclosure.

FIG. 4C depicts LysoTracker Red labeling of acidic organelles (green puncta) with Hoechst counterstaining, in accordance with an embodiment of the present disclosure.

FIG. 4D depicts colocalization of cRGDY-PEG-C dots with LysoTracker Red staining (yellow puncta), in accordance with an embodiment of the present disclosure.

FIG. 4E depicts colocalization of cRGDY-PEG-C dots with FITC-dextran staining (yellow areas), in accordance with an embodiment of the present disclosure.

FIG. 6A depicts whole-body $^{18}$F-FDG PET-CT sagittal and axial views demonstrating primary tumor (dark arrow) and single SLN (white arrow) posteriorly within the right (Rt) neck after i.v. injection, in accordance with an embodiment of the present disclosure. FIG. 6B depicts a high-resolution PET-CT scan revealing bilateral nodes 1 hour after subdermal, 4-quadrant, peritumoral injection of $^{124}$I-cRGDY-PEG-C dots (SLN, arrow; left-sided node, arrowhead), in accordance with an embodiment of the present disclosure. FIGS. 6C and 6D are gross images of the cut surfaces of the black-pigmented SLN (asterisk, 6C) and contralateral metastatic node (arrowhead, 6D) in the left posterior neck. Imaged nodes were confirmed intraoperatively within the exposed surgical bed by visual inspection and γ-counting using hand-held PET devices prior to excision, in accordance with an embodiment of the present disclosure. FIG. 6E depicts a low-power view of H&E-stained SLN demonstrating scattered melanomatous clusters (white arrowhead), in accordance with an embodiment of the present disclosure. FIG. 6F depicts a corresponding high-power view of H&E-stained SLN, revealing melanoma cells (yellow arrowheads) and melanophages (white arrowhead), in accordance with an embodiment of the present disclosure. FIG. 6G shows a low-power image of a melanoma-specific marker, HMB-45 (white arrowhead), in representative SLN tissue, in accordance with an embodiment of the present disclosure. FIG. 6H depicts a high-power image of HMB-45-stained SLN tissue, in accordance with an embodiment of the present disclosure. FIG. 6I depicts a low-power view of H&E-stained contralateral lymph node showing scattered melanomatous clusters (arrowhead), in accordance with an embodiment of the present disclosure. FIG. 6J depicts a high-power image of contralateral node showing infiltration of melanomatous cells (arrowheads), in accordance with an embodiment of the present disclosure. FIG. 6K depicts a low-power image of representative normal porcine nodal tissue, in accordance with an embodiment of the present disclosure. FIG. 6L shows a high-power image of representative normal porcine nodal tissue, in accordance with an embodiment of the present disclosure.

FIGS. 7A and B depict axial CT images revealing a left pelvic soft tissue mass and left flank SLN, in accordance with an embodiment of the present disclosure. FIGS. 7C and D depict axial $^{18}$F-FDG PET images showing localized activity within the tumor (c, black arrow) and left flank SLN following i.v. tracer injection, in accordance with an embodiment of the present disclosure. FIG. 7E depicts an axial $^{124}$I-cRGDY-PEG-C dot co-registered PET-CT image showing site of local injection about the pelvic lesion. FIG. 7F shows a coronal $^{124}$I-cRGDY-PEG-C dot co-registered PET-CT image showing site of local injection about the pelvic lesion, in accordance with an embodiment of the present disclosure. FIG. 7G depicts is an axial coronal co-registered PET-CT image localizing activity to the SLN and including evidence of large bladder uptake, corresponding to FIG. 7E, in accordance with an embodiment of the present disclosure. FIG. 7H is a coronal co-registered PET-CT image localizing activity to the SLN and including evidence of large bladder uptake, corresponding to FIG. 7F, in accordance with an embodiment of the present disclosure. FIG. 7I depicts radioactivity levels of the primary tumor, SLN (in vivo, ex vivo), and a site remote from the primary tumor (i.e., background), using a handheld gamma probe, in accordance with an embodiment of the present disclosure.

FIG. 8A depicts RGB color (green) with local injection of Cy5.5-incorporated particles displayed in dual-channel model, in accordance with an embodiment of the present disclosure. FIG. 8B depicts NIR fluorescent channels (white) with local injection of Cy5.5-incorporated particles displayed in dual-channel model, in accordance with an embodiment of the present disclosure. FIGS. 8C-8F depict draining lymphatics distal to the site of injection, in accordance with an embodiment of the present disclosure. FIGS. 8G-8H depict images of the SLN displayed in the color and NIR channels, in accordance with an embodiment of the present disclosure. FIG. 8I depicts color image of the exposed SLN, in accordance with an embodiment of the present disclosure. FIGS. 8J-8M shows images of SLN in the color and NIR channels during (FIGS. 8J, 8K) and following (FIGS. 8I, 8M) excision, respectively, in accordance with an embodiment of the present disclosure. FIG. 8N depicts low power view of H&E stained SLN shows cluster of pigmented cells (black box) (bar=1 mm), in accordance with an embodiment of the present disclosure. FIG. 8O shows higher magnification of FIG. 8N, in accordance with an embodiment of the present disclosure. FIG. 8P shows low power view of HMB-45-stained (dark areas) SLN confirms presence of metastases (black box, bar=500 mm). FIG. 8Q depicts higher magnification in FIG. 8P reveals clusters of HMB-45+ expressing melanoma cells (bar=100 mm), in accordance with an embodiment of the present disclosure.

FIG. 9A depicts the axial CT scan of the $^{18}$F-FDG PET study shows calcification within the left posterior neck (yellow arrows), in accordance with an embodiment of the present disclosure. FIG. 9B shows the fused axial $^{18}$F-FDG PET-CT reveals hypermetabolic activity at this same site (arrows), in accordance with an embodiment of the present disclosure. FIGS. 9C and 9D depict the low and high-power views of H&E-stained calcified tissue demonstrate extensive infiltration of inflammatory cells, in accordance with an embodiment of the present disclosure. FIG. 9E shows the pre-injection axial CT scan of $^{124}$I-cRGDY-PEG-C dots shows calcified soft tissues within the posterior neck (arrows), in accordance with an embodiment of the present disclosure. FIG. 9F depicts the co-registered PET-CT shows no evident activity corresponding to calcified areas (arrow), but demonstrates a PET-avid node on the right (arrowhead), in accordance with an embodiment of the present disclosure. FIG. 9G depicts the axial CT at a more superior level shows nodes (arrowheads) bilaterally and a calcified focus (arrow), in accordance with an embodiment of the present disclosure. FIG. 9H depicts the fused PET-CT demonstrates PET-avid nodes (N) and lymphatic drainage (curved arrow). Calcification shows no activity (arrow), in accordance with an embodiment of the present disclosure. FIGS. 9I-9J depicts a high-power view to confirm the presence of nodal metastases, in accordance with an embodiment of the present disclosure. FIG. 9K depicts the single frame from a three-dimensional (3-D) PET image reconstruction shows multiple bilateral metastatic nodes (arrowheads) and lymphatic channels (solid arrow) draining injection site (white asterisk), in accordance with an embodiment of the present disclosure.

FIG. 10A depicts PET-CT fusion image (coronal view) shows no evident nodal metastases (asterisks), in accordance with an embodiment of the present disclosure. FIGS. 10B and 10C depict high-resolution PET-CT fusion images showing coronal and superior views, respectively, of bilateral metastatic nodes (open arrows) and lymphatic channels (curved arrows) within the neck following local injection of $^{124}$I-cRGDY-PEG-C dots, in accordance with an embodiment of the present disclosure.

FIG. 11A depicts the baseline coronal CT (white arrowhead), in accordance with an embodiment of the present disclosure. FIG. 11B depicts a PET (black arrowhead) and fused PET-CT image (white arrowhead) following a peritumoral injection, in accordance with an embodiment of the present disclosure. FIGS. 11C and 11D show combined PET-CT images showing a PET-avid lesion (white arrow) and $^{124}$I-cRGDYPEG-C dot flow within a draining lymphatic channel (asterisk) towards the SLN (curved arrow), in accordance with an embodiment of the present disclosure. FIGS. 11E and 11F depict pre-ablation axial CT images locate the SLN prior to RFA electrode placement into the node (below crosshairs), in accordance with an embodiment of the present disclosure. FIG. 11G shows that pre-ablation fused PET-CT reveals increased SLN activity (posterior to cross-hairs), in accordance with an embodiment of the present disclosure. FIG. 11H depicts that post-ablation PET-CT scan shows mildly reduced activity at the SLN site, anterior to the needle tip, in accordance with an embodiment of the present disclosure. FIG. 11I depicts corresponding pre-ablation H&E staining of core biopsy tissue from the SLN confirms pigmented tumor infiltration (bar=200 gm), in accordance with an embodiment of the present disclosure. FIG. 11J depicts high magnification of boxed area in FIG. 11I, in accordance with an embodiment of the present disclosure. FIG. 11K depicts post-ablation H&E staining shows necrotic changes within a partially tumor-infiltrated node (box) and multifocal hemorrhages (bar=500 gm), in accordance with an embodiment of the present disclosure. FIG. 11L shows high magnification of FIG. 11K, in accordance with an embodiment of the present disclosure. FIG. 11M depicts TUNEL staining of metastatic SLN before ablation (bar=20 gm), in accordance with an embodiment of the present disclosure. FIG. 11N depicts post-ablation TUNEL staining demonstrating focal areas of necrosis (dark area) with adjacent scattered tumor foci and normal nodal tissue (NT) (bar=500 gm), in accordance with an embodiment of the present disclosure. FIG. 11O depicts high magnification of boxed area in FIG. 11N, in accordance with an embodiment of the present disclosure.

FIG. 12A depicts axial neck CT image reveals a left-sided cutaneous soft tissue mass (arrow), in accordance with an embodiment of the present disclosure. FIG. 12B depicts co-registered axial PET-CT images show foci of increased activity at sites of local injection of the particle tracer, in accordance with an embodiment of the present disclosure. FIG. 12C depicts a CT image at a more proximal level to tumor reveals the SLN within the deep left neck soft tissues (arrow), in accordance with an embodiment of the present disclosure. FIG. 12D depicts a coregistered axial PET-CT image localizes activity to the node, in accordance with an embodiment of the present disclosure.

FIGS. 13A and 13B depict a dual-channel mode and Cy5.5 channel images of fluorescence signal (light area) extending from the injection site to the SLN within the main lymphatic channel after local injection of αMSH-PEG-Cy5.5-C'dots about the primary tumor site in a melanoma miniswine model, in accordance with an embodiment of the present disclosure. FIGS. 13C and 13E depict dual-channel mode images of the SLN, in accordance with an embodiment of the present disclosure. FIGS. 13D and 13F depict Cy5.5 channel images of the SLN, in accordance with an embodiment of the present disclosure. FIG. 13G depicts dual-channel images of excised, bisected node, in accordance with an embodiment of the present disclosure. FIG. 13H depicts Cy5.5-channel images of excised, bisected node, in accordance with an embodiment of the present disclosure. FIGS. 13I and 13J depict low- and high-power views, respectively, of the H&E stained SLN, in accordance with an embodiment of the present disclosure. FIGS. 13K and 13L depict low- and high-power views, respectively, of HMB45+ stained SLN, in accordance with an embodiment of the present disclosure. In the intraoperative suite, for the first time, a second melanoma-targeting particle probe, αMSH-PEG-Cy5.5-C'dots for mapping metastatic nodal disease was assessed in this miniswine model, in accordance with an embodiment of the present disclosure.

FIG. 14A depicts a composite image, in accordance with an embodiment of the present disclosure. FIG. 14B depicts a Cy5.5 image, in accordance with an embodiment of the present disclosure. FIG. 14C depicts a CW800 channel image of a downstream node, in accordance with an embodiment of the present disclosure. FIG. 14D depicts a histologic confirmation of melanoma by HMB45+ staining, in accordance with an embodiment of the present disclosure.

FIG. 16A shows an optical fiber cable 1600 with inner fiber bundles 1610 and outer fibers bundles 1605 in a ring-like setup, the inner fiber bundles 1610 having a smaller diameter than the outer fiber bundles 1605, in accordance with an embodiment of the present disclosure. FIG. 16B shows the combined fiber cable 1600 of FIG. 16A with attached to it a light module, in the current example an excitation light (e.g., laser or LED) module 1615, in accordance with an embodiment of the present disclosure. FIG. 16C shows a schematic of the assembly of three light engines 1620 and the beginning of cable 1625 thus form a combined light engine 1605, in accordance with an embodiment of the present disclosure. FIG. 16D shows a solid state laser modules 1630 can be coupled efficiently into a fiber bundle through either butt-coupling or a lens construction, in accordance with an embodiment of the present disclosure.

FIGS. 18A, 18B schematically show spectra in a light engine according to an embodiment of the present disclosure.

FIG. 19 schematically shows a ring light connected to light engines according to an embodiment of the present disclosure.

FIG. 41 depicts the camera and laparoscope attachments for the ArteMIS™ handheld imaging system, in accordance with an embodiment of the present disclosure.

FIG. 50 depicts a flowchart demonstrating features of the portable imaging apparatus, in accordance with an embodiment of the present disclosure.

DETAILED DESCRIPTION

Figure 2:
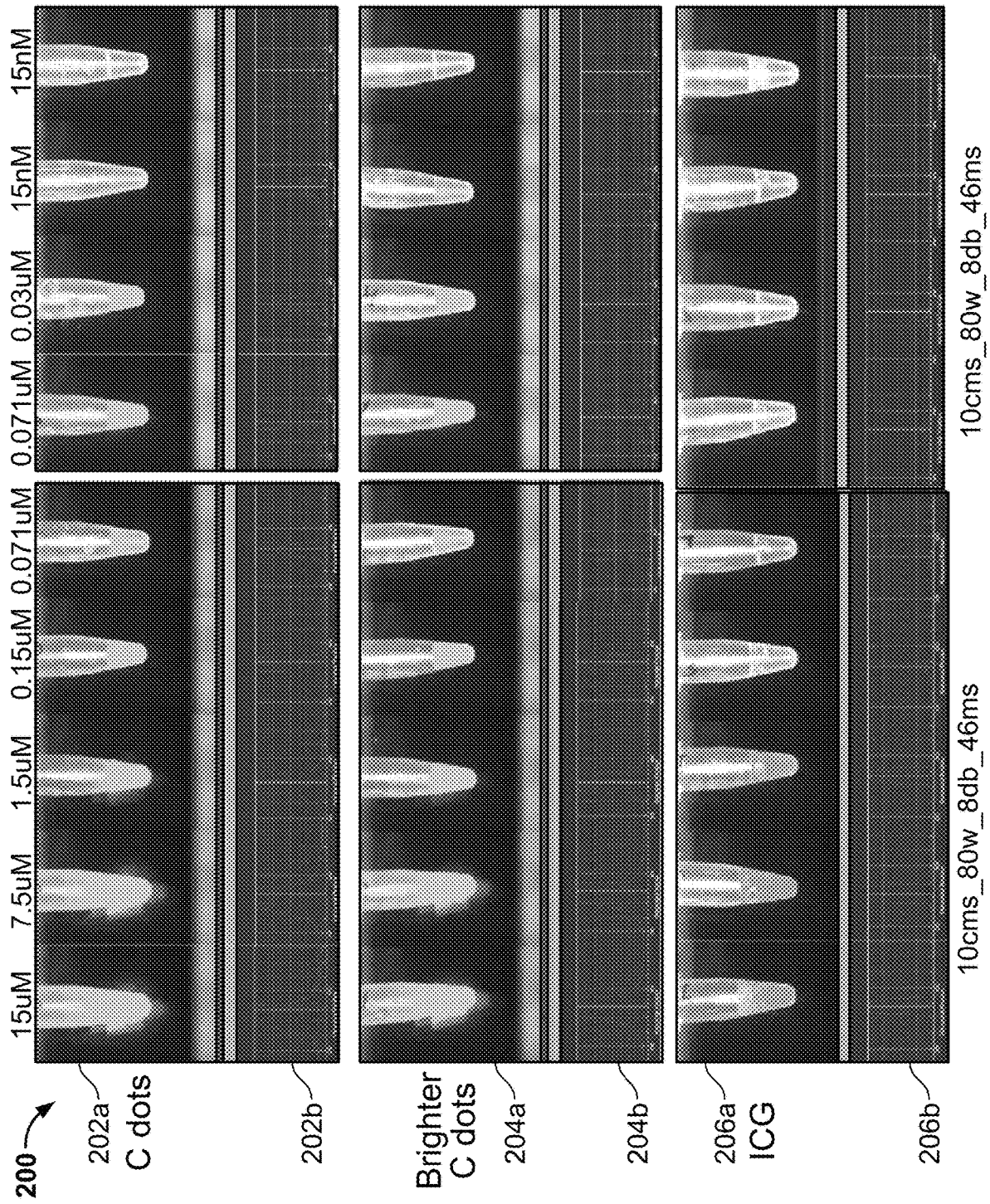
FIG. 2 depicts the fluorescence of C dots, C' dots (or brighter C dots), and ICG technology at 10 cm from the detector face of a camera system from concentration of 15 μM to 1.5 nM, in accordance with an embodiment of the present disclosure.

It is contemplated that methods, systems, and processes described herein encompass variations and adaptations developed using information from the embodiments described herein.

Throughout the description, where systems and compositions are described as having, including, or comprising specific components, or where processes and methods are described as having, including, or comprising specific steps, it is contemplated that, additionally, there are systems and compositions of the present embodiment that consist essentially of, or consist of, the recited components, and that there are processes and methods of the present embodiment that consist essentially of, or consist of, the recited processing steps.

The mention herein of any publication, for example, in the Background section (or elsewhere), is not an admission that the publication serves as prior art with respect to any of the claims presented herein. The Background section is presented for purposes of clarity and is not meant as a description of prior art with respect to any claim.

Headers are used herein to aid the reader and are not meant to limit the interpretation of the subject matter described.

Early detection of melanoma micrometastases in regional lymph nodes using sentinel lymph node (SLN) mapping and biopsy (SLNB) can potentially improve patient outcomes. Current SLNB technique has several limitations, including lack of intraoperative visual discrimination of the SLN from adjoining critical structures, including nerves and vessels. Newer generation, biocompatible particle imaging platforms as described herein can overcome these drawbacks for use in a variety of image-guided applications while selectively probing critical cancer targets. One such dual-modality optical-PET platform, a clinically-translated, integrin-targeting silica nanoparticle, meets a number of key design criteria when coupled with PET and portable, real-time optical camera systems. Its ability to discriminate metastatic disease from tissue inflammatory changes in melanoma models provides a more accurate and reliable modality for surgically-based or interventionally-driven therapies.

SLN mapping techniques, routinely used in staging melanoma, specifically identify the node/s that drain the primary tumor and are at highest risk of tumor metastases. The identification of lymph node metastases permits patients to be stratified to appropriate treatment arms in a more timely fashion, and can thereby potentially improve patient outcomes.

Non-invasive imaging methods, such as CT, MRI, positron emission tomography (PET), or combinations thereof, have been used to identify cancerous spread by screening for abnormally enlarged and/or metabolically active nodes. In the latter case, different tumor types demonstrate enhanced glucose metabolism and overexpression of glucose transporters (GLUTs); this is typically revealed using the glucose mimetic, 2-deoxy-2-[$^{18}$F]fluoro-D-glucose ($^{18}$F-FDG) (Kelloff, *Clin. Cancer Res.*, (2005)). However, $^{18}$F-FDG PET avidity is not specific or reliable, as nodal enlargement can be seen with inflammatory, infectious, or other metabolically active processes, and may co-exist with the spread of cancerous cells. Further, nodes smaller than a defined size threshold (i.e., 1.5 cm) may harbor micrometastases that are not evident by traditional $^{18}$F-FDG PET. Finally, an inability to translate sites of metastatic disease seen on these pre-operative planning studies into three-dimensional (3D) locations during the surgical procedure poses major challenges for intraoperative identification, precluding direct mapping of locoregional nodal distributions within an exposed nodal basin. For these reasons, a combination of these techniques along with newer cancer-targeted approaches has been developed to enable the translation of pre-operative findings to the operative field, facilitating SLN localization.

Standard-of-care SLN mapping techniques rely on the uptake of an imaging agent, injected about the primary tumor site, for transport to the SLN via one or more lymphatic channels (FIG. 1A). One such agent, filtered technetium-radiolabeled sulfur colloid (i.e., $^{99m}$Tc-sulfur colloid) is injected pre-operatively for SLN localization and visualized with a gamma camera co-registered to a CT scan for spatial orientation. Intraoperatively, a hand-held gamma probe is used to measure radioactivity in the draining lymphatic structures, and help the surgeon localize the SLN. SLN mapping with $^{99m}$Tc-sulfur colloid radiotracer is standard-of-care procedure for staging the regional nodal basin in early melanoma (~50 000 procedures per year in US). Another intraoperative adjunct for localizing SLNs is isosulfan (Lymphazurin 1%, US Surgical, North Haven, Conn.) or 'blue dye', which turns the SLN blue following injection into the peritumoral region and allows visual identification of a "hot and blue" SLN.

Current SLN mapping and biopsy techniques suffer from several drawbacks. Primarily, spatial resolution is low, offering no real-time visualization or detailed anatomy of nodes and lymphatic channels within the operative field. In addition, filtered $^{99m}$Tc-sulfur colloid particles, ranging in size from 10-100 nm, demonstrate slow clearance from the site of injection (i.e., interstitial space), which can effectively limit adequate visualization of the draining lymphatics.

Although the SLN may be radioactive and "hot" to the intraoperative gamma probe, the operating surgeon needs to rely principally on an abnormal visual appearance and palpation to discriminate the SLN and reliably differentiate it from adjoining tissues. If adjunctive blue dye injection is used, the blue SLN is apparent only if it is located superficially in the operative field and may not become apparent until significant amount of tissue dissection has taken place. Moreover, intraoperative identification of SLNs which can be 4-5 mm in size is fraught with the risk of injury to important adjacent structures such as nerves and vessels. Within certain areas of the body such as the head and neck, injury to neurovascular structures can result in dramatic consequences and can permanently alter functions such as speech and swallowing, and the cosmetic appearance of the patient. Within the head and neck, failure to identify any drainage pattern or localize small nodes occurs in up to ~10% of cases (Erman, *Cancer*, (2012)). Staging of head and neck melanomas has been hampered by unpredictable patterns of metastatic disease spread, difficult-to-detect nodes in anatomic proximity to tumor, and difficulty in intraoperative differentiation of small nodes from vital structures during surgery.

The limitations associated with standard-of-care SLN mapping techniques, along with innovations in contrast agent development and imaging technologies (i.e., optical, PET-CT, MRI), have spurred efforts to develop new tools for improving lymphatic imaging strategies and identify the SLN/s for biopsy. Traditional near-infrared (NIR) organic dyes (e.g., Cy7, Cy5.5) are frequently used to map the lymphatic system, but have associated drawbacks. Dyes are prone to extravasation into the surrounding tissues given their small size and require conjugation to macromolecules (i.e., proteins, immunoglobulins) for retention within the lymphatic system. Their reduced brightness and photostability decrease useful imaging penetration depths, and their relatively wide emission spectra can result in destructive spectral interference, precluding their use in multi-spectral imaging applications (Kobayashi, *Nano Lett.* (2007)). The FDA-approved NIR dye indocyanine green (ICG, emission peak 830 nm) is a commonly used fluorophore in clinical settings (Sevick-Muraca, *Radiology* (2008); Crane, *Gynecol. Oncol.* (2011)) to image lymphatic flow and SLN/s at very low doses (Sevick-Muraca, *Radiology* (2008)). However, the versatility of this agent is limited, and the absence of functional groups can make conjugation to targeting and/or contrast-producing moieties challenging (Rasmussen, *Curr. Opin. Biotechnol.* (2009)). Given the weak and unstable nature of this NIR dye, depth penetration is restricted, with detection largely confined to interrogation of superficial nodes.

Newer-generation molecular and particle-based agents, such as non-targeted activatable (Keereweer, *Arch. Otolaryngol.* (2011); Mahmood *Mol. Cancer. Ther.*, (2003); Wunderbaldinger, *Eur. Radiol.*, (2003)) and targeted organic fluorophores (Gleysteen, *Cancer Biol. Ther.* (2007); Lee, *Clin. Cancer Res.* (2008); Withrow, *Technol. Cancer Res. Treat.* (2008)), gadolinium labeled dendrimers (Koyama, *J. Magn. Reson. Imaging* (2007); Kobayashi, *J. Controlled Release* (2006); Lucarelli, *Lymphatic Res. Biol.* (2009)) and other nanocarriers (Jain, *J. Controlled Release* (2009)), and macromolecular agents (Wallace, *Ann. Surg. Oncol.* (2003); Hama, *Invest. Dermatol.* (2007); Povoski, *Surg. Innov.*, (2012)), have been developed for use with image-guided procedures. A detailed discussion of each of these classes of agents is discussed in the following Rasmussen, *Curr. Opin. Biotechnol.* (2009); Lucarelli, *Lymphatic Res. Biol.* (2009); Jain, *Nat. Rev. Clin. Oncol.* (2010); Keereweer, *Mol. Imaging Biol.*, (2011); Sampath, *Biomed. Opt.* (2008); Schroeder, *Nat. Rev. Cancer* (2012); Yudd, *Radiographics* (1999); Ravizzini, *Wiley Interdiscip. Rev.: Nanomed. Nanobiotechnol.* (2009); Khullar, *Semin. Thorac. Cardiovasc. Surg.* (2009). The more recent introduction of multimodal nanoparticles (Madru, *J. Nucl. Med.* (2012); Olson, *Proc. Natl. Acad. Sci. U.S.A.* (2010); Benezra, *J. Clin. Invest.* (2011)) for use with at least two imaging modalities can potentially improve lymph node resection efforts by aiding pre-operative planning and intraoperative guidance on the basis of a single platform technology. Such dual-modality agents, coupled with increasingly sensitive and higher resolution portable optical imaging devices permitting on-the-fly adjustments to mage quality during acquisition, enable real-time image-guided treatment to be placed under the direct control of the operating surgeon or interventionalist. Under these conditions, sites of disease on pre-operative imaging scans might be more readily translated into 3D locations within the exposed operative bed during surgical procedures. Confirmation of tissue fluorescence can be obtained by hand-held PET probes for gamma and/or beta ray detection. This set-up would further enable the surgeon to see metastatic SLN/s through overlying tissue in order to accurately delineate these node(s) from adjoining anatomy, thereby minimizing risk of injury to crucial structures such as blood vessels and nerves.

For lymphatic imaging, ideal imaging agents should exhibit key properties that improve SLN tissue localization and retention (i.e., surface receptor binding, internalization), enhance imaging signal at the target site, and promote more rapid clearance from the site of injection and the body in order to maximize target-to-background ratios (i.e., agent should target and clear). The need to minimize normal-tissue radiation dose is a further consideration for radiotracers. For mapping lymphatic tumor spread using particle-based agents, key design constraints need to be met to achieve maximum diagnostic/therapeutic benefit while minimizing associated complications (i.e., injury to adjacent critical structures, lymphedema).

Applications for Imaging Abnormalities and Diseases

Described herein is an in vivo imaging method for selectively imaging a subject containing two or more probe species simultaneously, wherein two or more probe species are administered to a subject, either at the same time or sequentially. In some embodiments, the probes are introduced into the subject, either by injection of a combined probe species, or by injection of separate probe species. In some embodiments, because the pharmacokinetics (PK) of the probes and substrate may be different, these injections may need to be performed at different times. In some embodiments, the probe species can be any combination of fluorescent or other imaging agents. In some embodiments, a probe species comprises a silica-based nanoparticle containing one or more fluorescent dyes. A single probe species may serve as both an optical and other imaging modality agent, e.g., dual imaging agent. The method therefore allows the recording of multiple biological processes, functions or targets simultaneously. In some embodiments, the methods are used to determine a number of indicia, including tracking the localization of the probe species in the subject over time or assessing changes or alterations in the metabolism and/or excretion of the imaging probes in the subject over time. The methods can also be used to follow therapy for such diseases by imaging molecular events and biological pathways modulated by such therapy, including but not limited to determining efficacy, optimal timing, optimal dosing levels (including for individual patients or test subjects), pharmacodynamic parameters, and synergistic effects of combinations of therapy.

The methods and systems described herein can be used with other imaging approaches such as the use of devices including but not limited to various scopes (microscopes, endoscopes), catheters and optical imaging equipment, for example computer based hardware for tomographic presentations.

Embodiments can be used, for example, to help a physician, surgeon, or other medical personnel or researcher to identify and characterize areas of disease, such as arthritis, cancers, metastases or vulnerable or unstable plaque, to distinguish diseased and normal tissue, such as detecting tumor margins that are difficult to detect.

In certain embodiments, the methods can be used in the detection, characterization and/or determination of the localization of a disease, especially early disease, the severity of a disease or a disease-associated condition, the staging of a disease, and monitoring and guiding various therapeutic interventions, such as surgical procedures, and monitoring and/or development of drug therapy and delivery, including cell based therapies. In some embodiments, the methods can also be used in prognosis of a disease or disease condition. With respect to each of the foregoing, examples of such disease or disease conditions that can be detected or monitored (before, during or after therapy) include inflammation (for example, inflammation caused by arthritis, for example, rheumatoid arthritis), cancer (for example, colorectal, ovarian, lung, breast, prostate, cervical, testicular, skin, brain, gastrointestinal, pancreatic, liver, kidney, bladder, stomach, leukemia, mouth, esophageal, bone, including metastases), cardiovascular disease (for example, atherosclerosis and inflammatory conditions of blood vessels, ischemia, stroke, thrombosis, disseminated intravascular coagulation), dermatologic disease (for example, Kaposi's Sarcoma, psoriasis, allergic dermatitis), ophthalmic disease (for example, macular degeneration, diabetic retinopathy), infectious disease (for example, bacterial, viral, fungal and parasitic infections, including Acquired Immunodeficiency Syndrome, Malaria, Chagas Disease, Schistosomiasis), immunologic disease (for example, an autoimmune disorder, lymphoma, multiple sclerosis, rheumatoid arthritis, diabetes mellitus, lupus erythematosis, myasthenia gravis, Graves disease), central nervous system disease (for example, a neurodegenerative disease, such as Parkinson's disease or Alzheimer's disease, Huntington's Disease, amyotrophic lateral sclerosis, prion disease), inherited diseases, metabolic diseases, environmental diseases (for example, lead, mercury and radioactive poisoning, skin cancer), bone-related disease (for example, osteoporosis, primary and metastatic bone tumors, osteoarthritis), neurodegenerative disease, and surgery-related complications (such as graft rejection, organ rejection, alterations in wound healing, fibrosis or other complications related to surgical implants). In some embodiments, the methods can therefore be used, for example, to determine the presence of tumor cells and localization and metastases of tumor cells, the presence and localization of inflammation, including the presence of activated macrophages, for instance in atherosclerosis or arthritis, the presence and localization of vascular disease including areas at risk for acute occlusion (e.g., vulnerable plaques) in coronary and peripheral arteries, regions of expanding aneurysms, unstable plaque in carotid arteries, and ischemic areas, and stent thrombosis. The methods and compositions of the embodiments can also be used in identification and evaluation of cell death, injury, apoptosis, necrosis, hypoxia and angiogenesis. The methods and compositions of the embodiments can also be used in for monitoring trafficking and localization of certain cell types, including T-cells, tumor cells, immune cells, stem cells, and other cell types. In particular, this method may be used to monitor cell based therapies. The methods and compositions of the embodiments can also be used as part of photodynamic therapy, including imaging, photoactivation and therapy monitoring.

In some embodiments, the methods and systems are used to evaluate sentinel lymph nodes in metastatic melanoma by visualizing different tumor lymphatic drainage pathways and nodal distributions following local injection. Simultaneous multicolor platforms can be visualized in real-time using the handheld Artemis fluorescence camera system. Real-time optical imaging using the Artemis™ handheld fluorescent camera system can be used, along with different NIR dye-containing silica nanoparticles, to simultaneously map different nodal distributions in a clinically relevant larger-animal (miniswine) metastatic melanoma model. After locally injecting these different dye-containing particle batches about more than one primary cutaneous lesion, both anatomic (i.e., nodal localization/retention) and functional (i.e., abnormal lymphatic flow, time to detection post-injection) information will be acquired simultaneously. The different dye-containing particles can be mixed together and co-injected—the system described herein allows graphical differentiation of the different particles, detected simultaneously. In the clinical setting, such information can be used to localize all sites of nodal disease, as well as abnormal lymphatic flow, in order to guide subsequent treatment planning. It is also possible, for example, to map different surface receptors on melanoma or other tumor types using two (or more) particle batches; each batch contains particles that bear different peptide ligands and dyes. The ability to exploit the use of these visualization tools (i.e., different NIR dye-containing NPs & multichannel fluorescence camera system) for enhanced SLN localization offers a distinct advantage over imaging approaches without optical guidance, and is expected to improve disease staging and patient outcome measures.

In some embodiments, the methods and systems are performed/used to visualize intraoperatively in real-time peripheral nerves and nodal disease in prostate cancer and other cancers (e.g., melanoma, and cervical/uterine/ovarian cancers) using targeted dual-modality silica nanoparticles. Intraoperative visualization and detection tools will improve post-surgical outcomes in prostate cancer patients, enabling complete tumor resection without functional damage to adjacent neuromuscular structures (i.e., nerves). To achieve this end, translatable, dual-modality silica nanoparticles (NPs) can improve targeted disease localization pre-operatively, as well as enhance real-time visualization of prostatic nerves, nodal disease, and residual prostatic tumor foci or surgical margins using a handheld NIR fluorescence camera system. Different dye-containing particle batches can be synthesized and characterized; each batch containing a different NIR dye and surface-bearing peptide for targeting tumor or for binding surrounding neural structures not visible to the naked eye. For example, ligands that can be used to target melanoma include cRGDY and α-MSH (melanocyte stimulating hormone), each attached to different dye-containing particles. Also, for example, integrin-targeting nanoparticles, e.g., cRGDY-PEG-C dots, specifically bind to integrin-expressing human cancer cell lines, and α-MSH binds a distinctly different receptor on human melanoma cells, melanocortin-1 (MICR), in vitro and in vivo.

FIGS. 1A and 1B depict a schematic of SLN mapping in the head and neck using $^{124}$I-cRGDY-PEG-C dots, in accordance with an embodiment of the present disclosure. FIG. 1A depicts the injection of $^{124}$I-cRGDY-PEG-C dots about an oral cavity lesion with drainage to preauricular and submandibular nodes. FIG. 1B depicts a $^{124}$I-cRGDY-PEGylated core-shell silica nanoparticle (105, 115) with surface-bearing radiolabels and peptides and core-containing reactive dye molecules (110). Tumor-targeting particles can be evaluated in vitro to determine cellular uptake kinetics in several different cancer cell lines, as against native ligand controls. To simultaneously image both tumor and surrounding nerves intraoperatively, serial tumor targeting and nerve binding affinity studies can be conducted in murine xenograft or miniswine models using the Artemis system, and following intravenous (i.v.) co-injection of the respective targeted NPs. Results can be compared with controls (i.e., peptides alone or non-targeting NPs). Pharmacokinetic assessments can also be conducted. On the basis of such optical studies, tumor-to-background and nerve-to-muscle ratios can be evaluated.

In some embodiments, the methods and systems can be used to intraoperatively evaluate in real-time residual disease in prostate cancer using dual-modality silica nanoparticles surface modified with multiple cancer directed ligands. Particle probes that selectively target different surface biomarkers on prostate cancer cells may lead to enhanced detection and/or more accurate staging of disease, while addressing issues of marker variability. The C dot platform can be exploited, for example, as follows: (1) attach each of two targeting ligands (J591 F(ab')2 or GRPr antagonist) to individual batches of different NIR dye-containing particles (i.e., one targeting ligand per particle batch) and (2) co-inject i.v. to assess receptor co-expression in prostate xenograft models using the high sensitivity Artemis camera system to improve disease mapping and complete tumor resection. A well-established cell surface antigen expressed by all prostate cancers, which can enhance tumor detection and localization of residual disease is PSMA, whose expression levels progressively increase in more poorly differentiated, metastatic and hormone-refractory cancers. The J591 mAb is reactive to a distinct extracellular epitope of PSMA, and has been clinically validated for use in tumor-targeted cancer detection and treatment. Another attractive and clinically-validated surface target for imaging prostate cancer is the gastrin-releasing peptide receptor (GRPr). GRPr overexpression has been observed in several malignant tumor types, but most consistently in prostate cancer. By contrast, normal and hyperplastic prostate tissue demonstrate no or very low binding of GRP. Radiolabeled GRPr antagonists have been used for imaging and radiotherapy of prostate cancer. Previous clinical studies using the foregoing radiolabeled ligands and PET imaging have shown that prostate cancer can be imaged in patients with high contrast. Furthermore, targeting of PSMA and GRPr is likely to be complementary, since PSMA is negatively regulated by androgen signaling whereas GRPr expression is increased by androgen signaling.

Imaging with Probe Species (Fluorescent Species)

The systems and methods described herein can be used with systems and methods described in U.S. patent application Ser. No. 13/381,209, published as US 2013/0039848 on Feb. 14, 2013, which relates to in vivo imaging systems and methods employing a fluorescent silica-based nanoparticle, and is incorporated by reference. In some embodiments, at least one of the probe species comprises nanoparticles. In some embodiments, the nanoparticles have a silica architecture and dye-rich core. In some embodiments, the dye rich core comprises a fluorescent reporter. In some embodiments, the fluorescent reporter is a near infrared or far red dye. In some embodiments, the fluorescent reporter is selected from the group consisting of a fluorophore, fluorochrome, dye, pigment, fluorescent transition metal, and fluorescent protein. In some embodiments, the fluorescent reporter is selected from the group consisting of Cy5, Cy5.5, Cy2, FITC, TRITC, Cy7, FAM, Cy3, Cy3.5, Texas Red, ROX, HEX, JA133, AlexaFluor 488, AlexaFluor 546, AlexaFluor 633, AlexaFluor 555, AlexaFluor 647, DAPI, TMR, R6G, GFP, enhanced GFP, CFP, ECFP, YFP, Citrine, Venus, YPet, CyPet, AMCA, Spectrum Green, Spectrum Orange, Spectrum Aqua, Lissamine and Europium.

The imaging system and method can be used with a number of different fluorescent probe species (or, as in embodiments using a tandem bioluminescent reporter/fluorescent probe, the fluorescent species thereof), for example, (1) probes that become activated after target contact (e.g., binding or interaction) (Weissleder et al., *Nature Biotech.*, 17:375-378, 1999; Bremer et al., *Nature Med.*, 7:743-748, 2001; Campo et al., *Photochem. Photobiol.* 83:958-965, 2007); (2) wavelength shifting beacons (Tyagi et al., *Nat. Biotechnol.*, 18:1191-1196, 2000); (3) multicolor (e.g., fluorescent) probes (Tyagi et al., *Nat. Biotechnol.*, 16:49-53, 1998); (4) probes that have high binding affinity to targets, e.g., that remain within a target region while non-specific probes are cleared from the body (Achilefu et al., *Invest. Radiol.*, 35:479-485, 2000; Becker et al., *Nature Biotech.* 19:327-331, 2001; Bujai et al., *J. Biomed. Opt.* 6:122-133, 2001; Ballou et al. *Biotechnol. Prog.* 13:649-658, 1997; and Neri et al., *Nature Biotech* 15:1271-1275, 1997); (5) quantum dot or nanoparticle-based imaging probes, including multivalent imaging probes, and fluorescent quantum dots such as amine T2 MP EviTags® (Evident Technologies) or Qdot® Nanocrystals (Invitrogen™); (6) non-specific imaging probes e.g., indocyanine green, AngioSense® (VisEn Medical); (7) labeled cells (e.g., such as cells labeled using exogenous fluorophores such as VivoTag™ 680, nanoparticles, or quantum dots, or by genetically manipulating cells to express fluorescent or luminescent proteins such as green or red fluorescent protein; and/or (8) X-ray, MR, ultrasound, PET or SPECT contrast agents such as gadolinium, metal oxide nanoparticles, X-ray contrast agents including iodine based imaging agents, or radioisotopic form of metals such as copper, gallium, indium, technetium, yttrium, and lutetium including, without limitation, 99m-Tc, 111-In, 64-Cu, 67-Ga, 186-Re, 188-Re, 153-Sm, 177-Lu, and 67-Cu. The relevant text of the above-referenced documents are incorporated by reference herein. Another group of suitable imaging probes are lanthanide metal-ligand probes. Fluorescent lanthanide metals include europium and terbium. Fluorescence properties of lanthanides are described in Lackowicz, 1999, Principles of Fluorescence Spectroscopy, $2^{nd}$ Ed., Kluwar Academic, New York, the relevant text incorporated by reference herein. In the methods of this embodiment, the imaging probes can be administered systemically or locally by injecting an imaging probe or by topical or other local administration routes, such as "spraying". Furthermore, imaging probes used in the embodiment of this invention can be conjugated to molecules capable of eliciting photodynamic therapy. These include, but are not limited to, Photofrin, Lutrin, Antrin, aminolevulinic acid, hypericin, benzoporphyrin derivative, and select porphyrins.

In general, fluorescent quantum dots used in the practice of the elements of this invention are nanocrystals containing several atoms of a semiconductor material (including but not limited to those containing cadmium and selenium, sulfide, or tellurium; zinc sulfide, indium-antimony, lead selenide, gallium arsenide, and silica or ormosil), which have been coated with zinc sulfide to improve the properties of the fluorescent agents.

In particular, fluorescent probe species are a preferred type of imaging probe. A fluorescent probe species is a fluorescent probe that is targeted to a biomarker, molecular structure or biomolecule, such as a cell-surface receptor or antigen, an enzyme within a cell, or a specific nucleic acid, e.g., DNA, to which the probe hybridizes. Biomolecules that can be targeted by fluorescent imaging probes include, for example, antibodies, proteins, glycoproteins, cell receptors, neurotransmitters, integrins, growth factors, cytokines, lymphokines, lectins, selectins, toxins, carbohydrates, internalizing receptors, enzyme, proteases, viruses, microorganisms, and bacteria.

In certain embodiments, probe species have excitation and emission wavelengths in the red and near infrared spectrum, e.g., in the range 550-1300 or 400-1300 nm or from about 440 to about 1100 nm, from about 550 to about 800 nm, or from about 600 to about 900 nm. Use of this portion of the electromagnetic spectrum maximizes tissue penetration and minimizes absorption by physiologically abundant absorbers such as hemoglobin (<650 nm) and water (>1200 nm). Probe species with excitation and emission wavelengths in other spectrums, such as the visible and ultraviolet light spectrum, can also be employed in the methods of the embodiments of the present invention. In particular, fluorophores such as certain carbocyanine or polymethine fluorescent fluorochromes or dyes can be used to construct optical imaging agents, e.g. U.S. Pat. No. 6,747,159 to Caputo et al. (2004); U.S. Pat. No. 6,448,008 to Caputo et al. (2002); U.S. Pat. No. 6,136,612 to Della Ciana et al. (2000); U.S. Pat. No. 4,981,977 to Southwick, et al. (1991); 5,268,486 to Waggoner et al. (1993); U.S. Pat. No. 5,569,587 to Waggoner (1996); 5,569,766 to Waggoner et al. (1996); U.S. Pat. No. 5,486,616 to Waggoner et al. (1996); U.S. Pat. No. 5,627,027 to Waggoner (1997); U.S. Pat. No. 5,808,044 to Brush, et al. (1998); U.S. Pat. No. 5,877,310 to Reddington, et al. (1999); U.S. Pat. No. 6,002,003 to Shen, et al. (1999); U.S. Pat. No. 6,004,536 to Leung et al. (1999); U.S. Pat. No. 6,008,373 to Waggoner, et al. (1999); U.S. Pat. No. 6,043,025 to Minden, et al. (2000); U.S. Pat. No. 6,127,134 to Minden, et al. (2000); U.S. Pat. No. 6,130,094 to Waggoner, et al. (2000); U.S. Pat. No. 6,133,445 to Waggoner, et al. (2000); U.S. Pat. No. 7,445,767 to Licha, et al. (2008); U.S. Pat. No. 6,534,041 to Licha et al. (2003); U.S. Pat. No. 7,547,721 to Miwa et al. (2009); U.S. Pat. No. 7,488,468 to Miwa et al. (2009); U.S. Pat. No. 7,473,415 to Kawakami et al. (2003); also WO 96/17628, EP 0 796 111 B1, EP 1 181 940 B1, EP 0 988 060 B1, WO 98/47538, WO 00/16810, EP 1 113 822 B1, WO 01/43781, EP 1 237 583 A1, WO 03/074091, EP 1 480 683 B1, WO 06/072580, EP 1 833 513 A1, EP 1 679 082 A1, WO 97/40104, WO 99/51702, WO 01/21624, and EP 1 065 250 A1; and Tetrahedron Letters 41, 9185-88 (2000).

Exemplary fluorochromes for probe species include, for example, the following: Cy5.5, Cy5, Cy7.5 and Cy7 (GE® Healthcare); AlexaFluor660, AlexaFluor680, AlexaFluor790, and AlexaFluor750 (Invitrogen); VivoTag™ 680, VivoTag™-S680, VivoTag™-S750 (VisEn Medical); Dy677, Dy682, Dy752 and Dy780 (Dyomics®); DyLight® 547, and/or DyLight® 647 (Pierce); HiLyte Fluor™ 647, HiLyte Fluor™ 680, and HiLyte Fluor™ 750 (AnaSpec®); IRDye® 800CW, IRDye® 800RS, and IRDye® 700DX (Li-Cor®); ADS780WS, ADS830WS, and ADS832WS (American Dye Source); XenoLight CF™ 680, XenoLight CF™ 750, XenoLight CF™ 770, and XenoLight DiR (Caliper® Life Sciences); and Kodak® X-SIGHT® 650, Kodak® X-SIGHT 691, Kodak® X-SIGHT 751 (Carestream® Health).

Ligands Attached to the Nanoparticle

The number of ligands attached to the nanoparticle may range from about 1 to about 20, from about 2 to about 15, from about 3 to about 10, from about 1 to about 10, or from about 1 to about 6. The small number of the ligands attached to the nanoparticle helps maintain the hydrodynamic diameter of the present nanoparticle which meet the renal clearance cutoff size range. Hilderbrand et al., Near-infrared fluorescence: application to in vivo molecular imaging, Curr. Opin. Chem. Biol., 14:71-9, 2010. The number of ligands measured may be an average number of ligands attached to more than one nanoparticle. Alternatively, one nanoparticle may be measured to determine the number of ligands attached. The number of ligands attached to the nanoparticle can be measured by any suitable methods, which may or may not be related to the properties of the ligands. For example, the number of cRGD peptides bound to the particle may be estimated using FCS-based measurements of absolute particle concentrations and the starting concentration of the reagents for cRGD peptide. Average number of RGD peptides per nanoparticle and coupling efficiency of RGD to functionalized PEG groups can be assessed colorimetrically under alkaline conditions and Biuret spectrophotometric methods. The number of ligands attached to the nanoparticle may also be measured by nuclear magnetic resonance (NMR), optical imaging, assaying radioactivity, etc. The method can be readily determined by those of skill in the art.

In some embodiments, a therapeutic agent may be attached to the nanoparticle. The therapeutic agents include antibiotics, antimicrobials, antiproliferatives, antineoplastics, antioxidants, endothelial cell growth factors, thrombin inhibitors, immunosuppressants, anti-platelet aggregation agents, collagen synthesis inhibitors, therapeutic antibodies, nitric oxide donors, antisense oligonucleotides, wound healing agents, therapeutic gene transfer constructs, extracellular matrix components, vasodialators, thrombolytics, anti-metabolites, growth factor agonists, antimitotics, statin, steroids, steroidal and non-steroidal anti-inflammatory agents, angiotensin converting enzyme (ACE) inhibitors, free radical scavengers, PPAR-gamma agonists, small interfering RNA (siRNA), microRNA, and anti-cancer chemotherapeutic agents. The therapeutic agents encompassed by the present embodiment also include radionuclides, for example, $^{90}$Y, $^{131}$I and $^{177}$Lu. The therapeutic agent may be radiolabeled, such as labeled by binding to radiofluorine $^{18}$F.

The contrast agent may be directly conjugated to the nanoparticle. Alternatively, the contrast agent may be indirectly conjugated to the nanoparticle, by attaching to linkers or chelates. The chelate may be adapted to bind a radionuclide. The chelates that can be attached to the present nanoparticle may include, but are not limited to, 1,4,7,10-tetraazacyclododecane-1,4,7,10-tetraacetic acid (DOTA), diethylenetriaminepentaacetic (DTPA), desferrioxamine (DFO) and triethylenetetramine (TETA).

Characterization of Ligands (i.e. Detection Agents, Contrast Agents, etc.) Attached to Nanoparticles A contrast agent may be attached to the present nanoparticle for medical or biological imaging. The imaging techniques encompassed in some embodiments may include positron emission tomography (PET), single photon emission computed tomography (SPECT), computerized tomography (CT), magnetic resonance imaging (MRI), optical bioluminescence imaging, optical fluorescence imaging, and combinations thereof. In some embodiments, the contrast agent can be any molecule, substance or compound known in the art for PET, SPECT, CT, MRI, and optical imaging. The contrast agent may be radionuclides, radiometals, positron emitters, beta emitters, gamma emitters, alpha emitters, paramagnetic metal ions, and supraparamagnetic metal ions. The contrast agents include, but are not limited to, iodine, fluorine, Cu, Zr, Lu, At, Yt, Ga, In, Tc, Gd, Dy, Fe, Mn, Ba and $BaSO_4$. The radionuclides that may be used as the contrast agent attached to the nanoparticle of the present embodiment include, but are not limited to, $^{89}Zr$, $^{64}Cu$, $^{68}Ga$, $^{86}Y$, $^{124}I$ and $^{177}Lu$.

Suitable means for imaging, detecting, recording or measuring the present nanoparticles may also include, for example, a flow cytometer, a laser scanning cytometer, a fluorescence micro-plate reader, a fluorescence microscope, a confocal microscope, a bright-field microscope, a high content scanning system, and like devices. More than one imaging techniques may be used at the same time or consecutively to detect the present nanoparticles. In one embodiment, optical imaging is used as a sensitive, high-throughput screening tool to acquire multiple time points in the same subject, permitting semi-quantitative evaluations of tumor marker levels. This offsets the relatively decreased temporal resolution obtained with PET, although PET is needed to achieve adequate depth penetration for acquiring volumetric data, and to detect, quantitate, and monitor changes in receptor and/or other cellular marker levels as a means of assessing disease progression or improvement, as well as stratifying patients to suitable treatment protocols.

Cancer-Targeting, Dual Modality Core Shell Silica Nanoparticles

Fluorescent core-shell silica nanoparticles (Cornell or C dots, where C' refers to brighter C dots) (Burns, *Nano Lett.* (2009); Choi, *J. Biomed. Opt.* (2007)) were designed for use in nanomedicine applications, including SLN mapping. This particle technology was modified with small numbers of peptide ligands, cyclic arginine-glycine-aspartic acid-tyrosine (cRGDY), attached to short, particle-bound, methoxy-terminated polyethylene glycol chains (PEG~0.5 kDa) (Burns, *Chem. Soc. Rev.*, (2006)) to create a non-toxic, potent high affinity integrin-targeting probe (Benezra, *J. Clin. Invest.* (2011)). Peptide ligands were labeled with the positron-emitting radionuclide, iodine-124 ($^{124}I$), through the use of a tyrosine linker to create a dual-modality (optical-PET) platform, $^{124}I$-cRGDY-PEG-C dots, as shown in FIG. 1B. This platform technology is ideally suited for SLN mapping and other image-guided applications based on the following design considerations: (1) small size, with tunable radius down to 4.0 nm, for optimizing clearance profiles (Burns, *Nano Lett.* (2009)) and promoting more uniform delivery into nodes and other metastatic disease sites; (2) targeting peptides for tumor-selective uptake, accumulation, and retention in integrin-expressing tumors, including malignant melanoma cells and xenografts (Benezra, *J. Clin. Invest.* (2011)); (3) encapsulated organic dyes (i.e., Cy5.5; emission maxima, nm) for dramatically enhancing photophysical features, such as brightness (>200% relative to a free dye) and photostability relative to the parent dye in aqueous solutions; (4) PEG-coated surfaces for reducing non-specific uptake by the liver, spleen, bone marrow; and (5) versatility of the silica shell for permitting multiple functions to be combined as a single vehicle, creating highly functionalized particle platforms.

The results of utilizing this first FDA investigational new drug approved dual-modality silica particle (~6-7 nm diameter) for improving the detection and localization of SLN metastases, differentiating nodal tumor burden, and monitoring treatment response to image-guided ablation procedures in a well-established spontaneous melanoma miniswine model (Misfeldt, *Vet. Immunol. Immunopathol.* (1994)) using both PET and optical imaging approaches can be demonstrated. This inorganic platform, defining a distinct class of theranostic platforms for nanomedicine (Jokerst *Acc. Chem. Res.* (2011)), has recently been found to be safe in a first-in-human clinical trial in metastatic melanoma patients (Phillips, *Sci Transl Med* 29 Oct. 2014: Vol. 6, Issue 260, p. 260ra149). For these SLN mapping studies, pre-operative and intraoperative imaging findings were correlated with histologic and immunochemical assays to confirm the presence or absence of melanoma. The specificity of this platform, relative to the standard of-care radiotracer, $^{18}F$-FDG, for cancer staging and for discriminating metastatic disease from inflammatory processes can be demonstrated. Following local injection of this PET-optical particle probe about the primary tumor site in these miniswine models, it can be observed that pre-operative PET imaging findings for mapping metastatic disease can be successfully translated to the intraoperative setting using a state-of-the-art, high-resolution, hand-held fluorescent camera system, the ArteMIS™ system, for direct, real-time visualization of the draining tumor lymphatics and fluorescent SLNs. Optical localization of the particle was confirmed using a clinically-approved handheld PET probe (IntraMedical Imaging LLC, Los Angeles, Calif.) for detecting gamma emissions prior to lymph node resection. The results of these studies highlight key design criteria which are needed to achieve optimal tumor-localizing properties of this particle platform within metastatic nodes, accurately image the lymphatic system, and promote local and whole body clearance.

Design Considerations for Translatable Particle Platform Technologies Particle Size Particle size is one of the critical determinants of lymphatic uptake kinetics. Smaller particles should lead to a more rapid migration from the interstitial space into the lymphatic system. This property may enable delineation of a greater number of smaller caliber lymphatic channels, as well as produce higher contrast images A smaller particle size is an appealing feature for enhanced delivery of probes into tumor-bearing nodes, and might additionally extend the lower limit of nodal sizes that can be sensitively detected. However, particle sizes less than about 3 nm (including dyes) are prone to extravasation and nonspecific tissue dispersal, increasing background fluorescence and potentially prolonging retention within the interstitium (Burns, *Nano Lett.* (2009); Kobayashi, *ACS Nano* (2007); Ohnishi, *Mol. Imaging* (2005)). Furthermore, such small particles demonstrate enhanced rates of efflux from tumor-bearing tissues, reducing nodal retention. For increasingly larger particle sizes, slower physiologic transport within cancer-infiltrated tissues may hinder a more uniform diffusion of particles throughout the interstitium, although target selectivity may be increased (Jain, *Nat. Rev. Clin. Oncol.* (2010)).

Circulation Lifetimes and Clearance

The size of particle platforms will affect their circulation or residence half-times. Assuming a non-toxic platform, longer blood half-times (i.e. times less than 600 minutes) (Jain, *Nat. Rev. Clin. Oncol.* (2010)) may be needed to increase the potential for sensitively targeting metastatic disease and discriminating tumor burden within more solid, tumor-bearing nodes. For diagnostic studies, this consideration should be weighed against the need to promote more rapid whole body clearance, preferably through the kidneys. Ultrasmall particle-based platforms or macromolecular systems that meet effective renal glomerular filtration size cutoffs of 10 nm or less are desirable (Choi, *Proc. Natl. Acad. Sci. U.S.A.* (2011)). Particles larger than about 10 nm diameter will progressively accumulate in the liver, followed by eventual hepatobiliary excretion. While ultimately effective, this mode of clearance prolongs exposure to administered particle loads, increasing the potential for adverse effects or toxicity.

In some embodiments, after administration of the nanoparticle to a subject, blood residence half-time of the nanoparticle may range from about 2 hours to about 25 hours, from about 3 hours to about 15 hours, or from about 4 hours to about 10 hours. Tumor residence half-time of the nanoparticle after administration of the nanoparticle to a subject may range from about 5 hours to about 5 days, from about 10 hours to about 4 days, or from about 15 hours to about 3.5 days. The ratio of tumor residence half-time to blood residence half-time of the nanoparticle after administration of the nanoparticle to a subject may range from about 2 to about 30, from about 3 to about 20, or from about 4 to about 15. Renal clearance of the nanoparticle after administration of the nanoparticle to a subject may range from about 10% ID (initial dose) to about 100% ID in about 24 hours, from about 30% ID to about 80% ID in about 24 hours, or from about 40% ID to about 70% ID in about 24 hours. In one embodiment, after the nanoparticle is administrated to a subject, blood residence half-time of the nanoparticle ranges from about 2 hours to about 25 hours, tumor residence half-time of the nanoparticle ranges from about 5 hours to about 5 days, and renal clearance of the nanoparticle ranges from about 30% ID to about 80% ID in about 24 hours.

In preferred embodiments, when the nanoparticle is in the amount 100 times of the human dose equivalent are administered to a subject, substantially no anemia, weight loss, agitation, increased respiration, GI disturbance, abnormal behavior, neurological dysfunction, abnormalities in hematology, abnormalities in clinical chemistries, drug-related lesions in organ pathology, mortality, or combinations thereof, is observed in the subject in about 10 to 14 days.

Increased Sensitivity of C' Dots (Brighter C Dots).

Figure 3:
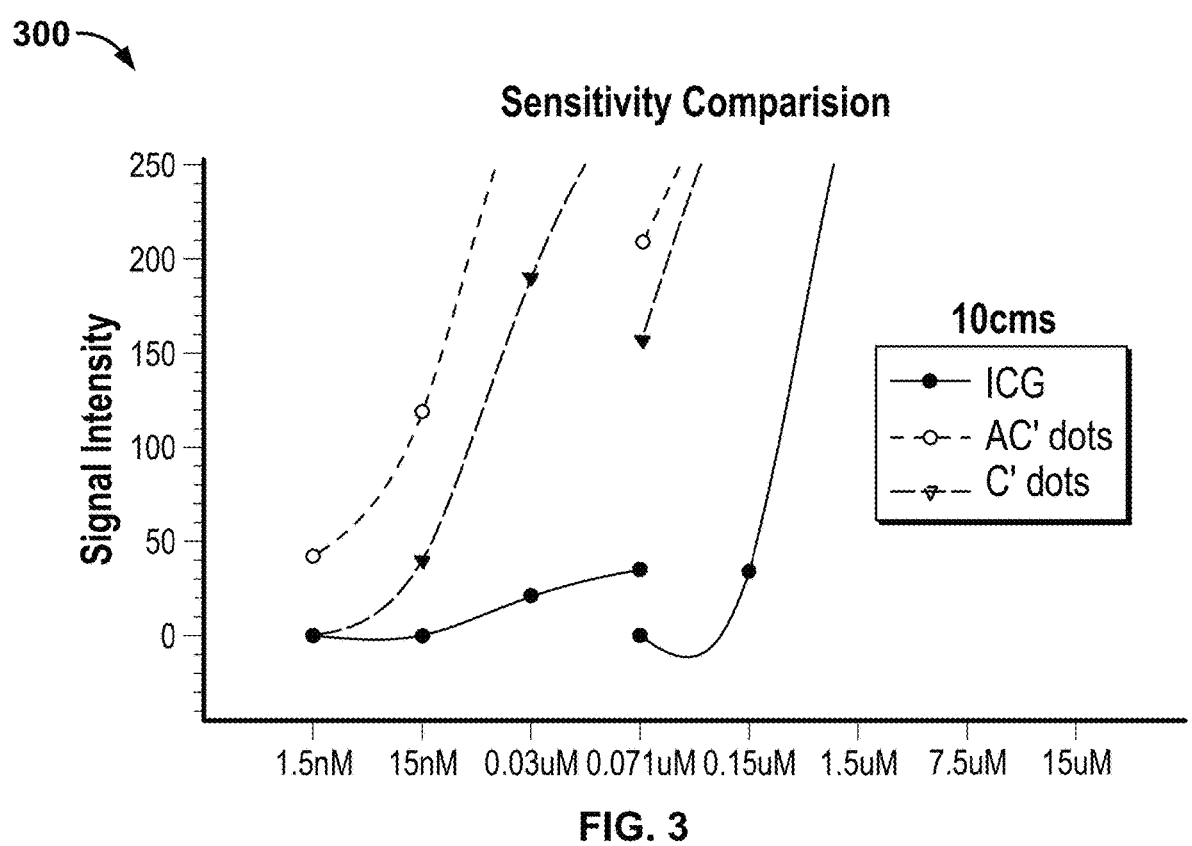
FIG. 3 depicts the fluorescence signal intensity versus concentration comparison of ICG, AC' dots (or C dots), and C' dots from 15 μM to 1.5 nM, in accordance with an embodiment of the present disclosure.

FIGS. 2 and 3 depict increased sensitivity of C dots and C' dots, described herein, compared to ICG (Indocyanine green) technology, a cyanine dye used in medical diagnostics. FIG. 2 depicts fluorescence of C dots (202*a, b*), brighter C dots (or C' dots) (204*a, b*), and ICG (206*a, b*) of varying concentrations from 10 cm from the detector face of the camera system. Table 1 lists values of the results depicted in FIGS. 2 and 3 and lists the dynamic range and sensitivity thresholds of brighter C dots (or C' dots), C dots, and ICG technology.

The maximum detection sensitivity at 10 cm from the detector face of the camera system of two different sized particles, 6 nm (C' dots) and 100 nm (ICG), can be described by the following calculations:

$$(1.5 \times 10^{-9} \text{ moles/liter})/(216 \text{ nm}^3 \times (10^{-9})^3 \text{ meter}^3) = 7 \times 10^{15} \text{ M/meter}^3 \text{ (brightest C dot)}$$

$$(10-18 \text{ moles/liter})/(10^6 \text{ nm}^3 \times (10^{-9})^3 \text{ meter}^3 = 1000 \text{ M/meter}^3 \text{ (typical larger size particle)}$$

C' dots, or the brighter C dots, yield a visible fluorescence signal in single nanomolar concentrations. The previous ICG technology requires much higher concentrations to achieve a visible signal, and the above measure of threshold signal intensity is many orders of magnitude greater for C' dots than for ICG.

TABLE 1

Comparison of detection sensitivities for C dots, C' dots, and ICG

| NIR Settings | Distance | Dilution Ratio | Concentration | C Prime Dots | C Dots | ICG |
| --- | --- | --- | --- | --- | --- | --- |
| 100 W_14 dB_80 ms | 10 cm | 1:10000 | 1.5 nM | 42 | 0 | 0 |
| 100 W_14 dB_80 ms | 10 cm | 1:1000 | 15 nM | 119 | 40 | 0 |
| 100 W_14 dB_80 ms | 10 cm | 1:500 | 0.03 uM | > | 190 | 21 |
| 100 W_14 dB_80 ms | 10 cm | 1:210 | 0.071 uM | > | > | 35 |
| 80 W_14 dB_46 ms | 10 cm | 1:210 | 0.071 uM | 206 | 154 | 0 |
| 80 W_14 dB_46 ms | 10 cm | 1:100 | 0.15 uM | > | > | 34 |
| 80 W_14 dB_46 ms | 10 cm | 1:10 | 1.5 uM | > | > | > |
| 80 W_14 dB_46 ms | 10 cm | 1:2 | 7.5 uM | > | > | > |
| 80 W_14 dB_46 ms | 10 cm | Non-diluted | 15 uM | > | > | > |

Cellular/Tissue Targeting and Uptake

Selectivity of most cancer-directed particle probes principally relies on the enhanced permeability and retention (EPR) effect (Jain, *Nat. Rev. Clin. Oncol.* (2010); Maeda, *J. Controlled Release*, (2000)), a passive solid tumor targeting process that results in preferential uptake and penetration of agents in tumor tissue relative to normal tissues. Longer circulation half-times are desirable to increase penetration. This property, found for many particle-based agents, promotes extravasation across more highly permeable tumor vasculature and effective diffusion through the tumor interstitium. Further, a number of critical tumor targets (e.g., cathepsins, vascular endothelial growth factor receptor, matrix metalloproteinases) known to be highly expressed by malignant cancer cells and the tumor microenvironment, as well as associated with key hallmarks of cancer (Hanahan, *Cell* (2000)), may serve to improve targeted detection of malignant cells and tissues using a variety of agents (i.e., peptides, antibodies and nanoparticles). Enhanced penetration and retention times have been observed for some of these targeted particle platforms relative to non-targeted particles (Jain, *Nat. Rev. Clin. Oncol.* (2010); Sugahara, *Cancer Cell* (2009); Karmali, *Nanomedicine* (2009)). Collectively, these properties enhance imaging detection sensitivity and specificity, and may permit discrimination of tumor-infiltrated nodal tissue from normal tissue (Ke, *Cancer Res.* (2003); Moon, *Bioconjugate Chem* (2003)) or other disease processes (inflammation, infection) that similarly manifest as nodal enlargement.

Figure 4A:
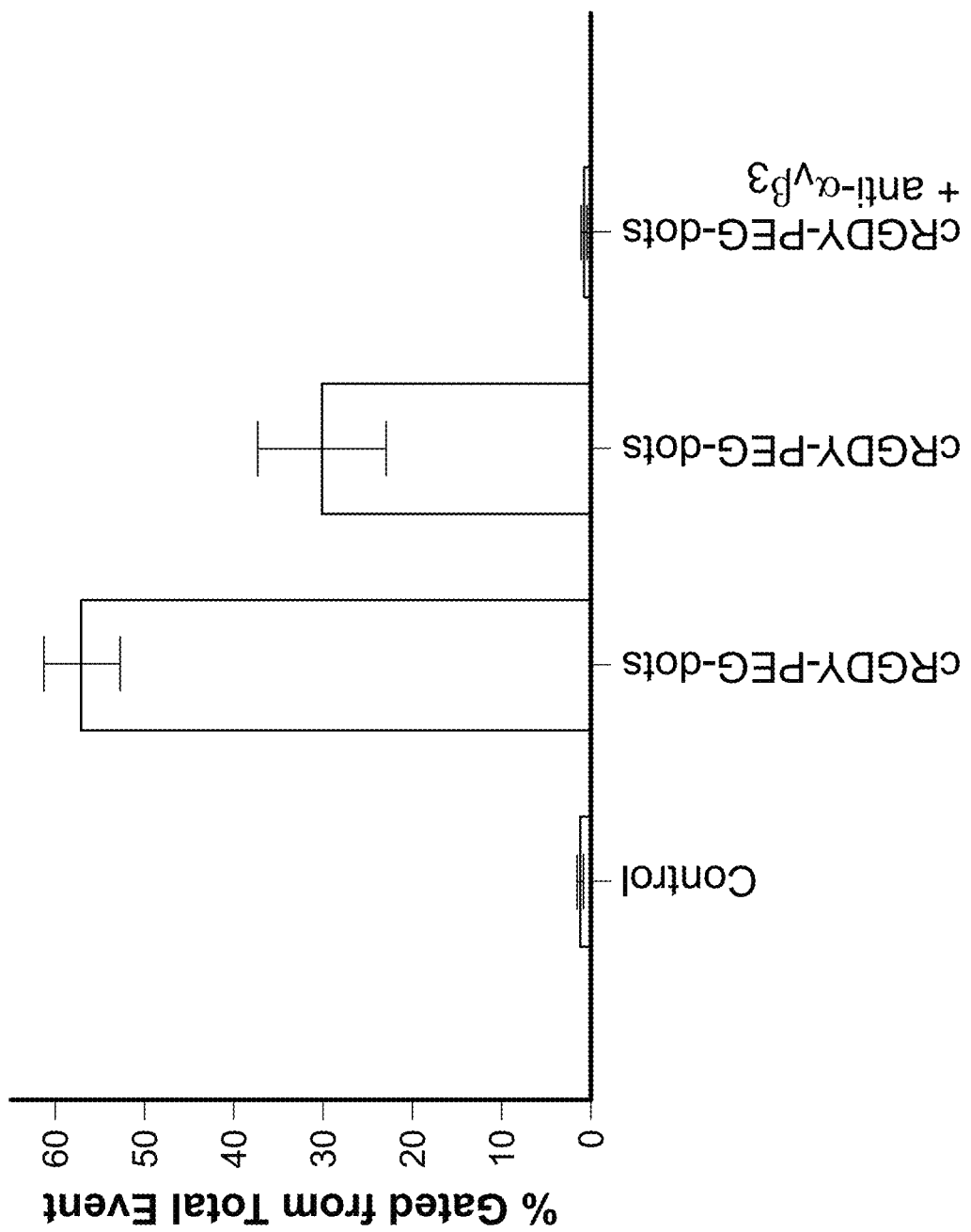
FIG. 4A depicts the specific binding and internalization of cRGDY-PEG-C dots in a human melanoma cell line (M21), in accordance with an embodiment of the present disclosure.

The aforementioned targets, as well as $\alpha_v\beta_3$ integrin, the target used in the studies presented herein, and whose overexpression promotes sustained angiogenesis, can be identified using small surface-bound ligands which specifically recognize and bind to tumor neovasculature and cancer cells. FIG. 4A depicts the specific binding and internalization of cRGDY-PEG-C dots in a human melanoma cell line (M21), in accordance with an embodiment of the present disclosure. FIG. 4A depicts the specific binding of cRGDY-PEG-C dots to M21 cells and $\alpha_v\beta_3$-integrin receptor blocking by flow cytometry using an anti-$\alpha_v\beta_3$ antibody before particle probe incubation, in accordance with an embodiment of the present disclosure. Non-specific binding using media alone and a scrambled peptide-bound construct, cRADY-PEG-dots (controls) is shown. (Adapted from: *Clin. Invest.*, (2011) 121, p. 2768-2780) FIGS. 4B-4D depict cRGDY-PEG-C dots colocalizing with endosomal and macropinocytosis markers using confocal microscopy. FIG. 4B depicts uptake of cRGDY-PEG-C dots into M21 cells (red puncta) with Hoechst counterstaining (blue), in accordance with an embodiment of the present disclosure.

The cRGDY-PEG-C dots highly bind to integrin surface receptors of M21 human melanoma cells by flow cytometry as shown in FIG. 4A. Thus, the particle and persistent imaging signal in M21 xenografts are retained. (Benezra, *J. Clin. Invest.* (2011)). In vitro assays completely block the receptor-mediated binding using anti-$\alpha_v\beta_3$ integrin antibody as depicted in FIG. 4A. FIG. 4A also shows that along with surface binding, the internalization of integrin-targeting agents via receptor-mediated endocytosis or other internalization gateway has been observed in M21 and other $\alpha_v\beta_3$ integrin positive tumor cells (Kossodo, *Mol. Imaging Biol* (2010)), leading to slower probe clearance and net tumor accumulation relative to surrounding tissues.

The biological compartments involved in cRGDY-PEG-C dot internalization are identified by colocalization assays in M21 cells with cRGDY-PEG-C dots and biomarkers of different endocytotic vesicles. FIG. 4B shows the internalization of the targeted particle (~1 micromolar, red, 4-hr incubation) is sensitively detected by an inverted confocal microscope (Leica TCS SP2 AOBS) equipped with a HCX PL APO objective (63×1.2NA Water DIC D). FIG. 4C depicts LysoTracker Red labeling of acidic organelles (green puncta) with Hoechst counterstaining, in accordance with an embodiment of the present disclosure. Using endocytotic markers LysoTracker Red (100 nM, green) and transferrin-Alexa488 shown in FIG. 4C confirm the uptake into acidic endocytic structures, with the latter suggesting clathrin-dependent pathway activity (Potocky, *J. Biol. Chem.* (2003)) and gradual acidification of vesicles. FIG. 4D depicts colocalization of cRGDY-PEG-C dots with LysoTracker Red staining (yellow puncta) and FIG. 4E depicts colocalization of cRGDY-PEG-C dots with FITC-dextran staining (yellow areas), in accordance with an embodiment of the present disclosure. Magnification of the images are 63×. FIG. 4D shows colocalization data between the particle and acidic endocytic vesicles (yellow puncta). FIG. 4E also shows the observed uptake into macropinocytes using 70 kDa dextran-FITC (Potocky, *J. Biol. Chem.* (2003); Wadia, *Nat. Med.* (2004)) (1 mg mL-1), which co-localized with cRGDY-PEG-C dots; this finding, seen as yellow puncta, indicates a second pathway of internalization. Nuclear counterstaining (blue) was done with Hoechst 33258 (0.01 mg mL$^{-1}$). No particles entered the nucleus. Surface-bound particles are additionally noted and are depicted in FIG. 4E (red).

Surface Charge

Surface charge can affect the transport properties of particles across the vasculature and within the interstitium. Particles having a net surface charge may be opsonized by serum proteins (Burns, *Nano Lett.* (2009); Moghimi, *Pharmacol. Rev.* (2001)), effectively increasing probe size and preventing renal excretion. By attaching PEG chains to the particle surface to create chemically neutral surfaces and bioinert platforms, uptake by other cells is largely prevented and particles will effectively be excreted by the kidneys. Furthermore, compared to its charged counterparts, a more neutrally-charged surface will increase diffusion and lead to a more homogeneous distribution within the interstitial space of cancer-infiltrated tissues (Jain, *Nat. Rev. Clin. Oncol.* (2010)).

Brightness and Photostability

Fluorescence probes (e.g., organic dyes, fluorescent proteins, dye-bound proteins/macromolecules, dye-containing nanoparticles) have enhanced imaging evaluations of the lymphatic system in the intraoperative setting, facilitating localization of the SLN/s, draining tumor lymphatic channels, and enabling the simultaneous visualization of nodal distributions (Kobayashi, *Nano Lett.* (2007) from different draining regions. Newer generation probes that emit in the NIR region (650-900 nm) exhibit decreased tissue attenuation and autofluorescence from non-target tissues, thereby maximizing target to background ratios and offering improved, but overall low, depth penetration (3-4 millimeters) relative to visible emitters (Lucarelli, *Lymphatic Res. Biol.* (2009)). By covalently incorporating organic dyes (i.e., Cy5.5) into the silica matrix of our particle probe to prevent dye leaching (Burns, *Nano Lett.* (2009); Burns, *Chem. Soc. Rev.*, (2006)), notable photophysical enhancements over the free dye have been observed. Silica encapsulated dye molecules were found to exhibit significant increases in brightness (200-300%) and extended photostability (2-3 fold increases) compared with the free dye (Burns, *Nano Lett.* (2009)). Higher penetration depths have also been found in in vivo SLN mapping studies using a state-of-the-art fluorescence camera system (described below), with our particle visible through a maximum of 2 cm of tissue. The combination of these unique photophysical features, in conjunction with the fluorescence camera systems of the present disclosure, enable improved staging and treatment of cancer.

Image-Guided Surgery: ArteMIS™ Fluorescence Imaging System

Figure 5A:
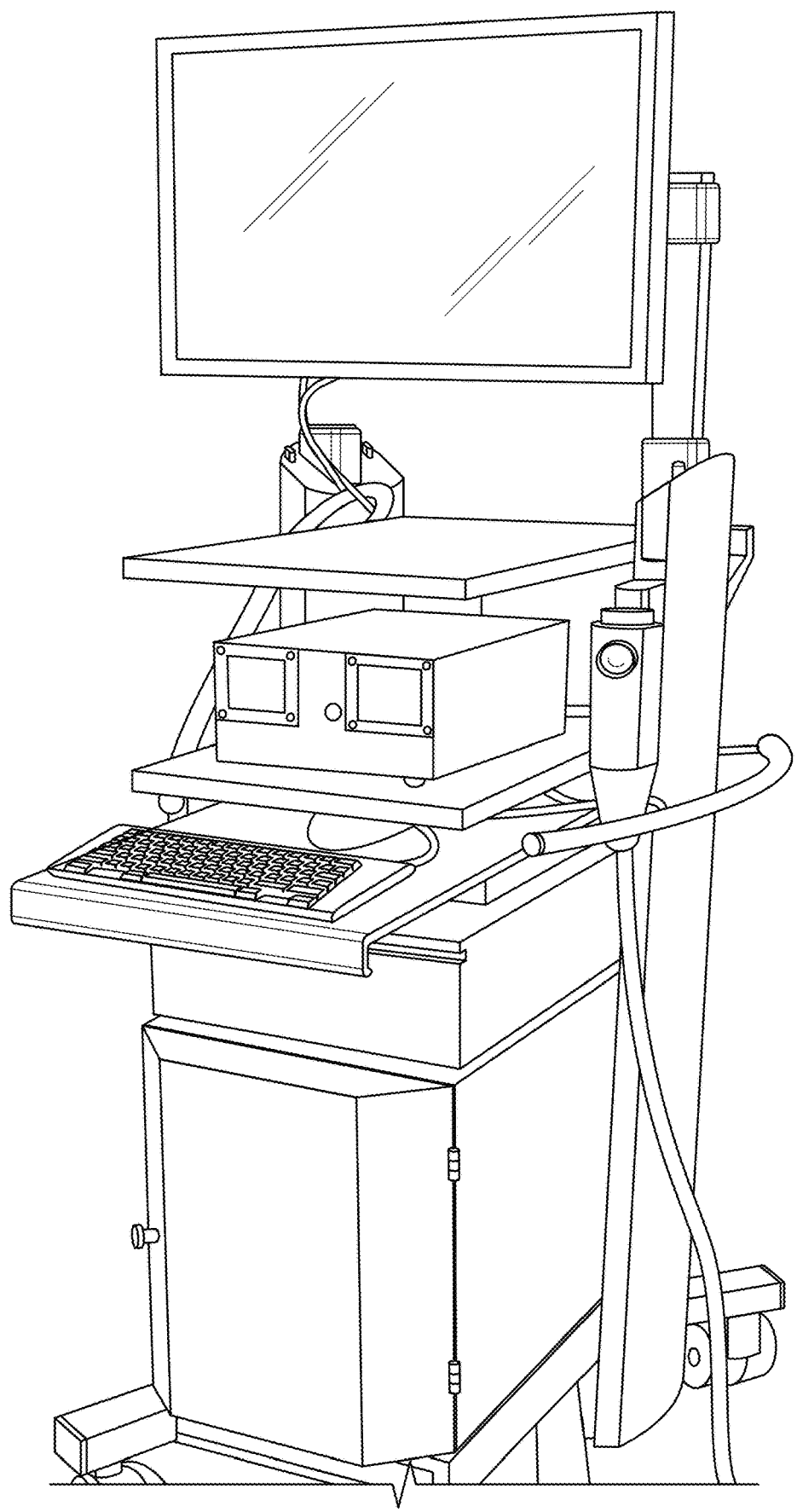
FIG. 5A depicts an ArteMIS™ handheld camera fluorescence imaging system for open and laparoscopic procedures, in accordance with an embodiment of the present disclosure.
Figure 5B:
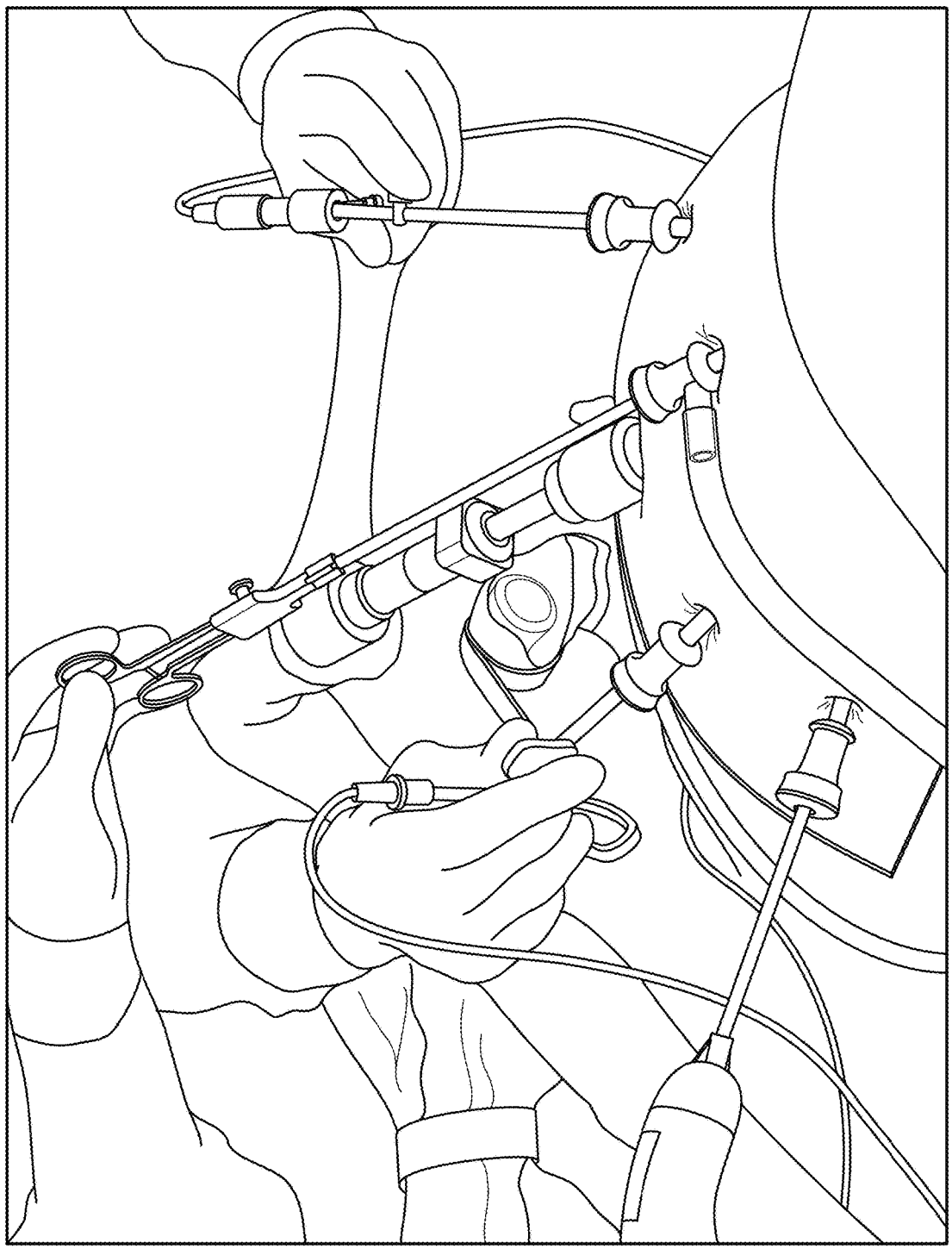
FIG. 5B depicts minimally invasive surgery using laparoscopic tools, in accordance with an embodiment of the present disclosure.
Figure 5C:
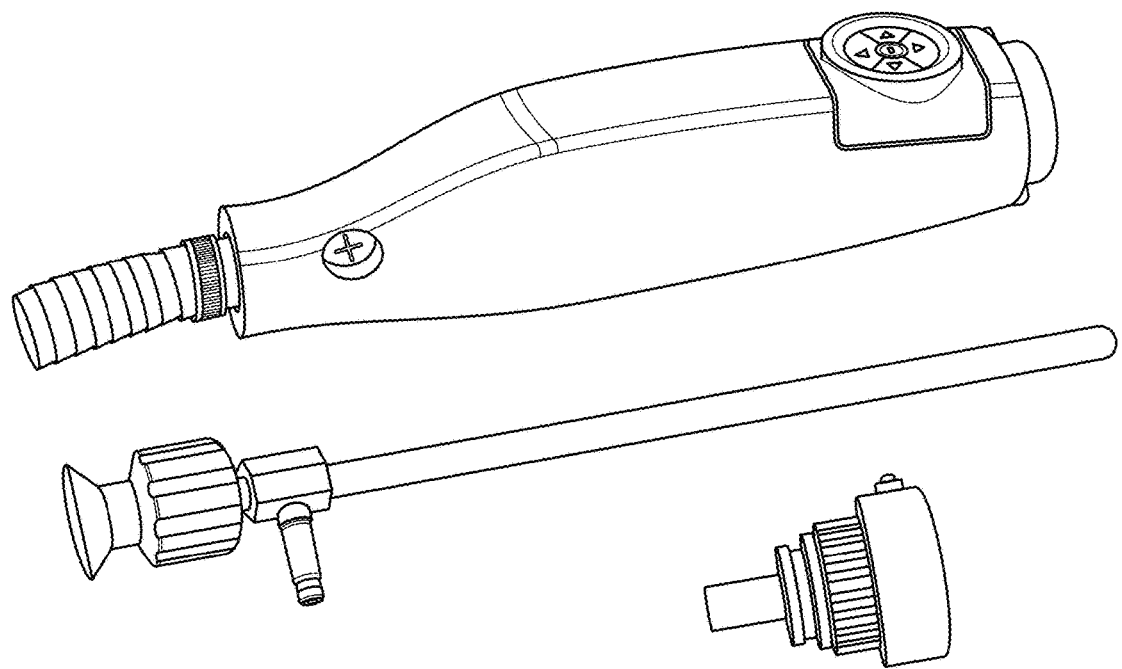
FIG. 5C depicts System components (top to bottom): camera, laparoscope, and ring light, in accordance with an embodiment of the present disclosure.
Figure 5D:
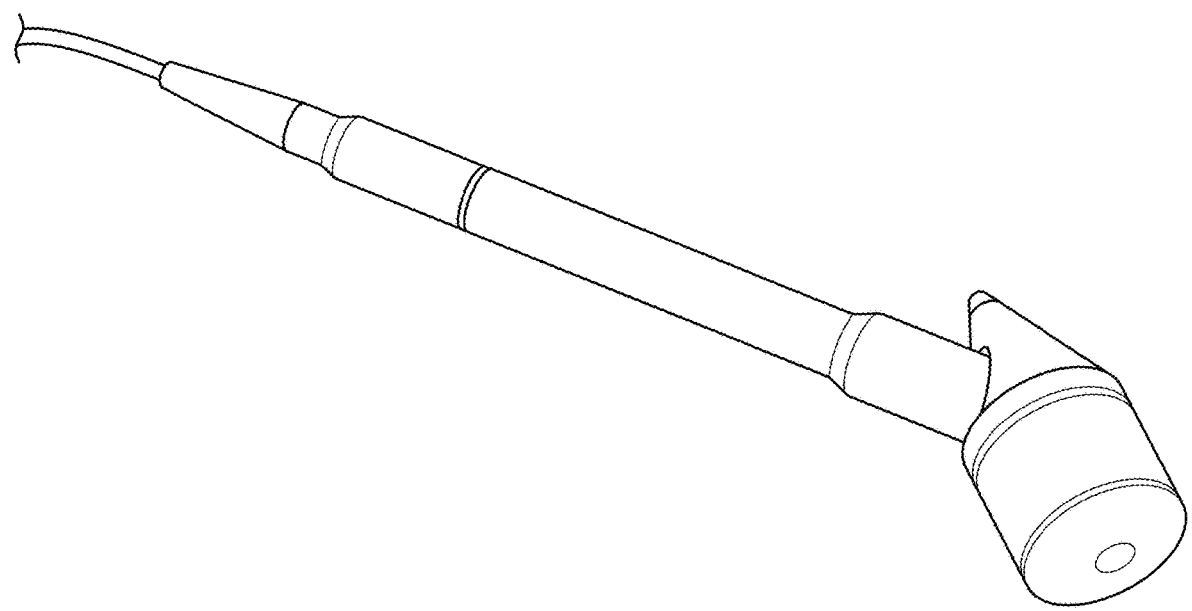
FIG. 5D depicts handheld gamma probe for radiodetection, in accordance with an embodiment of the present disclosure.
Figure 5E:
FIG. 5E depicts optical imaging of a serial dilution of 10 nm Cy5.5-containing cRGDY-PEG-C dots (exposure=60 ms; gain=125; laser power=85%; camera distance=175 mm), in accordance with an embodiment of the present disclosure.

FIGS. 5A-E depict minimally invasive surgery utilizing a handheld fluorescence camera system, in accordance with an embodiment of the present disclosure. FIG. 5A depicts an ArteMIS™ handheld camera fluorescence imaging system for open and laparoscopic procedures. FIG. 5B depicts minimally invasive surgery using laparoscopic tools. FIG. 5C depicts System components (top to bottom): camera, laparoscope, and ring light. FIG. 5D depicts handheld gamma probe for radiodetection. FIG. 5E depicts optical imaging of a serial dilution of 10 nm Cy5.5-containing cRGDY-PEG-C dots (exposure=60 ms; gain=125; laser power=85%; camera distance=175 mm). FIG. 5A shows one intraoperative imaging device, the ArteMIS™ hand-held fluorescence camera system (Quest Medical Imaging, Middenmeer, The Netherlands) that has been adapted for both minimally invasive laparoscopic, such that is depicted in FIGS. 5B and 5C and open surgical procedures, such that depicted in FIG. 5C, according to an embodiment of the present disclosure. It is a hand-held, multi-channel fluorescence imaging camera for intraoperative imaging guidance, producing high-resolution visible (color) images and fine-tuned near-infrared (NIR) fluorescent signals, which are simultaneously acquired in real-time. This capability enables motion-free overlaying. This hand-held device is optimal for SLN mapping procedures, as it can be positioned to view otherwise difficult anatomic locations, such as the head and neck. Importantly, the capability of acquiring simultaneous images of different fluorescence wavelengths (i.e., multispectral imaging) enables utilization of fluorescence imaging guidance for surgical and interventional procedures. Sensors in the device are physically aligned such that the single axis lens delivers images of the specifically tuned wavelength to the appropriate sensor. Filtering out the required wavelength of interest, as well as being able to individually control each of these sensors, which are triggered to start acquiring photons at exactly the same time and same viewing position, is a difficulty addressed herein. The tight integration of the light engine, controllable from the camera system, allows optimization based on imaging feedback.

Components of a CE-certified, FDA-exempt system has been used in larger animal studies described below, and can be integrated, along with the dual-modality particle described herein, for example, into SLN mapping clinical trial protocols. Detected optical signals at sites of particle localization in vivo are not simply autofluorescence, reflecting intrinsic fluorescence of tissue structures activated by light of suitable wavelengths, which may be confirmed by a portable gamma probe used to measure detected gamma emissions prior to lymph node resection, as shown in FIG. 5D. Prior to initiating in vivo studies, a serial dilution study was performed using 10 nm Cy5.5-containing cRGDY-PEG-C dots, along with the portable camera system, to measure changes in optical signal as a function of particle concentration (FIG. 5E).

Nanomedicine Applications: Dual-Modality Silica Nanoparticles for Image-Guided Intraoperative SLN Mapping FIG. 6 depicts imaging of metastatic disease in a spontaneous melanoma miniswine model, in accordance with an embodiment of the present disclosure. $^{124}$I-cRGDY-PEG-C dots and combined PET-optical imaging approaches can evaluate SLN mapping in a spontaneous melanoma miniswine model (Misfeldt, *Vet. Immunol. Immunopathol.* (1994); Oxenhandler, *Am. J. Pathol.* (1979); Millikan, *J. Invest. Dermatol.* (1974)) (Sinclair miniature swine, Sinclair Research Center). Image-guided metastatic disease detection, staging, and the assessment of differential tumor burden in SLN/s were evaluated in 4-10 kg miniswine (n=5) in conjunction with correlative histopathology. The results of these studies, described below, suggested that $^{124}$I-cRGDY-PEG-C dots enabled superior detection sensitivity and discrimination of metastatic tumor burden within hypermetabolic neck nodes relative to $^{18}$F-FDG. In all miniswine, dynamic 1 h high-resolution and whole body $^{18}$F-FDG PET-CT scans were performed following systemic injection of 5 millicuries (mCi) $^{18}$F-FDG to screen for metastatic disease, prior to $^{124}$I-cRGDY-PEG-C dot administration. FIG. 6A depicts whole-body $^{18}$F-FDG PET-CT sagittal and axial views demonstrating primary tumor (dark arrow) and single SLN (white arrow) posteriorly within the right (Rt) neck after i.v. injection. ant, anterior. In a representative animal, a hypermetabolic melanomatous lesion and PET-avid right-sided SLN were initially identified in the posterior neck, as shown in FIG. 6A. Two days later, $^{124}$I-cRGDY-PEG-C dots (~0.5 mCi, >95% purity) were administered as a 4-quadrant, subdermal injection dose about the tumor site. FIG. 6B is a high-resolution PET-CT scan revealing bilateral nodes 1 hour after subdermal, 4-quadrant, peritumoral injection of $^{124}$I-cRGDY-PEG-C dots (SLN, arrow; left-sided node, arrowhead). High resolution and whole body dynamic PET scans confirmed the prior $^{18}$F-FDG imaging findings 5 minutes after injection, with the additional identification of 2 PET-avid nodes, as shown in FIG. 6B, one within the left posterior neck and a second immediately anterior to the SLN. No other PET-avid nodes or suspicious areas of tracer uptake were seen.

FIGS. 6C and 6D are gross images of the cut surfaces of the black-pigmented SLN (asterisk, FIG. C) and contralateral metastatic node (arrowhead, FIG. D) in the left posterior neck. Imaged nodes were confirmed intraoperatively within the exposed surgical bed by visual inspection and γ-counting using hand-held PET devices prior to excision. FIG. 6C shows excised gross nodal specimens showed a black-pigmented (melanin-containing) SLN measuring 1.3×1.0× 1.5 cm$^3$, as compared with the smaller (1.0×0.6×1.0 cm$^3$) posterior, left-sided PET-avid node, shown in FIG. 6D. Moreover, FIG. 6E is a low-power view of H&E-stained SLN demonstrating scattered melanomatous clusters (white arrowhead) and FIG. 6F is a corresponding high-power view of H&E-stained SLN, revealing melanoma cells (yellow arrowheads) and melanophages (white arrowhead). H&E-stained SLN tissue sections revealed dark melanomatous clusters on low-power views (FIG. 6E) comprised of both melanoma cells and melanin-containing macrophages (i.e., melanophages) on high-power views, as shown in FIG. 6F. These findings were similar to those for excised primary lesions (data not shown). FIG. 6G is a low-power image of a melanoma-specific marker, HMB-45 (white arrowhead), in representative SLN tissue. FIG. 6H is a high-power image of HMB-45-stained SLN tissue. FIG. 6I is a low-power view of H&E-stained contralateral lymph node showing scattered melanomatous clusters (arrowhead). FIG. 6J is a high-power image of contralateral node showing infiltration of melanomatous cells (arrowheads). FIG. 6K is a low-power image of representative normal porcine nodal tissue. FIG. 6L. High-power image of representative normal porcine nodal tissue. Scale bars: 1 mm (FIGS. 6E, 6G, 6I, 6K); 20 mm (FIGS. 6F, 6H, 6J, 6L). (Adapted from *J. Clin. Invest.*, 2011, 121, 2768-2780). Immunohistochemical staining of the SLN with a known human melanoma marker, HMB-45, demonstrated positive expression of this marker on low-power (FIG. 6G) and high-power views (FIG. 6H). By contrast, low-power (FIG. 6I) and high-power (FIG. 6J) views of H&E stained sections from the left-sided PET-avid node showed a few smaller sized melanomatous clusters containing melanoma cells and melanophages. Tumor burden in this smaller node, estimated to be 10- to 20-fold less than in the SLN by pathological analysis, was sensitively discriminated by the targeted particle probe. Representative normal-appearing porcine nodal tissue harvested from the neck revealed no metastatic infiltration in low-power (FIG. 6K) and high-power (FIG. 6L) views.

FIGS. 7A-7I depict image-guided SLN Mapping in a spontaneous melanoma miniswine model using pre-operative PET imaging, in accordance with an embodiment of the present disclosure. These studies were expanded to include optical imaging using the portable ArteMIS™ fluorescence camera system, along with radiodetection using the gamma probe, for performing real-time assessments of the draining tumor lymphatics and nodal metastases. In a representative miniswine, depicted in FIGS. 7A-7H, initial pre-operative PET-CT scanning was performed using $^{18}$F-FDG and $^{124}$I-cRGDY-PEG-C dots using the following procedure. FIGS. 7A and 7B are axial CT images revealing a left pelvic soft tissue mass (FIG. 7A, arrow) and left flank SLN (FIG. 7B, arrow). FIGS. 7C and 7D are axial $^{18}$F-FDG PET images showing localized activity within the tumor (FIG. 7C, black arrow) and left flank SLN (FIG. 7D, black arrow) following i.v. tracer injection. Axial CT images revealed a primary pelvic tumor (FIG. 7A) and draining SLN (FIG. 7B), which were seen as areas of increased activity on the corresponding $^{18}$F-FDG PET scan (FIGS. 7C and 7D). FIG. 7E is an axial $^{124}$I-cRGDY-PEG-C dot co-registered PET-CT image showing site of local injection about the pelvic lesion (e, white arrow). FIG. 7F is a coronal $^{124}$I-cRGDY-PEG-C dot co-registered PET-CT image showing site of local injection about the pelvic lesion (FIG. 7E, white arrow). FIG. 7G is an axial coronal co-registered PET-CT image localizing activity to the SLN (FIG. 7G, white arrow) and including evidence of large bladder uptake, corresponding to FIG. 7E. FIG. 7H is a coronal co-registered PET-CT image localizing activity to the SLN (FIG. 7G, white arrow) and including evidence of large bladder uptake, corresponding to FIG. 7F. FIG. 7I depicts radioactivity levels of the primary tumor, SLN (in vivo, ex vivo), and a site remote from the primary tumor (i.e., background), using a handheld gamma probe. These findings were confirmed 2 days later by dynamic PET-CT imaging about 5 minutes after subdermal, 4-quadrant injection of $^{124}$I-cRGDY-PEG-C dots about the tumor site; co-registered axial (FIGS. 7E and 7G) and coronal (arrows, FIGS. 7F, 7H) views demonstrate these findings. Following pre-operative scanning, the skin overlying the SLN site was marked for intraoperative localization, and the miniswine was transported to the intraoperative suite. Baseline activity measurements, made over the primary tumor and SLN sites using the portable gamma probe (FIG. 7I), showed a 20-fold increase in activity within the SLN relative to background signal.

FIGS. 8A-8Q depict image-guided SLN mapping in a spontaneous melanoma miniswine model, showing real-time intraoperative optical imaging with correlative histology, in accordance with an embodiment of the present disclosure. Intraoperative SLN mapping was performed on the animal shown in FIG. 7A-7H. FIGS. 8A-8I depict two-channel NIR optical imaging of the exposed nodal basin. FIG. 8A depicts RGB color (green) with local injection of Cy5.5-incorporated particles displayed in dual-channel model. FIG. 8B depicts NIR fluorescent channels (white) with local injection of Cy5.5-incorporated particles displayed in dual-channel model. FIGS. 8C-8F depict draining lymphatics distal to the site of injection. FIG. 8F depicts fluorescence signal within the main draining distal (FIG. 8F) lymphatic channels (arrows) extending toward the SLN ('N'). Smaller caliber channels are also shown (arrowheads). Images of the SLN displayed in the (FIG. 8G) color and (FIG. 8H) NIR channels. FIG. 8I depicts color image of the exposed SLN. FIG. 8J-8M shows images of SLN in the color and NIR channels during (FIG. 8J, 8K) and following (FIG. 8I, 8M) excision, respectively. FIG. 8N depicts low power view of H&E stained SLN shows cluster of pigmented cells (black box) (bar=1 mm). FIG. 8O shows higher magnification of FIG. 8N, which reveals rounded pigmented melanoma cells and melanophages (bar=50 mm). FIG. 8P shows low power view of HMB-45-stained (dark areas) SLN confirms presence of metastases (black box, bar=500 mm). FIG. 8Q depicts higher magnification in FIG. 8P reveals clusters of HMB-45+ expressing melanoma cells (bar=100 mm).

For real-time optical imaging of the lymphatic system, a second subdermal injection of $^{124}$I-cRGDY-PEG-C dots was administered about the tumor site with the skin intact, and the signal viewed in the color and Cy5.5 fluorescent channels, which are depicted in FIGS. 8A and 8B respectively. The adjacent nodal basin was exposed, and fluorescent signal was seen in the NIR channel flowing from the injection site, depicted in FIG. 8C, into the main proximal (FIGS. 8C and 8D), mid (FIG. 8E), and distal (FIG. 8F) lymphatic branches, which drained towards the SLN, depicted by (FIG. 8F). Smaller caliber lymphatic channels were also visualized and are depicted in FIGS. 8D and 8E. The black-pigmented SLN, viewed in dual-channel mode, depicted in FIGS. 8G and 8H, was further exposed, as shown in FIG. 8I, prior to successive nodal excision, depicted in FIGS. 8J-8M. Fluorescence signal within the in situ (FIG. 8K) and ex vivo (FIG. 8M) nodal specimen was confirmed by gamma emissions using the gamma probe (FIG. 7I), and seen to correspond to scattered clusters of tumor cells on low-power (box, FIG. 8N) and high-power (FIG. 8O) views from H&E-stained tissue sections. Positive expression of HMB-45 was identified on low-power (FIG. 8P) and high-power (FIG. 8Q) views, consistent with metastatic melanoma.

FIGS. 9A-9K depict the discrimination of inflammation from metastatic disease, by comparison of $^{18}$F-FDG and $^{124}$I-cRGDY-PEG-C dot tracers, in accordance with an embodiment of the present disclosure. FIGS. 9A-9D depict the imaging of inflammatory changes using $^{18}$F-FDG-PET with tissue correlation. FIG. 9A depicts the axial CT scan of the $^{18}$F-FDG PET study shows calcification within the left posterior neck (yellow arrows). FIG. 9B shows the fused axial $^{18}$F-FDG PET-CT reveals hypermetabolic activity at this same site (arrows). Increased PET signal is also seen in metabolically active osseous structures (asterisks). FIGS. 9C and 9D depict the low and high-power views of H&E-stained calcified tissue demonstrate extensive infiltration of inflammatory cells. FIGS. 9E-9K depict the metastatic disease detection following injection of $^{124}$I-cRGDY-PEG C dots about the tumor site. FIG. 9E shows the pre-injection axial CT scan of $^{124}$I-cRGDY-PEG-C dots shows calcified soft tissues within the posterior neck (arrows). FIG. 9F depicts the co-registered PET-CT shows no evident activity corresponding to calcified areas (arrow), but demonstrates a PET-avid node on the right (arrowhead). FIG. 9G depicts the axial CT at a more superior level shows nodes (arrowheads) bilaterally and a calcified focus (arrow). FIG. 9H depicts the fused PET-CT demonstrates PET-avid nodes (N) and lymphatic drainage (curved arrow). Calcification shows no activity (arrow). FIGS. 9I and 8J depict the low- and (FIG. 9J) high-power views confirm the presence of nodal metastases. FIG. 9K depicts the single frame from a three-dimensional (3-D) PET image reconstruction shows multiple bilateral metastatic nodes (arrowheads) and lymphatic channels (solid arrow) draining injection site (white asterisk). Bladder activity is seen (dashed arrow) with no significant tracer accumulation in the liver (black asterisk). Bladder activity is seen with no significant tracer accumulation in the liver. Scale bars in FIGS. 9C and 9D represent 500 gm, and scale bars in FIGS. 9I and 9J represent 100 gm. Surprisingly, and by contrast to the observed $^{18}$F-FDG findings, $^{124}$I-cRGDY-PEG-C dots were found to specifically discriminate between metastatic tumor infiltration and inflammatory processes in these miniswine. Mechanistic differences in the behavior of these agents at the cellular and subcellular levels, as well as the presence of an integrin-targeting moiety on the particle surface, may account for the observed imaging findings. In multiple miniswine harboring pathologically-proven inflammatory changes due to granulomatous disease (n=3), $^{18}$F-FDG failed to detect metastatic disease, while identifying inflammatory and other metabolically active sites. These discrepant findings highlighted the ability of $^{124}$I-cRGDY-PEG-C dots to selectively target, localize, and stage metastatic disease, while $^{18}$F-FDG failed in many cases to accurately stage cancer spread, instead identifying sites of inflammation.

In a representative miniswine study illustrating these findings, initial axial $^{18}$F-FDG PET-CT scans showed calcification within the left posterior neck on CT (FIG. 9A), corresponding to an area of intense activity on the $^{18}$F-FDG PET (FIG. 9B). FIGS. 9C and 9D depict low-power and high-power views, respectively, of H&E stained tissue sections revealed diffuse inflammatory changes, consistent with granulomatous disease. FIGS. 9A and 9B depict intense $^{18}$F-FDG PET activity was additionally seen within the metabolically active bone marrow compartment of these young miniswine. By contrast, the $^{124}$I-cRGDY-PEG-C dot imaging study identified bilateral metastatic neck nodes. A right neck node on axial CT imaging (FIG. 9E) was seen to be PET-avid on co-registered PET-CT (FIG. 9F); additional bilateral nodes on a more superior CT image (FIG. 9G) were also PET-avid on fused PET-CT (FIG. 9H). Moreover, left neck calcifications, as depicted in FIGS. 9E and 9G showed no PET activity on co-registered scans, as depicted in FIGS. 9F and 9H. Corresponding H&E-stained SLN tissue sections revealed dark melanomatous clusters on low-power (box, FIG. 9I) and high-power views (FIG. 9J), seen to be comprised of melanoma cells and melanophages. A single frame (FIG. 9K) selected from 3D PET reconstructed images again illustrated multiple, bilateral PET-avid neck nodes and associated draining lymphatic channels. Importantly, bulk activity was seen in the bladder 1 h post-injection without significant tracer accumulation over the liver region.

FIG. 10 depicts 3-D integrated $^{18}$F-FDG and $^{124}$I-cRGDY-PEG-C dot PET-CT, in accordance with an embodiment of the present disclosure. FIGS. 10A-10E depict 3-D volume rendered images were generated from CT and PET imaging data shown in FIG. 9. FIG. 10A depicts PET-CT fusion image (coronal view) shows no evident nodal metastases (asterisks). Increased activity within bony structures is identified. FIGS. 10B and 10C depict high-resolution PET-CT fusion images showing coronal (FIG. 10B) and superior views (FIG. 10C) of bilateral metastatic nodes (open arrows) and lymphatic channels (curved arrows) within the neck following local injection of $^{124}$I-cRGDY-PEG-C dots.

The above findings were seen to better advantage on PET-CT fusion MIP images generated from dynamic imaging data sets acquired over a 1 hour period after $^{18}$F-FDG (FIG. 10A) or local administration of $^{124}$I-cRGDY-PEG-C dots (FIGS. 10B and 10C). For $^{18}$F-FDG, a clear absence of nodal metastases is noted, with diffusely increased activity seen within metabolically-active bony structures. In contrast to these findings, $^{124}$I-cRGDY-PEG-C dots detected bilateral metastatic neck nodes, along with draining lymphatic channels.

In several of the miniswine evaluated, the particle tracer was found to specifically discriminate metastatic tumor infiltration from hypermetabolic processes, the latter typically detected by the non-specific imaging tracer $^{18}$F-FDG (FIGS. 10A-10C). Corresponding H&E-stained SLN tissue sections confirmed the imaging findings, revealing dark melanomatous clusters comprised of melanoma cells and melanophages (i.e., melanin-containing histiocytes). In a second representative miniswine study, a primary pelvic tumor and draining SLN were initially identified on axial CT imaging, and then seen as areas of increased activity on the corresponding $^{18}$F-FDG and 2-day follow-up $^{124}$I-cRGDYPEG-C'dot PET-CT scans, the latter obtained after subdermal injection about the tumor site.

Dual-Modality Silica Nanoparticles for Image Guided Interventions: Treatment Response The ability of the $^{124}$I-cRGDY-PEG-C dots to discriminate metastatic disease from tissue inflammatory changes could potentially be exploited in a variety of therapeutic settings—either surgically-based or interventionally-driven—as treatment response assessments are often confounded by the presence of inflammatory changes, making interpretation difficult. Image-guided interventions, such as therapeutic tumor ablations, may specifically benefit from the innovative coupling of new particle platform and imaging device technologies to (1) enable earlier post-procedural evaluation of response; (2) verify complete ablation or detect residual tumor representing treatment failure, and (3) improve tumor surveillance strategies. Locally ablative therapies, including microwave ablation (Lubner, J. Vasc. Interv. Radiol. (2010)), cryoablation (Erinjeri, J Vasc Interv Radiol (2010)), radiofrequency ablation (RFA) (Abitabile, Eur. J. Surg. Oncol. (2007); Amersi, Arch. Surg. (2006); Farrell, A J R, Am. J. Roentgenol. (2003); Hong J Vasc Interv Radiol (2010)), and laser interstitial therapy, induce local thermal injury via an energy applicator insertion into tumors. These methods are typically employed as alternative options in patients deemed ineligible for surgical excision (Anderson, Clin. Nucl. Med. (2003); Purandare, Radiographics, (2011)). Further, patients undergoing ablative therapies are often poor surgical candidates due to co-morbidities. Widely used in clinical practice, they offer a distinct advantage, as they can be performed percutaneously as outpatient procedures with significantly less morbidity, and may improve quality of life and survival in selected patient cohorts (Purandare, Radiographics, (2011); Barker, A J R Am J Roentgenol, (2005)).

Accurate post-therapy imaging, typically acquired 1-3 months after an ablation procedure, traditionally utilized contrast-enhanced volumetric imaging, such as CT or MRI (Anderson, Clin. Nucl. Med. (2003); Purandare, Radiographics, (2011); Barker, A J R Am J Roentgenol, (2005)). These techniques suffer from a number of drawbacks. First, they are limited to identifying the presence of abnormal enhancement or growth in the size of the tumor area (Purandare, Radiographics, (2011)), considered primary indicators of residual tumor or recurrent disease. Diffuse rim enhancement about the ablation zone on post-procedural evaluations may be related to inflammation and hyperemia in the ablation zone, and often does not necessarily represent residual tumor (Barker, A J R Am J Roentgenol, (2005)). Increasing enhancement, notably irregular or nodular, is considered suspicious for tumor. However, these interpretations are controversial, as an ablation zone can look larger than expected for several months post-procedure, and enhancement might also reflect granulation or scar tissue formation (Barker, A J R Am J Roentgenol, (2005); Vogt, J. Nucl. Med., (2007)). Functional methods, such as $^{18}$F-FDG PET, have also been used to assess the efficacy and effects of locally ablative procedures, but may suffer from an inability to accurately discriminate tumor from inflammatory changes. Thus, interpretation of imaging changes (i.e., inflammation, tumor) at the tissue level in response to ablative procedures using current morphologic or functional assessments, particularly at early time intervals, is a significant challenge. What is needed are reliable endpoints for ablation success and unequivocal detection of residual disease in the post-ablation period.

FIGS. 11A-11O depict single-dose $^{124}$I-cRGDY-PEG-C dot localization of the SLN. FIG. 11A depicts the baseline coronal CT (white arrowhead), FIGS. 11B and 11C depict PET (black arrowhead) and fused PET-CT images (white arrowhead), respectively, following a peritumoral injection.

FIGS. 11B-11D depict tumor $^{124}$I-cRGDY-PEG-C dot activity. FIG. 11 depicts PET-avid exophytic left pelvic mass (black arrow). FIGS. 11C and 11D show combined PET-CT images showing a PET-avid lesion (white arrow) and $^{124}$I-cRGDYPEG-C dot flow within a draining lymphatic channel (asterisk) towards the SLN (curved arrow). FIGS. 11E and 11F depict pre-ablation axial CT images locate the SLN (e, white arrowhead) prior to RFA electrode placement (FIG. 11F, arrow) into the node (below crosshairs). FIG. 11G shows that pre-ablation fused PET-CT reveals increased SLN activity (posterior to cross-hairs). FIG. 11H depicts that post-ablation PET-CT scan shows mildly reduced activity at the SLN site, anterior to the needle tip. FIG. 11I depicts corresponding pre-ablation H&E staining of core biopsy tissue from the SLN confirms pigmented tumor infiltration (bar=200 gm). FIG. 11J depicts high magnification of boxed area in FIG. 11I reveals large, rounded pigmented clusters of melanoma cells (bar=50 gm). FIG. 11K depicts post-ablation H&E staining shows necrotic changes within a partially tumor-infiltrated node (box) and multifocal hemorrhages (bar=500 gm). FIG. 11L shows high magnification of FIG. 11K, which reveals significant tissue necrosis (arrowheads) within the metastatic node, in addition to lymphoid tissue (bar=50 gm). FIG. 11M depicts TUNEL staining of metastatic SLN before ablation (bar=20 gm). FIG. 11N depicts post-ablation TUNEL staining demonstrating focal areas of necrosis (dark area) with adjacent scattered tumor foci and normal nodal tissue (NT) (bar=500 gm). FIG. 11O depicts high magnification of boxed area in FIG. 11N. shows positive TUNEL staining (dark area), consistent with necrosis (bar=20 gm).

As a forerunner to performing future ablations of metastatic liver lesions, a proof-of-concept radiofrequency ablation (RFA) study of a larger (i.e., 1-2 cm) SLN was performed in a miniswine with metastatic melanoma to evaluate early treatment response in the presence of $^{124}$I-cRGDY-PEG-C dots. PET-CT imaging findings prior to and after RFA were correlated histologically. Following subdermal injection of $^{124}$I-cRGDY-PEG-C dots (~0.6 mCi) about the primary left pelvic tumor, an initial baseline coronal CT showed a 2.2×1.6 cm SLN (FIG. 11A) superior to the tumor site, which was PET-avid (FIGS. 11B and 11C). The PET-avid left pelvic tumor is also shown (FIG. 11B), noting additional flow of $^{124}$I-cRGDY-PEG-C dots within a draining lymphatic channel on fused PET-CT images (FIGS. 11C and D). Additional serial CT scans were acquired to localize the node (FIG. 11E) prior to the ablation procedure and guide RFA probe insertion (FIG. 11F) into the node (below level of crosshairs). On the corresponding pre-ablation co-registered PET-CT scan, the PET-avid SLN was seen just posterior to crosshairs (FIG. 11G). A partial node ablation was performed for 12 minutes using a 2 an active tip RFA probe (Cool-tip ablation system, Covidien plc, Dublin, Ireland). Post-ablation PET-CT showed mildly reduced tracer activity in the ablation zone, anterior to the electrode tip (FIG. 11H).

Pre- and post-ablation imaging findings were confirmed histologically. H&E staining of pre-ablated core biopsy tissue from the SLN confirmed diffuse metastatic tumor infiltration on low-power (FIG. 11I) and high-power (FIG. 11J) views. Post-ablation, the extent of metastatic infiltration decreased on H&E stained nodal tissue, seen on corresponding low- (FIG. 11K) and high-power views (FIG. 11L). Coagulative necrosis and lymphoid tissue were also identified, along with multifocal hemorrhages FIGS. 11K and 11L, respectively). TUNEL stained high-power views prior to ablation reveal scattered neoplastic cells (FIG. 11M). On post-ablation TUNEL staining, focal areas of necrosis (red) were seen on both low- (FIG. 11N) and high-power (FIG. 11O) views. In proof-of-concept SLN mapping studies, such a strategy to detect multiple cancer targets in a spontaneous melanoma miniswine model can be used by employing two spectrally-distinct NIR dye-containing C' dots, each functionalized with a different melanoma-directed peptide (cRGDY-PEG-CW800-C'dots; αMSHPEG-Cy5.5-C'dots).

FIGS. 12A-12D depict screening pre-operative SLN mapping study in miniswine using PET imaging and $^{124}$IcRGDY-PEG-CW800-C'dots, in accordance with an embodiment of the present disclosure. FIG. 12A depicts axial neck CT image reveals a left-sided cutaneous soft tissue mass (arrow). FIG. 12B depicts co-registered axial PETCT images show foci of increased activity at sites of local injection of the particle tracer. FIG. 12C depicts a CT image at a more proximal level to tumor reveals the SLN within the deep left neck soft tissues (arrow). FIG. 12D depicts a coregistered axial PET-CT image localizes activity to the node. In a representative miniswine study, preoperative PET-CT screening for metastatic nodal disease was initially performed after subdermal, peritumoral injection of one of these radiolabeled particle probes—$^{124}$I-cRGDY-PEG-CW800-C'dots—about a primary cutaneous lesion on the left shoulder region (FIGS. 12A and 12B). A well-defined lymph node proximal to the primary lesion, and within the deep tissues of the left neck, was seen on pre-operative axial CT imaging (FIG. 12C). Increased activity was seen at the site of this node on the corresponding co-registered axial PET-CT scan (FIG. 12D).

FIGS. 13A-13L depict intraoperative real-time optical imaging of SLN metastases using αMSH-PEG-Cy5.5-C'dots, in accordance with an embodiment of the present disclosure. Two channel fluorescence imaging was performed. FIGS. 13A, 13B depict a dual-channel mode (FIG. 13A) and Cy5.5 channel (FIG. 13B) images of fluorescence signal (light area) extending from the injection site to the SLN within the main lymphatic channel after local injection of αMSH-PEGCy5.5-C'dots about the primary tumor site in a melanoma miniswine model. Dual-channel mode (FIGS. 13C, 13E) and Cy5.5 channel images (FIGS. 13D, 13F) of the SLN. A second NIR fluorescence ('blue') signal (CW800 channel) was also seen after local injection of cRGDY-PEG-CW800-C'dots about the tumor (FIG. C; arrow). Dual- (FIG. 13G) and Cy5.5-channel (FIG. 13H) images of excised, bisected node. FIGS. 13I and 13J depict low- and (FIG. 13J) high-power views, respectively, of the H&E stained SLN. FIGS. 13K and 13L depict low- and high-power views, respectively, of HMB45+ stained SLN. In the intraoperative suite, for the first time, a second melanoma-targeting particle probe, αMSH-PEG-Cy5.5-C'dots for mapping metastatic nodal disease was assessed in this miniswine model (FIGS. 13A-13L). Of note, cRGDY-PEG-Cy5.5-C' dots have been clinically translated for imaging nodal metastases. For this study, both Cy5.5 and CW800 lasers were turned 'on', as both particle probes were being detected, as described below. αMSH-PEGCy5.5-C'dots (~7 nanomoles; 0.5 ml) were locally injected about the primary lesion and, after surgical exposure of the nodal basin, dual-channel (RGB color/Cy5.5), real-time optical imaging was performed using the Artemis™ fluorescence camera system. Fluorescence signal (white dots) was observed in dual channel mode (FIG. 13A) and in the Cy5.5 channel (FIG. 13B), flowing within a draining lymphatic channel that extended from the injection site to the SLN. Dual-channel mode (FIGS. 13C, 13E) and Cy5.5 channel (FIGS. 13D, 13F) images showed a progressive increase in fluorescence signal (green) within the exposed node over ~10 minutes p.i. During this time, a second particle probe, cRGDY-PEG-CW800-C' dots, was injected about the primary tumor (arrow; FIG. 13C). and fluorescence ('blue') signal (CW800 channel) was observed. After resecting the SLN, it was bisected to reveal fluorescence signal, as seen in both dual channel (FIG. 13G) and Cy5.5 channel (FIG. 13H) images. Low power view of H&E stained SLN (FIG. 13L) shows a largely tumor-replaced node (arrow; bar=1 mm). Higher magnification reveals rounded pigmented melanoma cells (arrows) (bar=50 µm). Low power view of HMB45+-stained (red) SLN confirms metastatic disease (arrow; bar=1 mm), while higher magnification reveals clusters of HMB45+ expressing melanoma cells (arrows; bar=50 µm).

FIGS. 14A-14D depict multiplexed imaging of nodal metastases, in accordance with an embodiment of the present disclosure. (FIG. 14A) Composite image and corresponding (FIG. 14B) Cy5.5 and (FIG. 14C) CW800 channel images of a downstream node with (FIG. 14D) histologic confirmation of melanoma by HMB45+ staining. Two fluorescent channel imaging of a smaller resected lymph node downstream from the SLN was acquired (FIG. 14A), noting signal in both Cy5.5 (white, FIG. 14B) and CW800 (white, FIG. 14C) channels. Histological confirmation of melanoma was found on HMB-45+ stained SLN (FIG. 14D).

Lymph node metastases are a powerful predictor of outcome for melanoma. Early detection of micrometastases in regional lymph nodes using SLN mapping may permit the timely stratification of patients to appropriate treatment arms, and improve patient outcomes. Although the current standard-of-care SLN mapping and biopsy techniques rely on the use of radioactivity-based identification of SLN/s, a number of limitations of this technology exist. These include low spatial resolution, reduced staging accuracy, absence of target specificity, slow tracer clearance that may obscure the surgical field, and the lack of accurate intraoperative visualization to prevent injury to vital structures lying in close proximity to SLN/s.

The translation of radiolabeled ($^{125}$I)-αMSH peptides to the clinic as melanoma-selective imaging probes has not been successful to date, the consequence of non-specific accumulation in the kidneys, which has resulted in increased kidney-to-tumor ratios. Overcoming this limitation has required innovation at every level of product development, including its attachment to renally excreted C' dots, as well as adaptations made to peptide design, particle surface chemistry, and peptide conjugation strategies. As FDA-IND approval has been previously received for two targeted, NIR dye incorporated silica particle products, generation of a third IND-enabling technology—CW800 dye incorporated αMSH-PEG-CW800-C' dots, which have been optimized for mapping metastatic nodal disease, can be generated.

Further, the combined use of this product and FDA-IND approved cRGDY-PEG-Cy5.5-C'dots for real-time multiplexed optical detection of multiple cancer targets in larger-animal melanoma models, in conjunction with a new hand-held high sensitivity, multispectral fluorescence camera system (ArteMIS™, Quest Medical Imaging, QMI) capable of simultaneously detecting multiple spectrally-distinct optical signals, can generate new staging biomarkers that can be validated in subsequent clinical trials. The ArteMIS™ camera overcomes limitations associated with existing "black box" small animal imaging technologies, while achieving much higher spatial and wavelength resolutions. Multiplexing strategies of the ArteMIS™ system can be extended to inform the development of novel dye-functionalized nerve binding peptide probes (and corresponding particle conjugates) that detect normal nerve tissue markers by chemically adapting (i.e., cyclization) existing murine nerve binding peptides (NBP) to enhance binding affinity and avidity.

Newer generation, biocompatible particle platforms can be actively tailored to enable selective probing of critical cancer targets according to embodiments described herein, and can offer important insights into cellular and molecular processes governing metastatic disease spread. The additional adaptation of such platforms for multimodality imaging can be used to advantage by the operating surgeon or interventionalist to explore these processes in a variety of image-guided procedural settings. One such dual-modality platform, a clinically-translated integrin-targeting silica nanoparticle developed for both optical and PET imaging, meets a number of key design criteria—small size, superior brightness, enhanced tumor tissue retention, and low background signal—that make it an ideal agent for SLN localization and staging during SLN biopsy procedures when coupled with portable, real-time optical camera systems (i.e., ArteMIS). The ability to discriminate metastatic disease from tissue inflammatory changes in melanoma models, which are often co-existing processes, in addition to surrounding nerve tissue, may provide a more accurate and reliable marker for the assessment of treatment response in the future.

Real-Time Simultaneous Imaging

In some embodiments, the methods and systems described herein simultaneously detect radiation of different wavelengths from different probe species within a subject and discriminate between signals received from each probe species. In some embodiments, this is accomplished with an apparatus comprising a light source configured to deliver multiple excitation wavelengths of light to excite a plurality of fluorescent reporters, thereby producing fluorescent light at two or more distinguishable wavelengths; a prism configured to direct light received through a lens onto a plurality of spatially-separated detectors such that said detectors can measure, in real-time, different emitted signals simultaneously; and a processor configured to process signals corresponding to the detected fluorescent light at the two or more distinguishable wavelengths to provide images of fluorescence within a subject. In some embodiments, this involves multiplexing of signals.

In some embodiments, in order to provide the multiplexing capabilities, it is required that a camera take pictures or movies (sequences of images) at multiple wavelengths of exactly the same object. In some embodiments, this requires the camera to comprise multiple detectors on a prism-like structure where all sensors (2 or more) "see" the object through a single lens and hence have the same view. In this embodiment, the pixels on the detectors are detecting a different wavelength of the exact same emitting signal of the object. In some embodiments, this knowledge allows performance of ratio imaging and/or other types of image processing to carry out spectral unmixing.

In some embodiments, it is useful to know the emitting signal and then conclude from the signal measured that it is to be linked directly to a light engine that is capable of outputting different excitation wavelengths in order to excite the chemical substance and cause the fluorescent effect that is observed. In some embodiments, there is a direct link between the camera and the light engine in order to perform this task.

In some embodiments, in order to create a sufficient signal to background ratio, a specially designed filter is placed in front of the lens. This multiband filter is designed such that it will block out any high power excitation light coming from the light source (and therefore the filter is tuned to the light engine laser light), but will be transparent for all other light (hence, the visible light and all the emission wavelengths of interest. In some embodiments, when the light is passed through the lens, it is passed to a prism separating the light based on wavelength that exactly matches the wavelengths of the emission signals of interest. In some embodiments, between the prism and the sensor a final small band filter is placed to narrow down the sensitivity that the detector picks up to exactly match the emission signal that is desired to measure. In some embodiments, in addition to discriminating the sensitivity of multiplexed signals, one is also capable of detecting the visible color signal, e.g., via a separate detector, and further enabling the overlay (e.g., superimposition) of detected signals onto a color image.

Current systems are generally based on single detectors for color. They are not capable of detecting multiple channels simultaneously, but, instead, are detecting in a time multiplexed manner, where either the detection is switched for a period of time (between color image and fluorescence image) or a high alternating frequency is used (50 Hz or more) to switch in real-time. This technique cannot be used with spectral unmixing because a time factor is introduced and there is no guarantee that the signal comes from exactly the same position as the previous detected signal is coming from. Also, the light source stability in power has larger fluctuations that influence the signal stability and therefore the outcome of the unmixed signal.

There are other imaging systems that detect separate dyes having different structures. However, these systems do not perform multiplexing or de-multiplexing. Because there is no relation between the dyes, they have to be detected as separate fluorescent images. In the cases of these other systems, no signal information from one dye is detectably related to the signal of the other dye.

However, using the systems and methods described herein, e.g., by coupling the light engine and further matching between light engine and camera, it can be observed that the multiplexed dyes contribute to both signals. Furthermore, by means of ratio imaging and using information from both images, these signals can be de-multiplexed and identified. In some embodiments, the dyes, systems and methods described herein can carry out simultaneous, real-time imaging of signals not observed with other technologies. The methods described herein can be performed, for example, with optical imaging modalities and measurement techniques including, but not limited to: endoscopy; fluorescence endoscopy; luminescence imaging; bioluminescence tomography, time resolved transmittance imaging; transmittance imaging; nonlinear microscopy; confocal imaging; acousto-optical imaging; photoacoustic imaging; reflectance spectroscopy; spectroscopy; coherence interferometry; interferometry; optical coherence tomography; diffuse optical tomography and fluorescence mediated molecular tomography (continuous wave, time domain frequency domain systems and early photon), and measurement of light scattering, absorption, polarization, luminescence, fluorescence lifetime, quantum yield, and quenching.

Multichannel Imaging System Features

The systems and apparatus described herein differ from previous imaging systems in their ability to carry out simultaneous detection of light signals at different wavelengths in real-time. The imaging apparatus comprises a multichannel fluorescence camera system that simultaneously detects multiple wavelengths from multiple dyes in real-time. The imaging apparatus comprises a hand-held fluorescent imaging system that uses multiple detectors and associated circuitry that can collect distinguishable signals from the multiple types of probe species with higher signal to noise ratio. In some embodiments, the system does not distinguish multiple signal types received at a single detector with optical time division multiplexing, as do other previous imaging systems. For example, it does not perform optical time division multiplexing.

In order to achieve a reaction for the dye containing particles which have a clearly distinguished emission signal, a specific excitation wavelength should be provided for each dye. The ability to combine multiple excitation sources is important for a multiplexing method as described herein. The excitation sources should also be of significant power, along with the addition of white light.

In some embodiments, the imaging system comprises a light engine capable of providing the desired wavelength and the desired amount of power. However, the system is also capable of discriminating between the resultant distinguishable emission wavelengths, e.g., the channels in the camera will sense the different emission wavelengths of each dye-particle. The emission signals from the dyes enter the system through a single lens (or in some embodiments—laparoscope) and are split up and directed according to their wavelength to the appropriate sensors. Each sensor is capable of detecting the emission signal. Crosstalk or overlap between the dyes can be measured as such, for example, by using ratio scanning techniques. While viewing the signal, the system enables one to determine if a signal is a build-up of a "pure" signal (either one or the other) or a combination of different signals.

In certain embodiments, the camera system comprises a prism technology that is used to interpret the incoming signal and perform the wavelength split. Along with optical filters, the light output is controlled to remove any light from the light engine that may be present in the sensing window of the camera, to make sure that the resulting signal is only of the probe species, and is not generated light from the light engine.

In some embodiments, the apparatus comprises an image-acquisition and image manipulation program with a focus on multi-channel and multi-spectral images. In some embodiments, the program supports images captured by a multi-channel handheld camera that can be used either with a lens for open procedures or a laparoscope for minimally invasive procedures. In some embodiments, such a program would enable the operator to visualize all camera channels at the same time. In some embodiments, the multi-channel handheld camera has one RGB color channel and two or more dedicated channels for fluorophores. In some embodiments, the fluorescence channels can capture signals in the visible or infrared wavelength range.

Systems with elements that can be used to employ the systems and methods described herein include, but are not limited to, the following: ArteMIS™ System (Quest Medical Imaging, The Netherlands) and High-Energy Wireless PET Probe (Intramedical Imaging LLC, Hawthorne, Calif.).

Figure 15A:
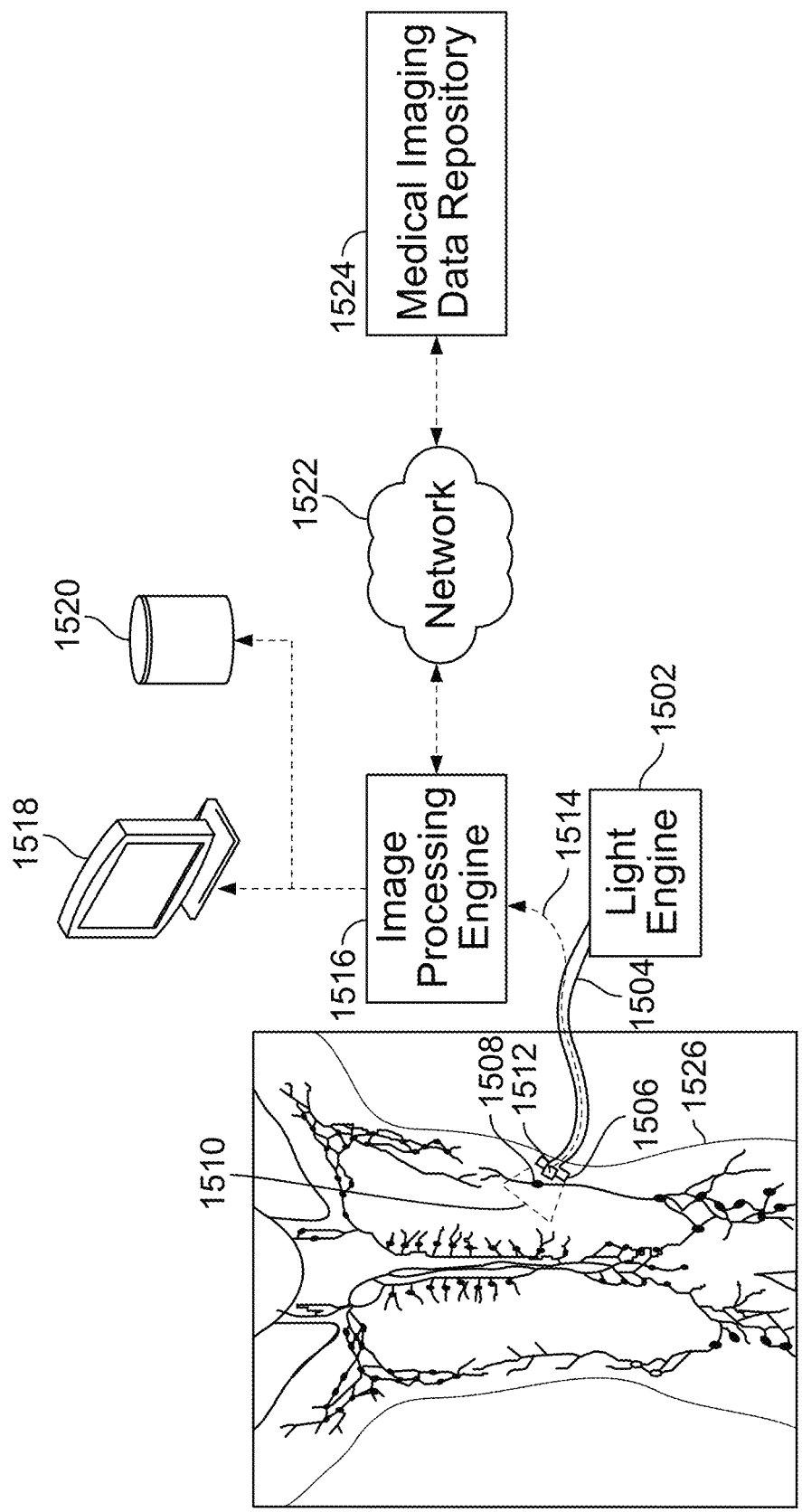
FIG. 15A depicts a schematic of the various features of the portable multichannel imaging apparatus that may be used in various embodiments described herein.

FIG. 15A shows a schematic of a portable imaging apparatus that may be used in various embodiments described herein. The portable imaging apparatus 1500 represents a simplified depiction of the present disclosure for illustrative purposes. The light engine 1502 generates excitation light at target wavelengths and functions to excite each of the fluorescent agents absorbed in the target tissues in the region of interest 1508 in subject 1526. In some embodiments, the light engine 1502 is configured to generate a specific spectrum of light adapted to the excitation wavelengths required for the nanoparticles that are used in the observation (e.g., a laser providing near infrared excitation light at a given wavelength, e.g., in the 650 nm to 900 nm range). In other embodiments, the light engine is further configured to produce excitation light, visible light, excitation light, or any combination thereof using various methods described herein. In further embodiments, the light engine 1502 generates both broad spectrum light for illumination and narrow-spectrum light for excitation. In various embodiments, the subject 1526 is a human or animal afflicted with a medical condition that requires internal, visual investigation or invasive surgery (in vivo). In some embodiments, excitation and detection are performed by non-invasive methods. In certain embodiments, the subject 1526 is a sample or biopsy (in vitro). The light engine 1502 directs light along the fiber-optic bundle 104 to illuminate and excite the observation window 1510. Nanoparticles, having already been administered via, e.g., local injection, respond to the excitation light and emit light within a known spectra (e.g., wavelength range such as red, green, or blue). The broad spectrum light and the emitted fluorescence light are collected in the camera 1512 by one or more video sensors (e.g., a CCD camera sensor, a CMOS camera sensor, etc.). The camera 1512 projects the visual data from each of the one more sensors along the video signal stream 1514. The video signal is fed to the image processing engine 1516 where various levels of processing on the video signal are performed. In certain embodiments, the image processing engine 1516 comprises one or more video processing devices (e.g., FPGAs and/or CPUs configured to process and/or adapt the video data for display in real-time). In some embodiments, the image processing engine 1516 comprises multiple modules of video processing devices (e.g., pre-processing modules, post-processing modules, etc.), and/or multiple channels of video processing devices (e.g., each channel is configured to process the video obtained from each of the one or more sensors). In some embodiments, the video processing devices in the pre-processing module are configured to perform operations in real-time that transform the time-domain video data into frequency-domain data using FFT, transform frequency-domain data into spatial-domain data, transform time-domain data into spatial-domain data, and/or perform spatial sharpening or deblurring. In certain embodiments, the video processing devices in the post-processing module are configured to perform operations such as automatic deconvolution of each spectra, flow tracking, and spatial texture based classifiers used to decipher the tissue type and/or heterogeneity associated with each of the image pixels in the region of interest 1508.

The image processing engine is further configured to interface with a medical imaging data repository (e.g., the Nanomed database) via a network 1522 such as the internet. The medical imaging data repository 1524 is configured to provide information about the area of interest 1508 based on video analysis of the processed video signal stream 1528. The medical imaging data repository 1524 comprises a collection of visual data, associated metadata, and/or other medical data which may correspond to a particular area of interest in the subject 1526, tissue type, or other useful categorization. In certain embodiments, the video is analyzed via the image processing engine 1516 or the medical imaging data repository 1524 or both. The medical information generated and/or retrieved by the medical imaging data repository is then relayed back to the image processing engine 1516 and is used to augment the processed video stream 1528. An input and display device (e.g., the touch-screen monitor 1518) displays the processed video stream 1528 and may be further configured by the medical practitioner performing the operation or analysis. The touch-screen monitor 1518 enables the medical practitioner to interact with the various modules in the image processing engine 1516 and/or the medical imaging data repository 1524 in order to present a processed video stream 1528 which is suitable for the desired operation, analysis, tissue type, and/or region of interest. The storage device 1520 (e.g., a database, physical storage volume, network storage device, cloud-storage device, etc.) is configured to capture and/or collect the unprocessed video stream 1514 and/or the processed video stream 1528. In certain embodiments, the storage device 1520 further stores the video output displayed on the touch-screen monitor 1518. In further embodiments, the storage device 1520 is configured to upload the data streams along with useful metadata and/or medical information to the medical imaging data repository in order to build and improve the accuracy and usefulness of the medical imaging data repository.

In some embodiments, the camera 106 and the light projector 1506 (e.g., a ring light) are combined into a single unit. In further embodiments, the camera 1512 and the light projector 1512 are used to examine a subject 1526 in vitro. In some embodiments, the camera 1512 and the light projector 1506 are used to examine a subject in vivo in open surgery. In other embodiments, the camera 1512 and the light projector 1506 are collected in and/or adapted by a laparascope for minimally-invasive surgery and/or investigation.

Figure 15B:
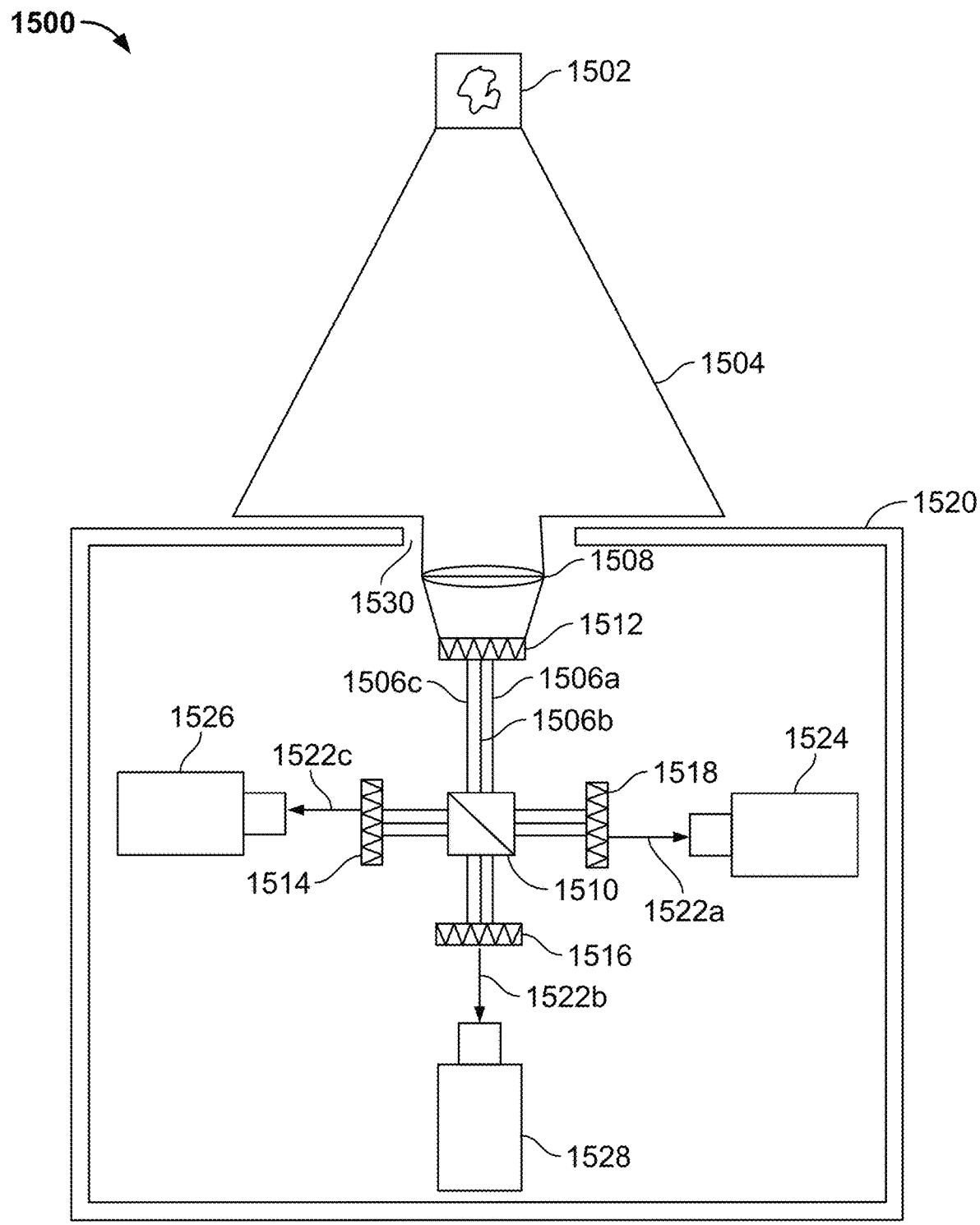
FIG. 15B is an illustrative schematic of a multichannel camera apparatus, according to an embodiment of the present disclosure.

Turning to FIG. 15B, the camera 1512 is configured to generate multiple video signals corresponding to a particular spectral range of visual information. The area of interest is illuminated and excited by the light projector 1536 and the resulting broad spectrum light 1534 comprising the combined spectra generated by the light engine 1502 is collected at the camera aperture 1560. The broad spectrum light is collected by the single-axis lens 1538 and directed onto the broad-spectrum filter 1542, which is configured to substantially eliminate any light but the excitation light. In certain embodiments, the broad spectrum light is first deflected and directed to an additional video sensor in order to preserve the unfiltered visual information collected by the camera 1512. After the broad-spectrum light has been filtered out of the light, the fluorescent light generated by the probe species are directed to a prism 1540. The prism 1540 is a simplified depiction of a prism according to an embodiment of the present disclosure, which may be configured geometrically, texturally, and/or chemically to direct the filtered light 1536a, 1536b, 1536c (collectively filtered light 1536) to the appropriate video sensor. Various examples of prisms according to certain embodiments of the present disclosure are discussed in further detail later. The prism 1530 is configured to split the light into three discrete pathways by which each of the fluorescent spectra may be individually observed. In one embodiment, the filtered light 1536a, 1536b, 1536c represent red, green, and blue light respectively. The filtered light 1536 is directed through the narrow-spectrum red filter 1534a, which substantially eliminates the green and blue components of the filtered light 1536. In certain embodiments, a filter is not needed and the properties of the various prism surfaces are configured to reflect only the desired wavelength of light (e.g., geometrically, texturally, chemically, using air gaps, or by other means) and a discrete narrow-wavelength filter is not needed. The resulting narrowly-filtered red light 1532a is then collected by the video sensor 1534a. The remaining fluorescent light spectra are similarly filtered by narrow-spectrum filters 1534b and 1534c and collected by video sensors 1534b and 1534c to produce substantially green and substantially blue video streams, respectively. These video streams are then combined by the image processing engine and further augmented to enhance the distinction between the various tissue types illuminated in each of the channels, using for example enhanced color distinction between the tissue types detected by each of the sensors.

In certain embodiments, features of the systems and methods described in the following patent applications can be used: "Broad spectrum excitation light and laser based light engine," International (PCT) Publication No. WO2014/081298, published May 30, 2014, "Method and device for detecting fluorescence radiation," Netherlands Patent Application No. 2009124, published Jan. 7, 2014, and "Two-dimensional imaging system, device comprising an imaging system, and method for calculating a parameter for a two-dimensional range," Netherlands Patent Application No. 2010883, published Dec. 8, 2014.

FIG. 16A shows an optical fiber cable 1600 with inner fiber bundles 1610 and outer fibers bundles 1605 in a ring-like setup, the inner fiber bundles 1610 having a smaller diameter than the outer fiber bundles 1605. The fiber bundles are built up of smaller fibers creating a "logical" bundle, wherein each smaller fiber typically receives the same wavelength of light. Multiple configurations of larger and smaller fiber bundles can be used to construct the final fiber cable and different stacking forms can be used like hexagons, random distribution, or others to provide the best efficiency.

FIG. 16B shows the combined fiber cable 1600 of FIG. 16A with attached to it a light module, in the current example an excitation light (e.g., laser or LED) module 1615. The light module 1615 with the attached fiber cable 1600 can be said to form a light engine 1620, outputting the produced light through the fiber cable. The excitation light module 1615 comprises a number of excitation light dies or excitation lights with lenses, with each excitation light or lens butt-coupled to one of the fibers bundles 1605, 1610 of the combined fiber 1600. The light from the excitation light dies or excitation light with lens is thus efficiently coupled into the fiber bundles 1605, 1610 of the combined optical fiber cable 1600.

As illustrated in FIG. 16D, instead of (or in addition to) LEDs coupled into the fiber bundle, solid state laser modules 1630 can be coupled efficiently into a fiber bundle through either butt-coupling or a lens construction. Since lasers are a coherent light source, lasers can be coupled into fiber bundles either through butt-coupling (small fiber bundles) or through a lens system. Depending on the application, either one or the other can be used. For effective coupling of light from a light source into fibers of a fiber bundle, it is advantageous to have the angle of the light adjusted when it outputs the light source, such that a larger field is illuminated. Therefore, the parallel laser beam enters a lens 1635 just before it is coupled into a fiber bundle 1640 such that the light is divergent and hence leaves the fibers of the bundle at the same angles.

A light engine can thus also combine LED and laser light sources.

Furthermore the one or more fiber bundles output from each of multiple excitation light engines 1620 can be bundled together into one larger fiber cable 1625. This is schematically illustrated in FIG. 16C. The assembly of three light engines 1620 and the beginning of cable 1625 thus form a combined light engine 1605.

The fiber cable 1625 receives fiber bundles 1645*a*, 1645*b*, 1645*c* from respective light engines 1620. In an embodiment, outgoing fiber bundles 1645*d*, 1645*e*, 1645*f* are each comprised of fibers from all incoming fiber bundles 1645*a*, 1645*b*, 1645*c*. That way, the incoming light is uniformly mixed in the outgoing fiber bundles 1645*d*, 1645*e*, 1645*f*.

In an embodiment, a plurality of dies or lenses is butt-coupled to the same optic fiber bundle 1605, 1610. In general: a plurality of dies (or lasers) that all emit light at the same wavelengths can be considered as forming a single light source. In an alternative embodiment, one die or lens is butt-coupled to precisely one optic fiber bundle 1605, 1610.

Different excitation light dies can be provided in the excitation light module 1615. For example, green and blue excitation lights can be provided so that some fiber bundles receive green light and others receive blue light.

In an embodiment where laser sources and LED are combined; for example using excitation sources to provide light to the large fiber bundles 1605 on the outside and lasers to provide light to the fiber bundles 1610 forming a centre ring light.

All LEDs and lasers can be individually controlled or by pairs, whichever is appropriate to better control the temperature (this depends on the used source).

Because a light engine according to the description herein makes it possible to easily combine multiple LEDs and/or lasers, the LEDs and/or lasers themselves can be run at lower power, resulting in less generated heat and less output light wavelengths shifts caused by increasing heat, yielding a more wavelength stable light source. A feedback loop with electronics for controlling the temperature and keeping the light sources at a stable temperature is provided in this light engine.

Figure 17:
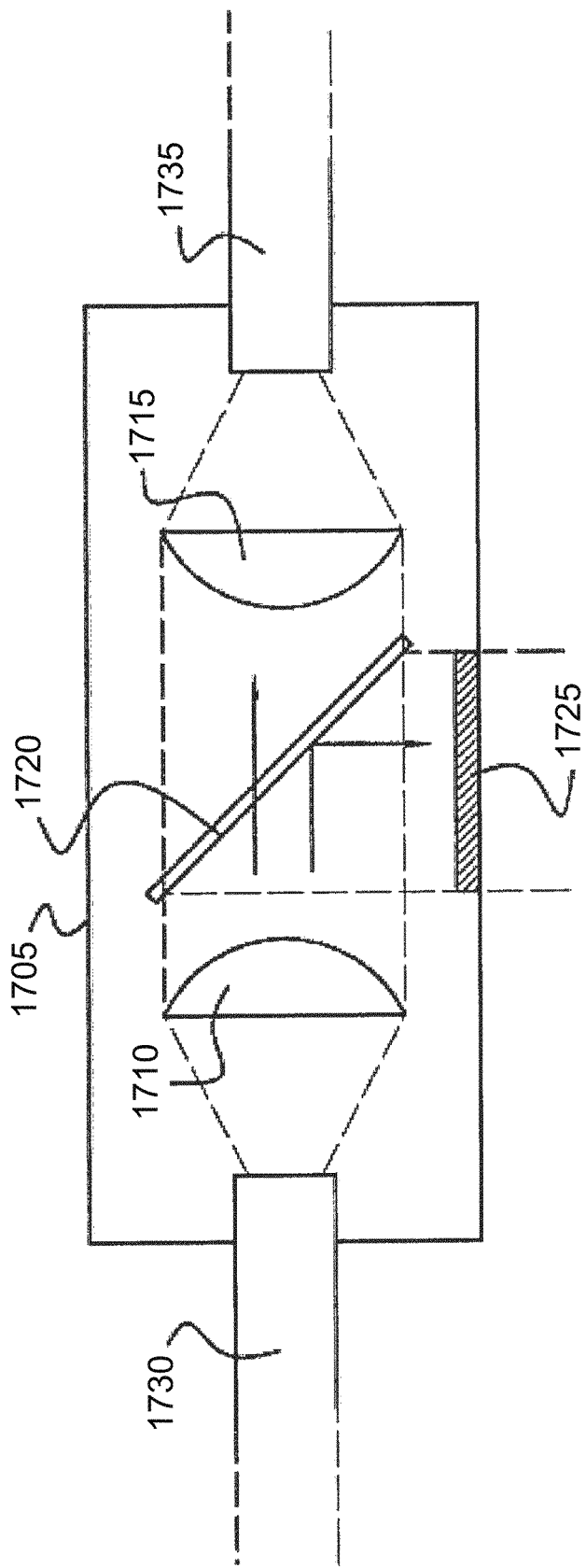
FIG. 17 schematically shows a filter module according to an embodiment of the present disclosure.

When all fiber bundles 1605, 1610 are integrated into the bigger fiber cable 1730, an extra filtering module 1705, shown schematically in FIG. 17, can be added to remove light at unwanted wavelengths or frequencies from the bundle. The filtering module 1705 is connected to at least one input fiber bundle 1730 for receiving light therefrom and to at least one output fiber bundle 1735 for outputting light. The incoming light is focused by lens 1710 into a parallel beam which is directed to a dichroic mirror 1720. The dichroic mirror selectively transmits some of the light (depending on wavelength) and reflects other parts of the spectrum. The transmitted light is collected by a second lens 1715 and focused onto the entrance of the output fiber bundle 1735. The reflected light is discarded, for example by directing it to an absorbing sink 1725. Depending on the transmitting and reflecting properties of the dichroic mirror 1720, a part of the spectrum of the light will be removed. Such removal of a part of the spectrum can be employed to remove, e.g., fluorescence emission wavelengths from broad-spectrum (white light) input light.

Returning to FIG. 16C, using a configuration comprising a number of light engines and combining the output of the light engines in a randomly distributed fiber bundles 1645*d*, 1645*e*, 1645*f* has an added benefit that a ring light connected to this light engine is able to distribute light with all input wavelengths onto the object in an even and evenly distributed way. The even distribution can be optionally improved by using a mixing module.

Using an evenly distributed "flat" light source allows to light a subject with flat, evenly distributed light, allowing for more precise calculations and no non-uniform light distribution effects. When combined with a light distribution device such as a light ring, it is possible to also prevent shading effects such as caused when light comes from one spot. Light sources and devices having an unevenly distributed field of light, such as from a prior art light engine, introduce complexity and errors in calculations, may show up as color rings and bright spots, and may provide shading and reflection which are unwanted effects in typical lighting applications.

Turning to FIGS. 18A-18B, in some embodiments, a light engine that allows combination of light with the same wavelength as well as combining excitation sources which are from the same color but different color bins (color bins are manufacturing controlled peak excitation source wavelengths which are very close together (usually +−5 nm per bin. This makes it possible to combine excitation sources from different bins as well as the same and different wavelengths, to make a high power broad spectrum controlled light engine (FIG. 15A).

Therefore, by using this fiber technology, as illustrated in FIG. 19, a ring light 1915 can be provided. Referring back to the schematic depicted in FIG. 16C, a number of light engines 1920a, 1920b, 1920c provide light via respective optical fibers or fiber bundles 1945a, 1945b, 1945c to central fiber cable 1625. The fibers from bundles 1945a, 1945b, and 1945c are randomly combined to form mixed output fiber bundles 1945d, 1945e, 1945f. If the light engines 1920a, 1920b, 1920c provide identical spectra, the random combination of fibers may be omitted.

Figure 20:
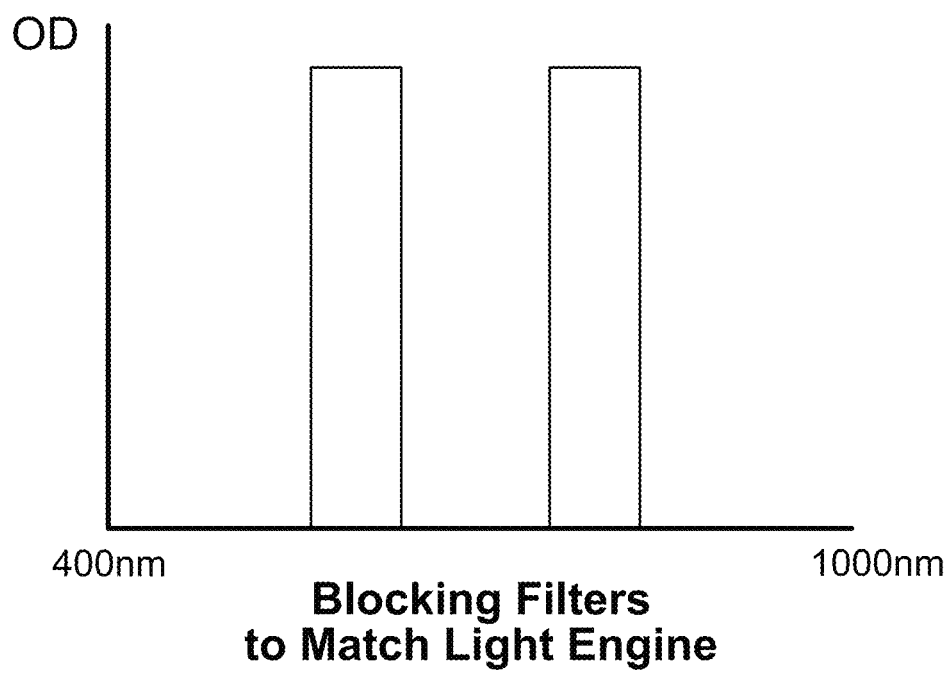
FIGS. 20-22 demonstrate the ability of the filters to match and block light according to an embodiment of the present disclosure.
Figure 21:
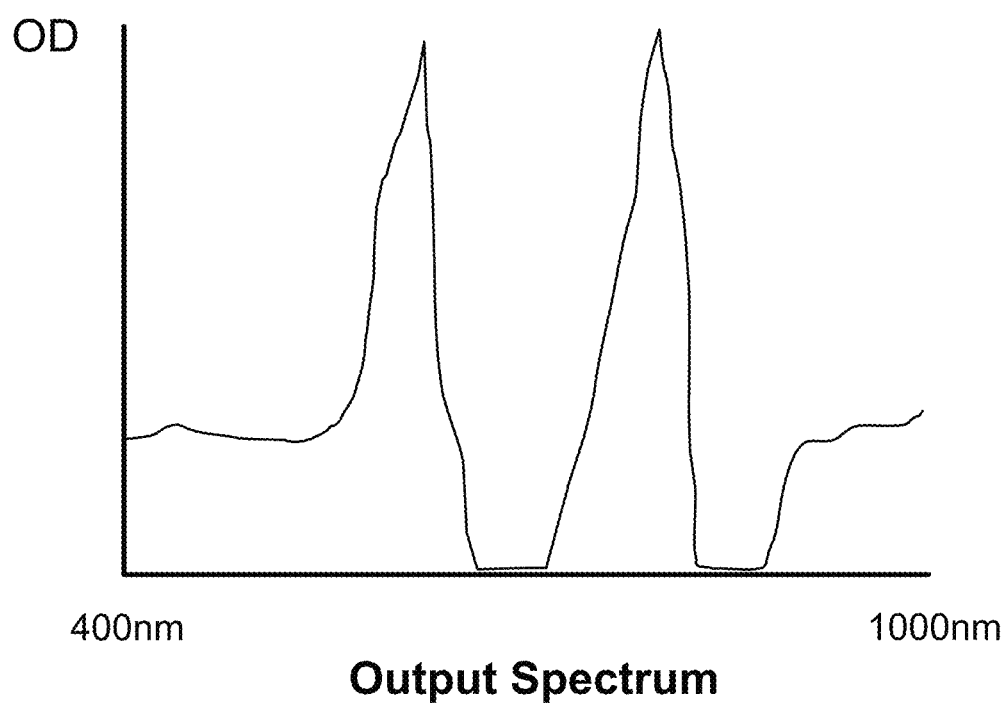
Figure 22:
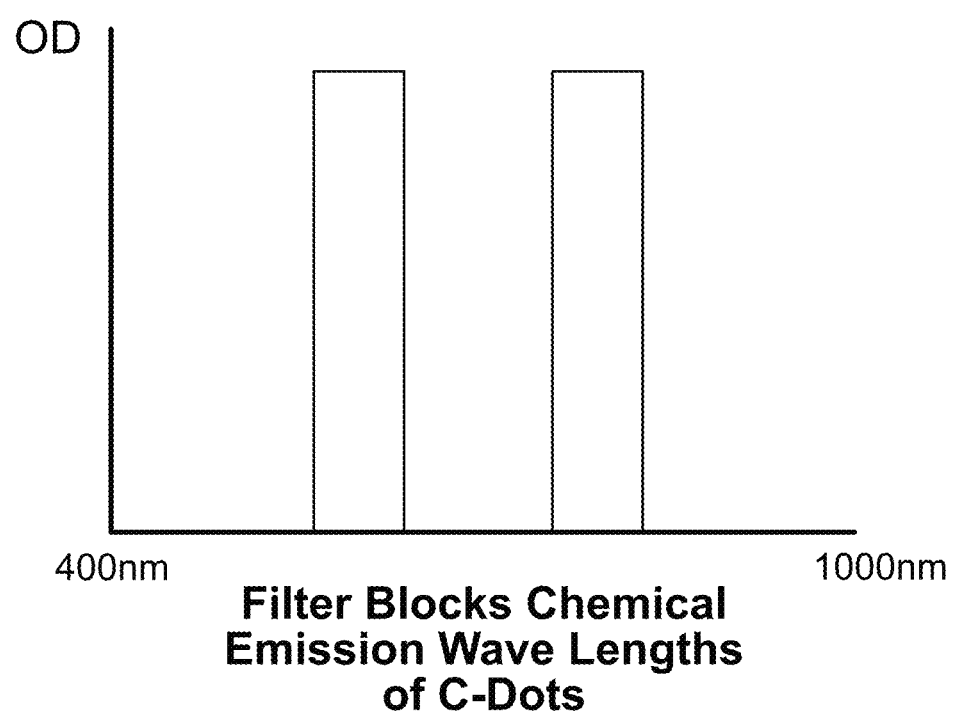

FIG. 20 demonstrates that the multi-band filter can match the light engine and block out higher excitation light from the light source but still be transparent for all other light. FIG. 21 depicts the output spectrum after excitation from the light source with lasers at different wavelengths. FIG. 22 depicts the feature of using a filter at the light engine to block chemical emission wavelengths of a particular probe species (i.e. C or C'dots).

Figure 23:
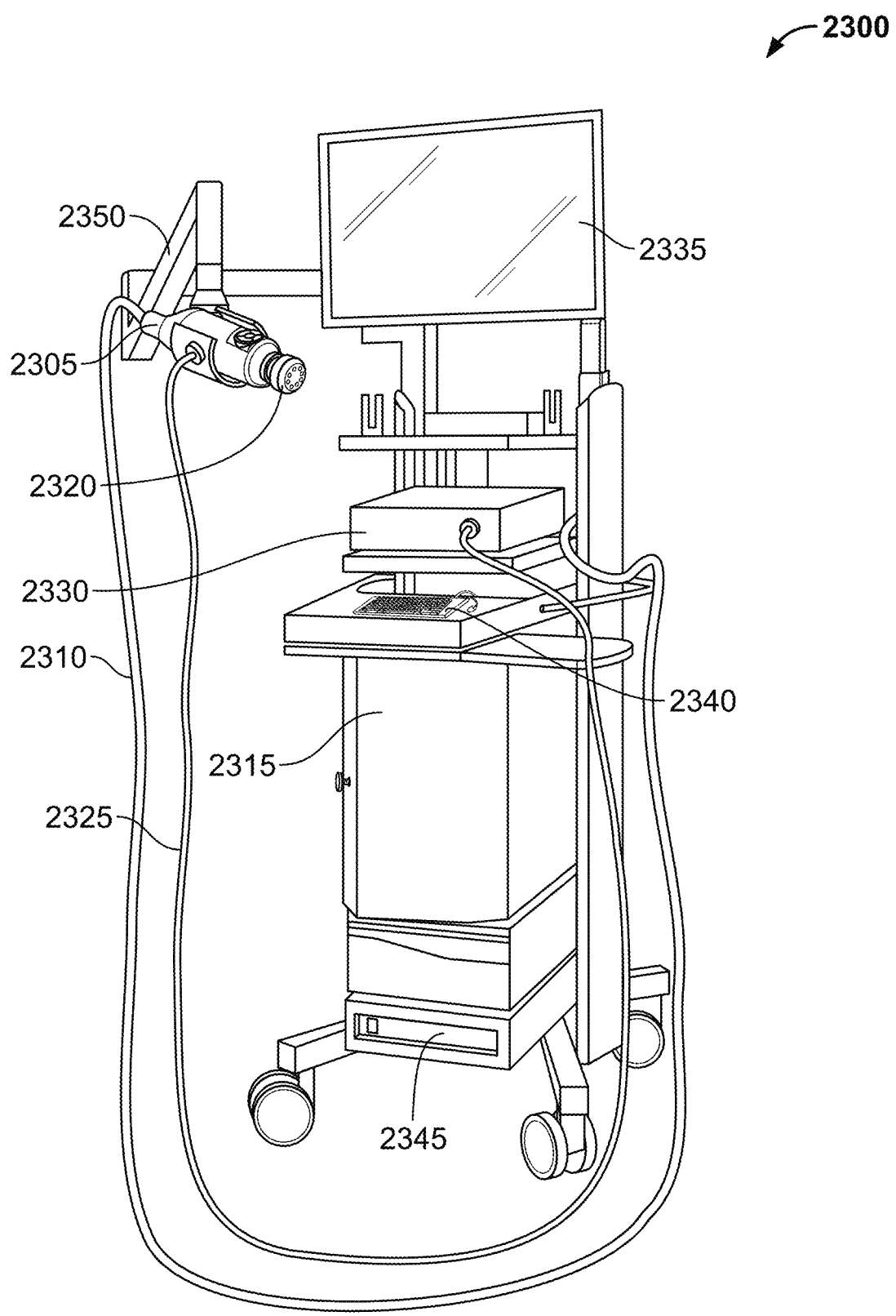
FIG. 23 depicts the ArteMIS™ handheld imaging system.

FIG. 23 displays the optical loop comprising: the 3 channel handheld camera (2305) which is digitally connected with cable (2310) to the communications center (2315) (which contains the processor). Ring light (2320) is connected with cable (2325) to the light engine (2330) which is connected with TTL and RS232 cable to the Communication center (2315) closing the optical loop. The Trolley is also depicted, comprising: the medical display (2335) controlled by the medical keyboard and mouse (2340) connected to the Communications center (2315). All electronics are connected to the mains isolation transformer (2345). Also depicted is the arm (2350) on which the camera (2305) can be mounted or put away in cradle (2335) when not in use.

In some embodiments, detectors can include CCD, CMOS, SCMOS or other detectors that will provide a physical 2D spatial image. Images are received by the system and timed such that one sensor defines the longest exposure time and all other sensors are timed that their relative shorter exposure is synchronized to the end of the longest exposure time to reduce movement artifacts.

Figure 24:
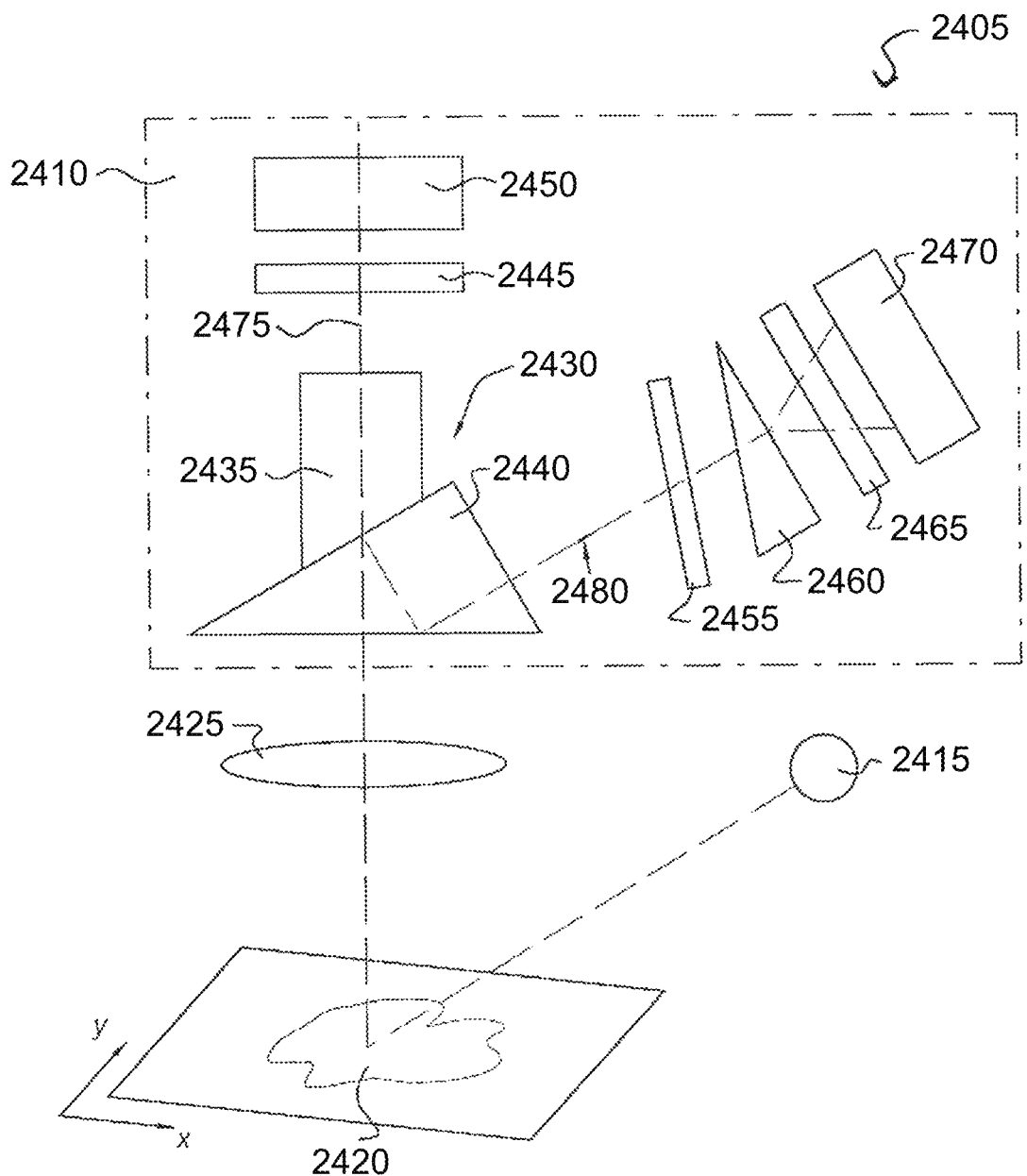
FIG. 24 schematically shows a configuration of a 2D imaging system according to an embodiment of the present disclosure.

FIG. 24 schematically shows elements of a 2D imaging system 2410, according to embodiments described herein. A light source (LS) or light engine 2425 lights a sample 2420, with reflected light focused by lens 2425 on the entrance of imaging system 2410. The imaging system comprises a two channel prism assembly 2430, comprising two prisms 2435 and 2440 configured to split the incident light from lens 2425 into a first channel (2475, emerging from prism 2435) and second channel (2480, emerging from prism 2440). The light in the first channel 2475 is filtered by filter 2445 and detected in two dimensional (2D) sensor 2450. The light in the second channel 2480 is sent through slit 2455, dispersion prism 2460, filter 2465, and finally detected in 2D sensor 2470.

The 2D sensors 2450, 2470 have a 2D sensor array and can detect and output a 2D image. The filters can be configured to select a wavelength or wavelength range. In certain embodiments, the filter 2445 in 2475 is configured to select a narrow wavelength range (e.g. around the emission of the wavelength that is being detected) while filter 2465 in second channel 2480 selects a broad range, e.g. 400-1000 nm. In fact, a filter may not be needed in second channel 2480. The 2D sensor 2450 in first channel 2475 is configured to generated a 2D (spatial, with coordinates x, y) image at the selected wavelength(s).

In the second path, slit 2455 blocks all light except the light along a scan line. The one-dimensional light pattern is provided to dispersion prism 2460, which spatially separates the various wavelengths in the light. The resulting light distribution is passed through filter 2465 and imaged on 2D sensor 2470. The sensor in second channel 2480 thus measures light frequency/wavelength in one direction and a spatial coordinate (x, if the scan line is in the direction of coordinate x) in the other direction.

The imaging system 2410 is calibrated so that it is known which line in the image sensed by 2D sensor 2450 corresponds to the scan line selected by slit 2455. In other words, the spectral/spatial data measured by detector 2470 can be mapped to the 2D spatial data measured by detector 2450. If the wavelengths sampled by second channel detector 2470 comprise all wavelengths sampled by first channel detector 2450, then the calibration can be checked—the 1D (spatial) response obtained by integrating the spectral response as measured by second channel detector 2470 over the range of wavelengths used by first channel detector 2465, should, at least in shape, match the corresponding line in the 2D image of first channel detector 2465.

The sensors 2450 and/or 2470 (possibly combined with a filter 2445, 2465) may be glued to each of the output channels of the beam-splitter 2430 respectively the dispersion prism 2460. This arrangement provides mechanical stability.

The beam splitter, in the present example a prism assembly 2430, splits up the light into at least, but not limited to, two channels (2475, 2480) based on either an energy splitting beam splitter, or a dichroic coating. As mentioned above, second channel 2480 is aligned to first channel 2475 in such a predefined manner that it results in a calibrated co-registered image system that has a known registration between pixels in first channel 2475 and second channel 2480. It is for this registered (or calibrated) line of pixels that for every corresponding pixel in the 2D image a complete spectral response plot can be given.

In an embodiment, the slit 2455 is motorized so that the position of the slit with respect to the sample, and thus the position of the scan line in the 2D image data, can be moved within a certain spatial range.

Figure 25:
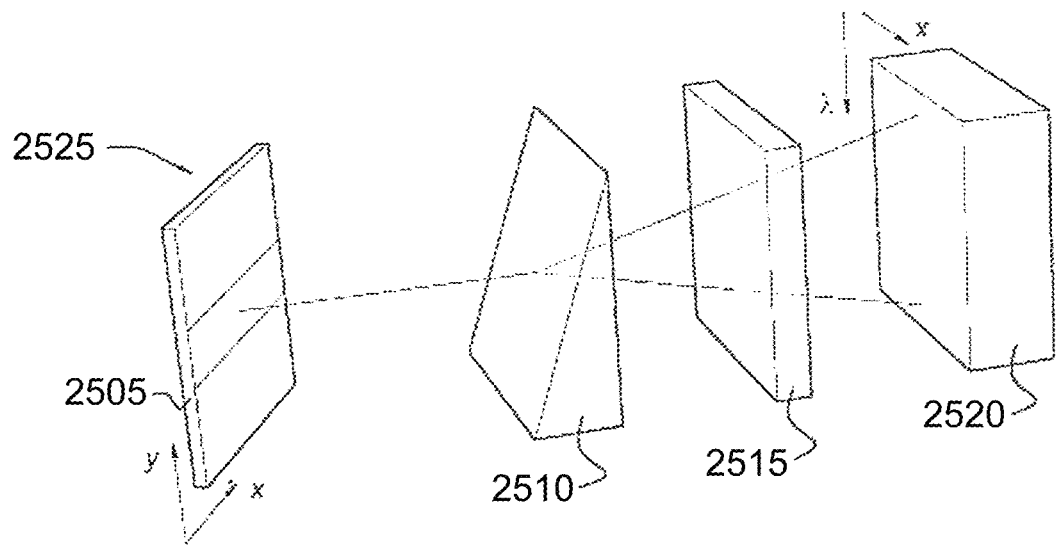
FIG. 25 schematically shows a perspective view of a part of the 2D imaging system of FIG. 24, in accordance with an embodiment of the present disclosure.

FIG. 25 schematically shows a perspective view of an assembly of a slit 2505, a dispersion prism 2510, a filter 2515, and 2D sensor 2520 as may be used in 2525. The slit, which may have a width of 50-200 μm, creates a horizontal line. The light along the line is guided through a dispersion prism 20 which separates the wavelength components and projects these vertically with blue on top and red on the bottom. A 2D sensor 2520 (possibly preceded by filter 2515) is then placed and aligned behind the dispersion prism 2510 so that all the lines of the 2D sensor "sense" a different wavelength. The resolution of each line of the sensor represents about 2 nm, being a little less at the blue side and higher on the red/infrared side (4 nm per line).

Figure 26:
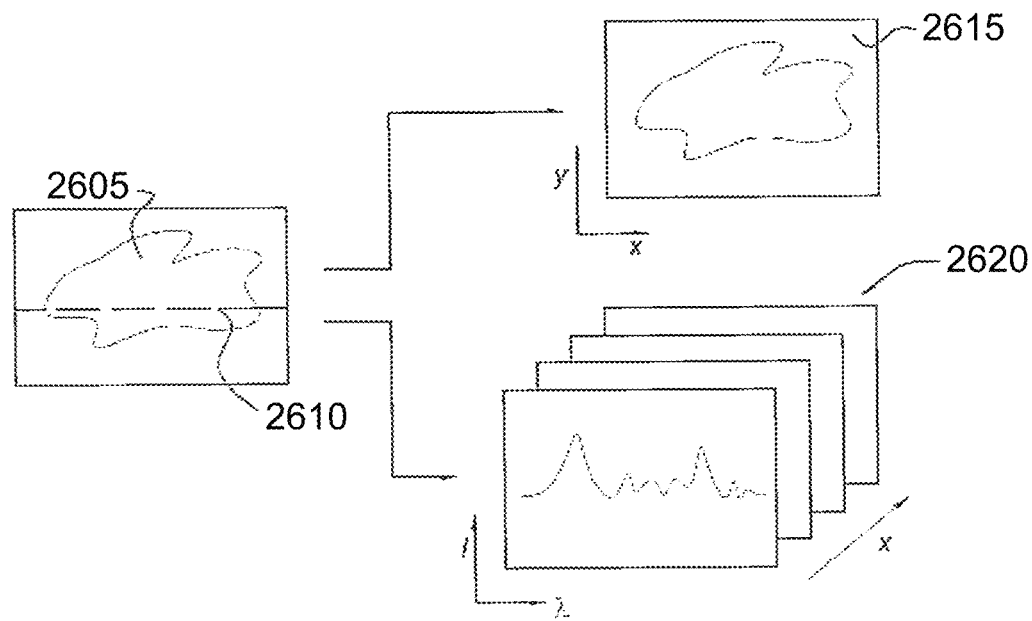
FIG. 26 schematically shows a sample and measured image data according to an embodiment of the present disclosure.

FIG. 26 schematically shows the resulting images of the configuration of FIG. 24. The first channel sensor 2450 generates 2D image 2415 at a selected wavelength. The second channel sensor 2470 generates a set of spectra (intensity I versus wavelength X) 2420, each spectrum corresponding to a point along the scan line (coordinate x). Another way of describing data 2415 and 2420 is that data 2415 is 2D spatial-spatial intensity (x, y, I) data, whereas data 2420 is 2D spectral-spatial intensity (X, x, I) data. Here (x, y, I) indicates a table of measured intensity values with the corresponding x and y coordinates.

The table can be seen as sample points of the function I(x, y), indicating an intensity as a function of coordinates x and y. Likewise, tabular data of (X, x, I) can be seen as sample points of the function I(X, x), indicating an intensity as a function of wavelength and coordinate x. Similarly I(X, y) is a function of wavelength and coordinate y. The wavelength range of the samples may for example be 400 to 1000 nm. The intensities may be absolute values, calibrated values, or may be expressed in relative (arbitrary) units.

In the overview of the sample 2420 in FIG. 24, the dashed line 2410 represents the scan line. The spectral data in set 2420 corresponds to spatial points along this line.

Figure 27:
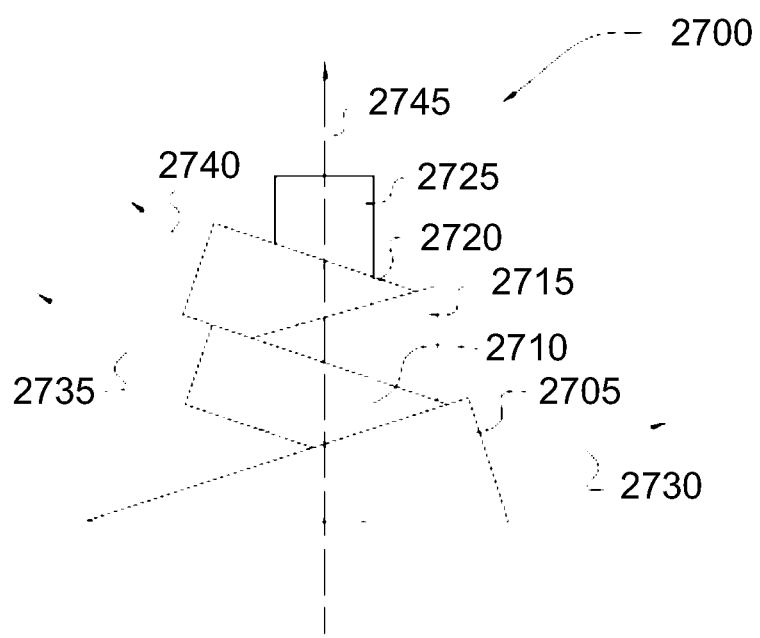
FIG. 27 schematically shows a further 2D imaging system according to an embodiment of the present disclosure.

FIG. 27 shows an example of a four-way beam splitter 2700 that may be used to generate four channels (C1 2730, C2 2735, C3 2740, C4 2745) in an imaging system according to an embodiment of the invention. The beam splitter 2700 comprises five prisms, 2705, 2710, 2715, 2720, 2725.

Figure 28:
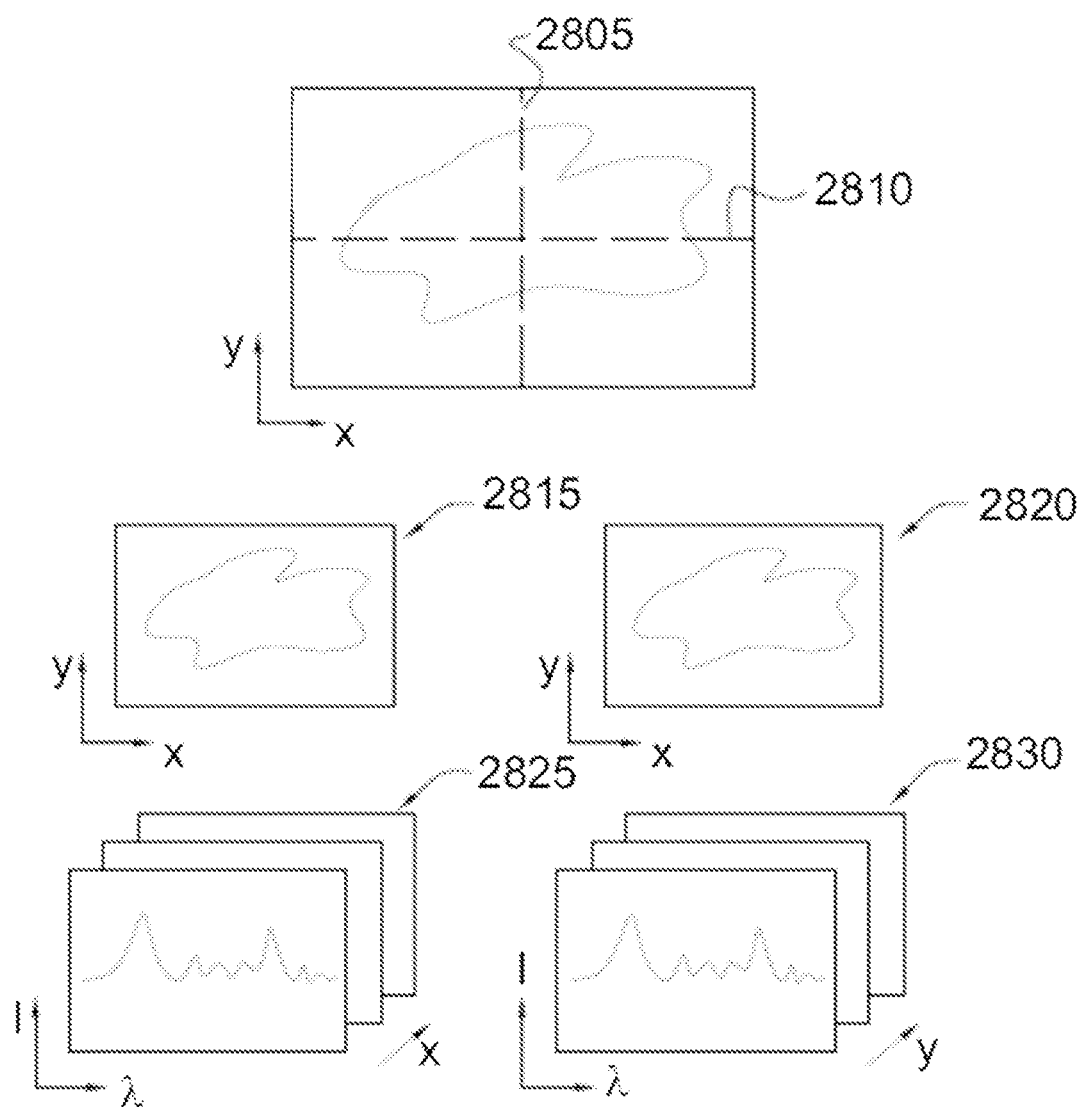
FIG. 28 schematically shows a sample and measured image data according to an embodiment of the present disclosure.

FIG. 28 shows an example of resulting images in an imaging system using the four way splitter 2700 of FIG. 27. Channels C1 2730 and C2 2735 are connected to spectral imaging units, to respectively measure a (X, y, I) data along scan line 2805 and (X, x, I) data along scan line 2810. Channels C3 2740 and C4 2745 are connected to 2D imaging units, to respectively measure (x, y, $_{IIR}$) 2D Infrared data and (x, y, $_{Ivis}$) 2D visible light data. In the example of FIG. 28, the scan lines 2805, 2810 are perpendicular so that a cross-hair is formed.

Figure 29:
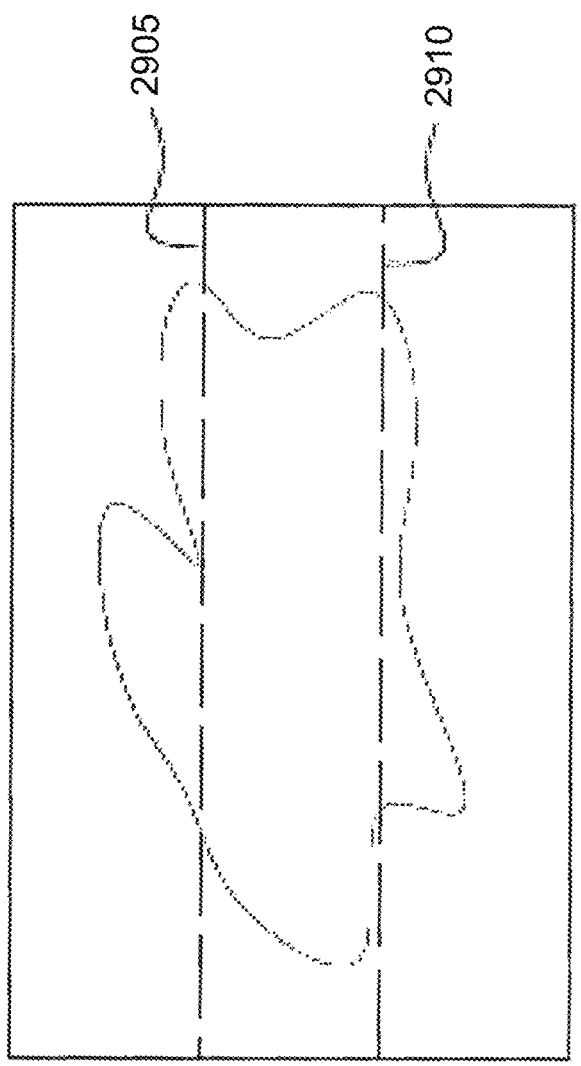
FIG. 29 schematically shows a sample with scan lines according to an embodiment of the present disclosure.

FIG. 29 shows a different configuration of sampling multiple dispersion lines close to each other, using two horizontal lines 2905, 2910 with one or more 2D images of different wavelengths. The main difference with FIG. 28 is thus that now the scan lines 2705 and 2710 are parallel and not perpendicular.

Figure 30B:
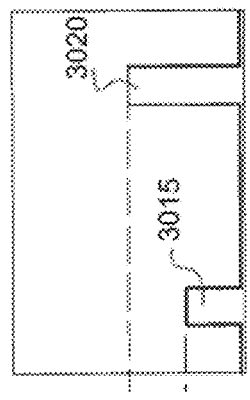
FIGS. 30A-30D schematically illustrate the determination of a ratio according to respectively a prior art method and an embodiment of the present disclosure.
Figure 30D:
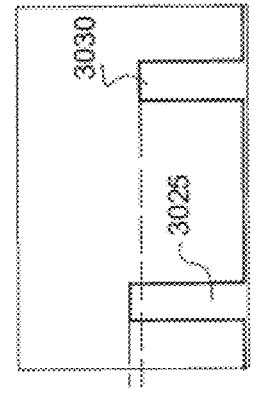
Figure 30A:
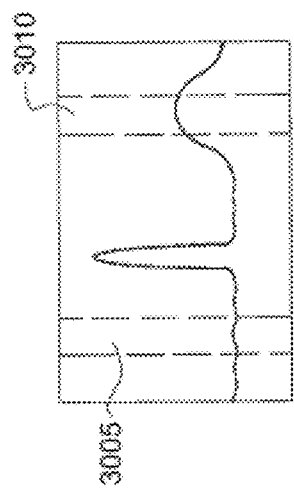
Figure 30C:
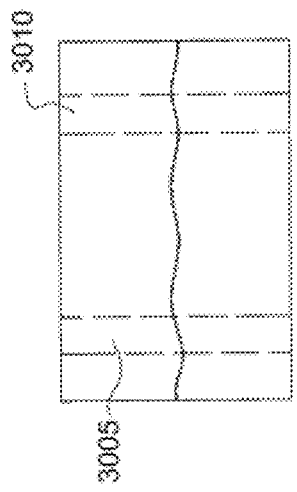

FIGS. 30A-30D illustrate the determination of the ratio R1/R2. If, in FIG. 30A, only the average intensity, for example, in the 670 nm wavelength range 3005 and the average intensity in the 920 nanometer wavelength range 3010 is used, then the presence of the fluorescence radiation around range 3010 will cause an error in the determination of R1/R2. As can be seen in FIG. 30B, the radiation at 670 nm, with average intensity 3015, is more or less correct but the radiation at 920 nanometers, with average intensity 3020, is overestimated resulting in a R1/R2 ratio that is too low. In contrast, the embodiment allows that, along the scan lines at least, the influence of the additional spectra (e.g. ICG excitation and fluorescence) is removed. The intensities 3025 and 3030, corresponding to R1 and R2 respectively, are free from the disturbing influence of ICG, allowing an accurate determination of R1/R2.

Because along the scan lines both the "raw" R2 value 84 and the filtered R2 value 3030 is determined, the fraction of radiation at 920 nanometers that belongs to a detectable signal is known (i.e. the peak of 3020 divided by the peak of 3030). Using this calibration value, the average ("raw") intensities at 920 nanometers as measured over the entire 2D range can be corrected to remove or at least reduce the influence of the ICG spectra.

Figure 31:
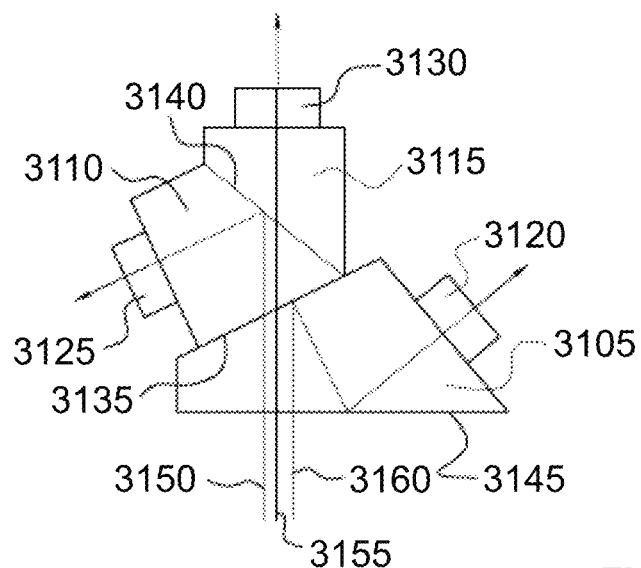
FIG. 31 schematically shows light paths through a dichroic prism assembly, in accordance with an embodiment of the present disclosure.

FIG. 31 schematically shows light paths through a dichroic prism assembly. An exemplary dichroic prism assembly configured to separate light into red 3150, green 3155, and blue 3160 components will now be discussed to illustrate the functioning of such assembly. However, embodiments are not limited to separation into red, green, and blue light. It is contemplated that various wavelengths or wavelength ranges may be used in accordance with various embodiments described herein. It will be clear to a skilled person that a dichroic prism assembly is a means of light separation which can be configured to separate light into arbitrary wavelengths or wavelength ranges as required by a desired application of various embodiments of the present disclosure.

Light comprising red 3150, green 3155 and blue 3160 components enters the assembly through incident surface 3145, shown here as the bottom surface of the assembly. The first transition surface 3135, between the first 3105 and second prisms 3110 comprises a coating that is configured to reflect blue light and transmit red and green light. The blue component B 3160 is nearly totally reflected and, due to the shape of first prism 3105, exits the first prism through the side where sensor 3120 is attached. The applied coating can be a grated refraction index coating.

The green G 3155 and red R 3150 components pass through the first transition surface 3135. The second transition surface 3140, between the second 3110 and third 3115 prisms, is provided with a coating, for example another grated refraction index coating, that reflects red light but allows green light to pass. The red light is thus reflected at surface 3140 and exits the second prism through the face on which the second sensor 3125 is attached. The green light passes through second transition surface 3140 and third prism 3115 and exits through the face on which third sensor 3130 is attached. Each of these paths through the prism assembly is known as a channel.

It is again noted that embodiments of the invention are not limited to the exemplary red 3150, green 3155, and blue 3160 separation. Any configuration of components can be used, as determined by the reflection/transmission wavelength of the coating(s) used. For example, suitable coatings may be used that so that one channel includes light in the wavelength range of 400 to 650 nm (blue, green, and red), another light in the range 650 to 750 nm (red, near-infrared) and a third channel has light in the range 750 to 1000 nm (infrared). In addition, filters may be placed between the exit of the prism and the sensor.

Returning to the example of FIG. 31, the red 3150, green 3155, and blue 3160, components are thus sampled by first, second and third detectors 3120, 3125, and 3130. As mentioned before, these principles apply to any light components, not necessarily red, green and blue, provided that suitable coatings of surfaces 3135 and 3140 and material for prisms 3105, 3110, 3115 is used.

Conventionally, air gaps are often used to provide a second transient surface 3135 suitable for reflecting red light. In some embodiments, a grated refraction index coating may also be used on any transient surface 3135. Such a coating can be in principle applied for any wavelength. Such a coating removes the need for air gaps, which is advantageous since air gaps may be filled with dust when the module is cut.

Figure 32:
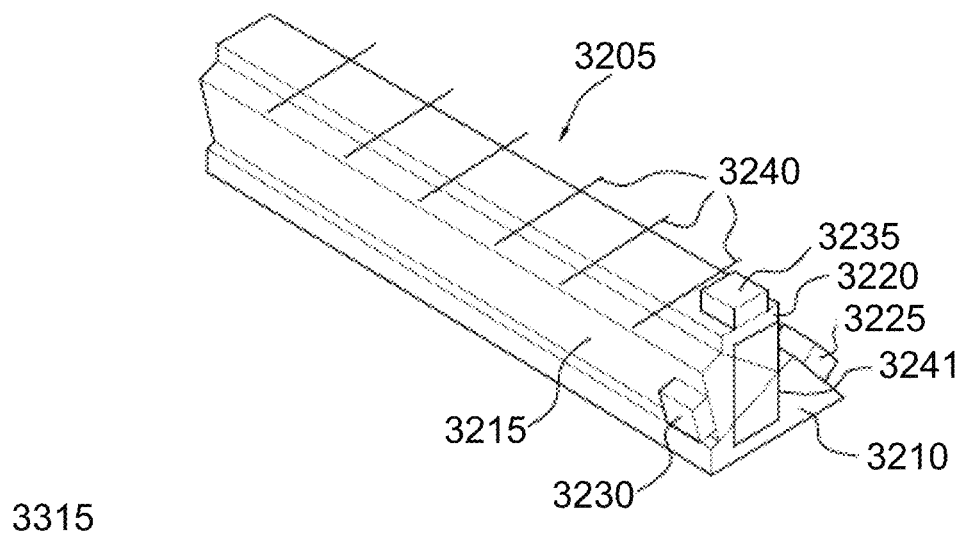
FIG. 32 schematically shows a perspective view of an extended dichroic prism assembly module according to an embodiment of the present disclosure.

FIG. 32 schematically shows a perspective view of an dichroic prism assembly module 3205, comprising three extended prisms 3210, 3215, 3220. Vacuum bonding is performed by pressing the small uncut pieces together. In order to further fortify the bonding, a glass sheet 3210 is attached to each side of the module (front and back). This sheet may later be removed, when the formed dichroic prism assembly for use in an endoscope is formed. The sheet can also remain in the formed dichroic prism assembly.

According to an embodiment of the invention, the dichroic prism assembly module 3205, having at least one dimension unsuitable for use in an endoscope tip is cut along a cutting line 3240.

Figure 33:
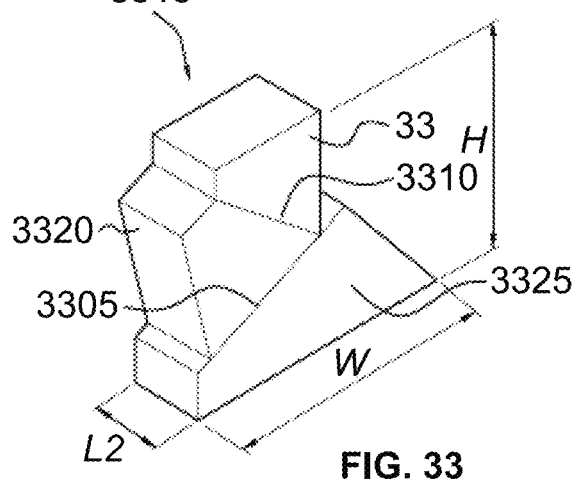
FIG. 33 schematically shows a perspective view of a dichroic prism assembly module according to an embodiment of the present disclosure.

FIG. 33 is an exemplary dichroic prism assembly in accordance with the cutting process described in reference to FIG. 32. The dichroic prism assembly 3315 has dimensions indicated as height H, width W, and length L2. After cutting, at least one dichroic prism assembly 3315 suitable for use in an endoscope tip is obtained. Repeated cuttings will yield a plurality of dichroic prism assemblies 3315.

Figure 34:
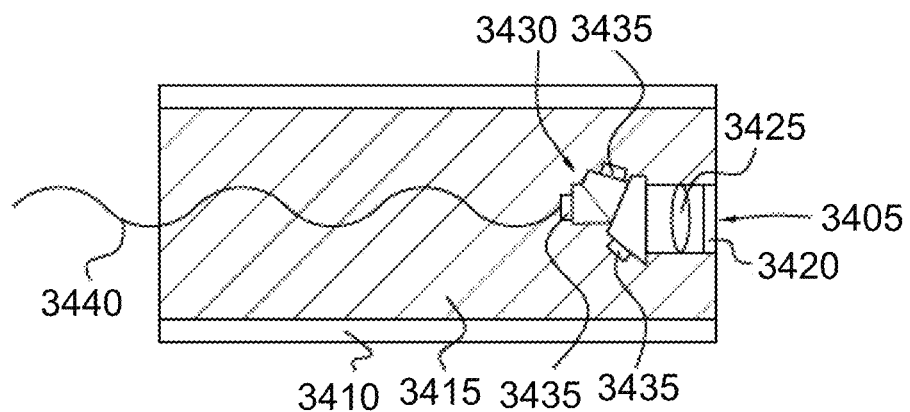
FIGS. 34 and 35 schematically show cross sections of an endoscope tube comprising a dichroic prism assembly according to an embodiment of the present disclosure.

FIG. 34 shows an example of an dichroic prism assembly 3315 obtained by the described cutting process. The assembly 3315 has width W, height H, and length L2. Length L2 is much smaller than the length L of the module 3205 of which assembly 3315 was a part. A typical value for L2 is between 0.5 mm and 2 mm. Typical values for H are between 0.5 mm and 2 mm, and for W also between 0.5 mm and 2 mm.

Figure 35:
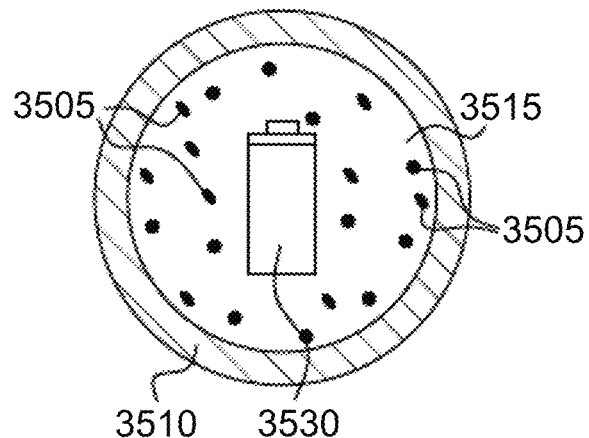

In FIG. 35, a length-wise cross section of an endoscope tip according an embodiment of the invention is shown. The incident light that enters the endoscope tip along incident path 3405 is transmitted through cover plate 3420, focused by a lens 3425 onto a dichroic prism assembly 3430 according to an embodiment of the invention. The assembly 3430 may be obtained by the above described method of cutting a module 3205. The assembly 3430 is dimensioned to be suitable for use in an endoscope tip. The dimensions of the assembly 3430 may be between 0.5 and 5 mm in each direction, preferably between 0.5 and 2 mm or between 1 and 1.5 mm.

The dichroic prism assembly 3430 is provided with sensors 3435. These sensors may comprise Charge-Coupled Devices (CCDs). The sensors may also comprise a chip comprising means for determining a relative or absolute orientation, or rate of change of said orientation, of the endoscope tip. An example is a so-called gyro chip. The endoscope tip may also comprise processing means, for example for processing pixel data from the CCD. Connected to the sensors are signal wires 3440 for carrying a signal from the sensor and/or chip in the sensor away from the endoscope tip, typically to an external signal processing device such as a PC or monitoring device.

In FIG. 35, a cross section of tube wall 3510 is shown. The interior 3415 comprises optical fibers 3505 or bundles of fibers 3505. These fibers may be used to transport light from an external light source, through the transparent front surface 3415 to illuminate an area surrounding the endoscope tip. The reflecting light is then received via the first and second incident paths 3405. Because two incident light paths are provided, the endoscope can be used for stereo imaging.

Figure 36:
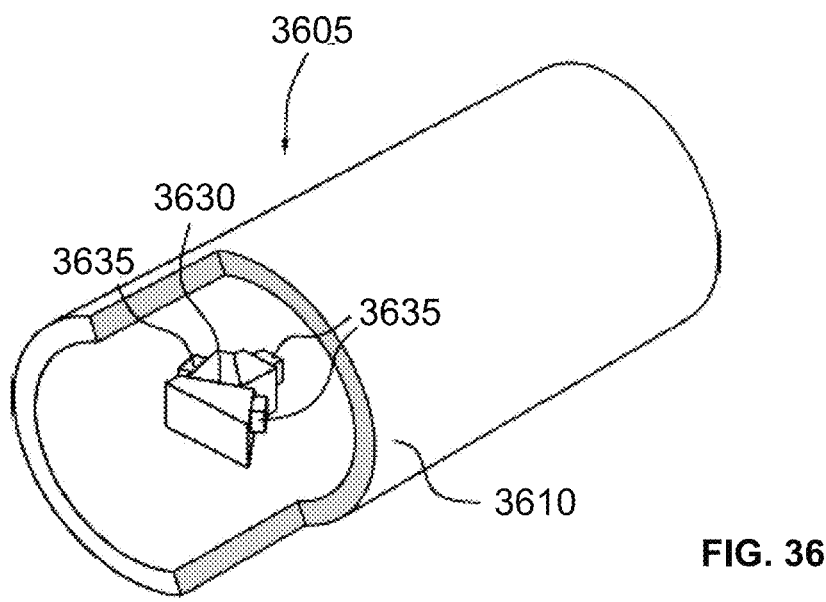
FIG. 36 schematically shows a perspective view of an endoscope tube according to an embodiment of the invention with part of the tube wall removed, in accordance with an embodiment of the present disclosure.

FIG. 36 schematically shows a perspective view of an endoscope tube according the invention with part of the tube wall 3410 removed, and without the fibers 3505, lens 3425 and cover surfaces 3415 and 3420.

The endoscopes according to an embodiment of the invention are, however, not limited to endoscope tips with one incident paths 3405 as shown in FIGS. 34, 35 and 36. Endoscopes with two (e.g. for stereo applications) or three or more incident paths can also be envisaged. Not all paths need to be provided with a dichroic prism assembly according to an embodiment of the invention—only where the light needs to be separated into several components.

Figure 37:
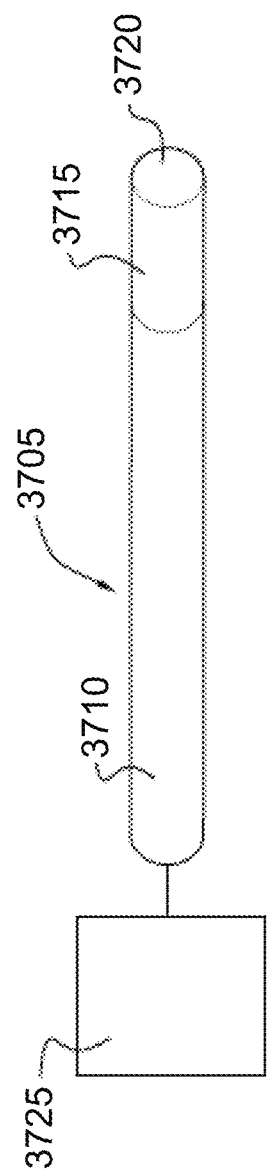
FIG. 37 schematically shows a fluorescence measurement probe according to an embodiment of the present disclosure.

FIG. 37 shows an alternative probe 3705 according to an embodiment. The probe 3705 has an elongated cylindrical body, comprising main part 3710 and distal end or tip 3715. The tip 3715 is provided with a surface 3720 for collecting incident radiation. The incident radiation comprising the fluorescence radiation to be measured will pass through a lens (not shown) in the tip and be collected in a plurality of optical fibers. The fibers will transport the light through the main part 3710 of the probe towards a connected analysis unit 3725. The analysis unit may comprise a wavelength separation unit, such as a dichroic prism assembly, and sensors with which an embodiment may be practiced. An external light source (not shown) is used to excite the fluorescence agent.

In some embodiments, endoscopes or other types of probes such as open systems are used. The light for fluorescence agent excitation may be provided via the system (for example generated in or at least transported through fibers in an endoscope) or externally (for example external to an open system probe). The endoscope or probe may comprise wavelength separation means (such as a dichroic prism assembly) at or near the site of incident radiation collection (i.e. in the tip) or in a connected analysis unit to which the incident radiation is transported (for example using optical fibers).

A data processor can be part of the optical data collection system 102 to pre-process or process image data, and/or a separate image processor can be used to process image data. Background light can be corrected for and calibration performed for repeatability and accuracy of imaging results. Per methods described herein, the detected fluorescent light can be processed to provide a resulting image. The resulting image can be displayed on a standard display. In some embodiments, multi-band filters 104 may be used.

In some embodiments, systems may include a computer which executes software that controls the operation of one or more instruments, and/or that processes data obtained by the system. The software may include one or more modules recorded on machine-readable media such as magnetic disks, magnetic tape, CD-ROM, and semiconductor memory, for example. The machine-readable medium may be resident within the computer or can be connected to the computer by a communication link (e.g., access via internet link). However, in alternative embodiments, one can substitute computer instructions in the form of hardwired logic for software, or one can substitute firmware (i.e., computer instructions recorded on devices such as PROMs, EPROMS, EEPROMs, or the like) for software. The term machine-readable instructions as used herein is intended to encompass software, hardwired logic, firmware, object code and the like. The computer is preferably a general purpose computer. The computer can be, for example, an embedded computer, a personal computer such as a laptop or desktop computer, or another type of computer, that is capable of running the software, issuing suitable control commands, and/or recording information in real-time. The computer may include a display for reporting information to an operator of the instrument (e.g., displaying a tomographic image), a keyboard for enabling the operator to enter information and commands, and/or a printer for providing a print-out, or permanent record, of measurements made by the system and for printing diagnostic results, for example, for inclusion in the chart of a patient. In certain embodiments, some commands entered at the keyboard enable a user to perform certain data processing tasks. In certain embodiments, data acquisition and data processing are automated and require little or no user input after initializing the system.

Figure 38:
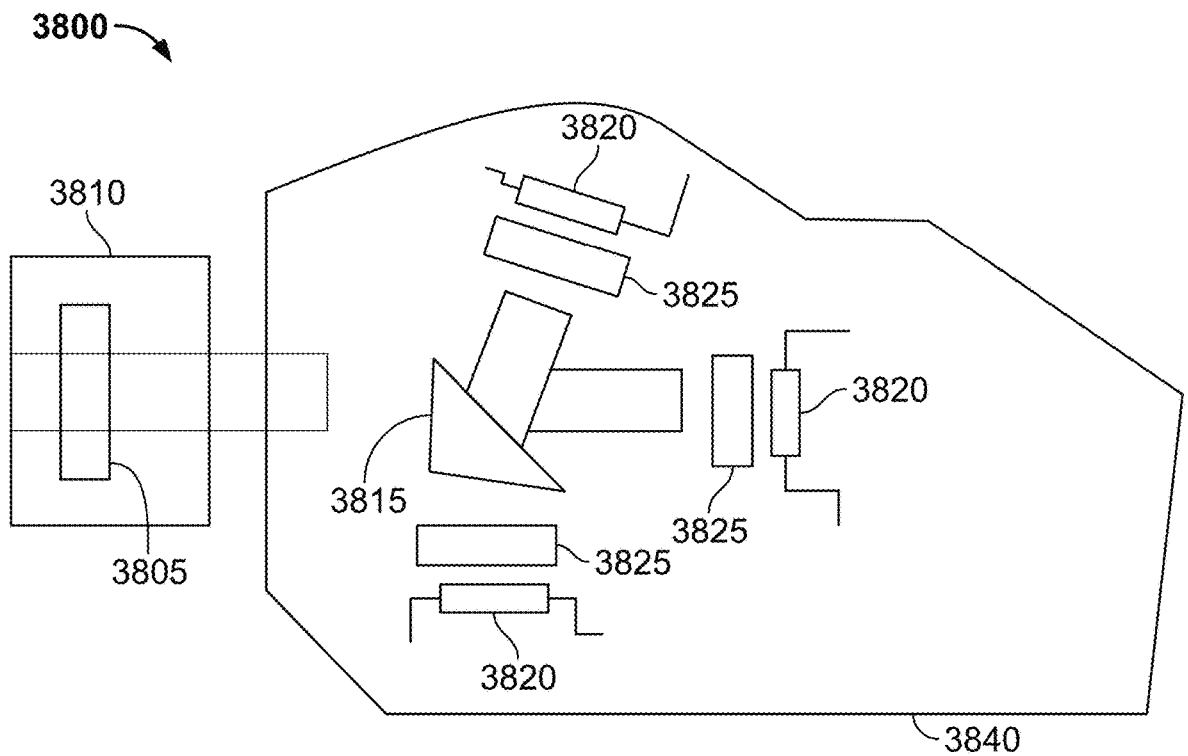
FIG. 38 depicts a schematic of the internal features of a camera head, including the lens, prism, filters and sensors, in accordance with an embodiment of the present disclosure.

FIG. 38 shows a schematic of a camera head 3840 that may be used in various embodiments described herein. In some embodiments, a multi-band filter 3805, other filters 3825, detectors/sensors 3820, a dichroic prism 3815, and a lens 3810 may be used. The prism 3815 separates required light by wavelength to reach each of the n sensors (here, three sensors) by a combination of coated surfaces. The multiband filter 3805 is used to block all the laser excitation light allowing the visible and fluorescent light to pass. In some embodiments, other filters 3825 are positioned in relation to their respective image sensors 3820 to remove any light signals other than the fluorescent and/or visible light of interest. In some embodiments, an entrance filter (e.g., the multi-band filter 3805) is used to block high power laser and/or other light sources.

Figure 39A:
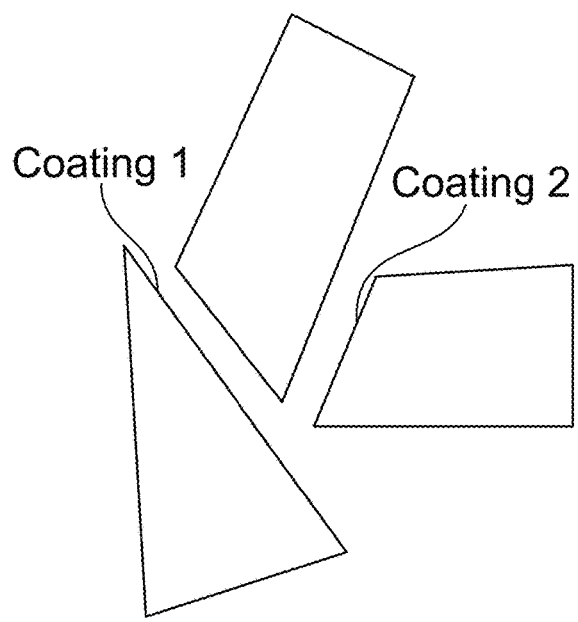
FIG. 39A depicts the arrangement of the dichroic prism and the location of coatings on the prism surfaces, in accordance with an embodiment of the present disclosure.
Figure 39B:
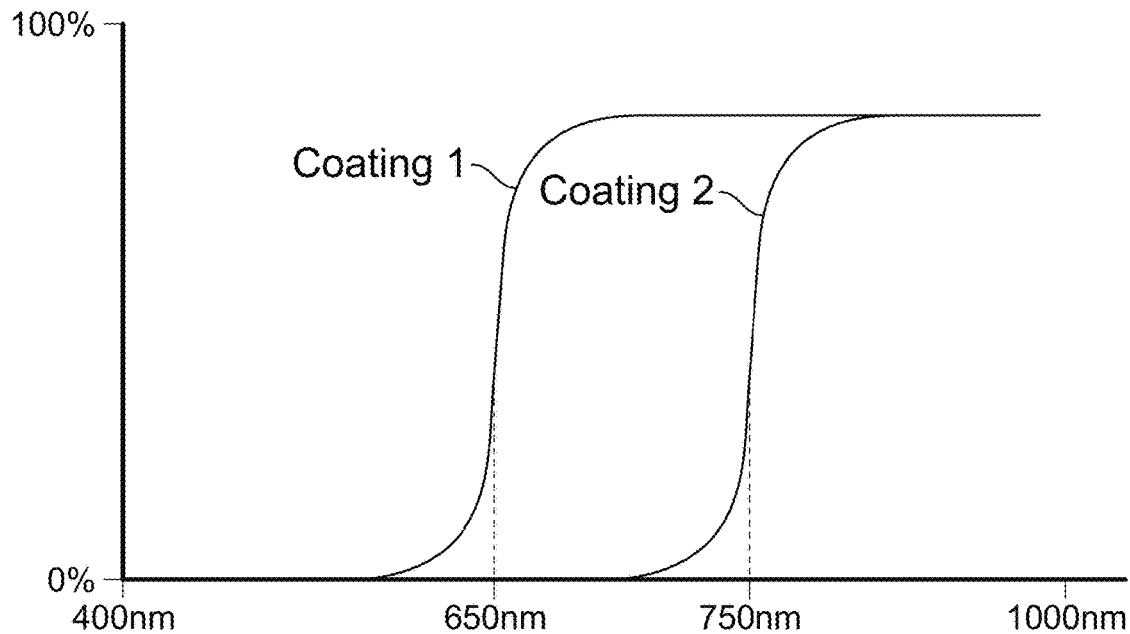
FIG. 39B depicts the effect each coating has on reflected wavelength.
Figure 39C:
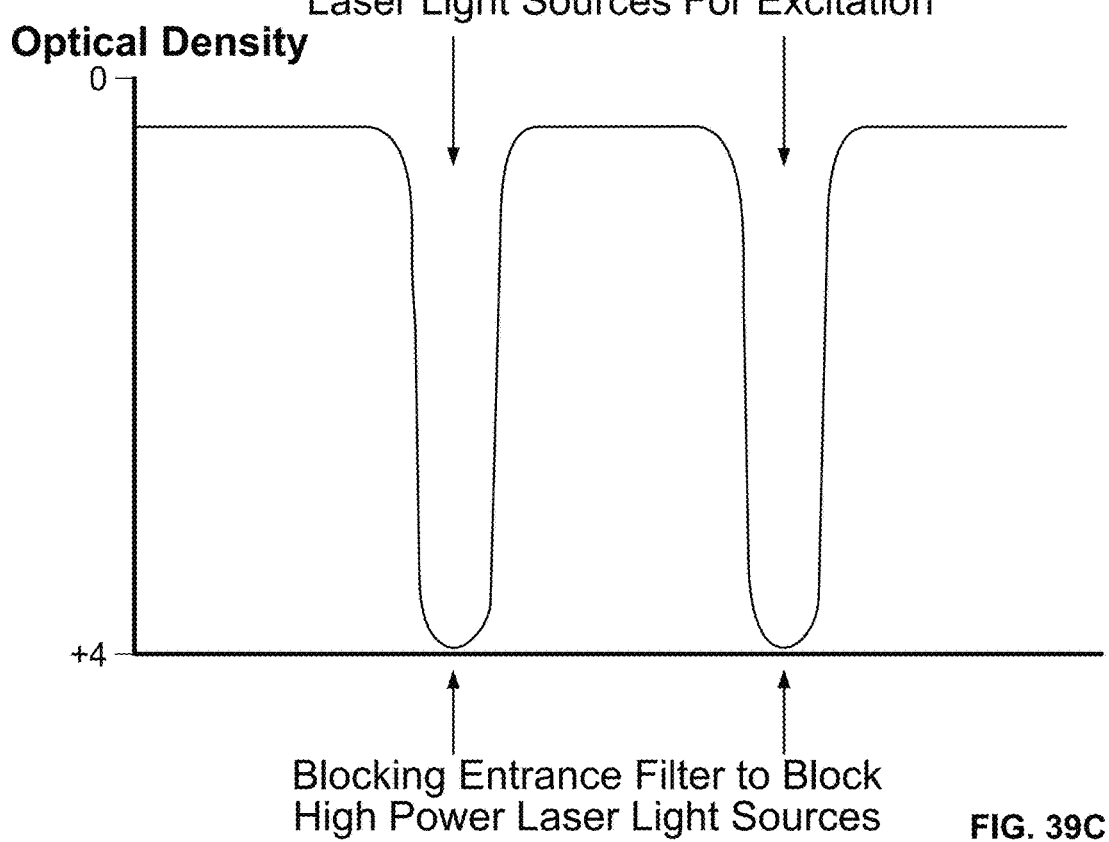
FIG. 39C depicts the ability of entrance filters to block high power laser light sources.

FIGS. 39A-39C depict the role of the prism and filters in operation of certain embodiments described herein. FIG. 39A depicts the arrangement of the dichroic prism and the location of coatings on the prism surfaces. FIG. 39B depicts the effect each coating has on reflected wavelength. FIG. 39C depicts the ability of entrance filters to block high power laser light sources. FIG. 39A is a schematic depicting the arrangement of elements of the dichroic prism and the location of two coatings on the prism surfaces. From FIG. 39B, the first coating in this example affects a transition to reflection at around 650 nm, and the second coating affects a transition to reflection at around 750 nm. FIG. 39C demonstrates the use of an entrance filter to block light from the high power laser light sources.

Figure 40A:
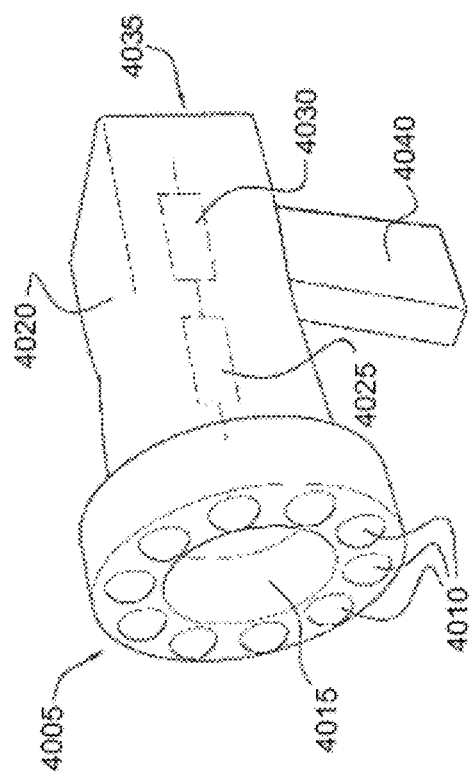
FIGS. 40A and 40B schematically show a measurement device according to an embodiment of the invention, in accordance with an embodiment of the present disclosure.
Figure 40B:
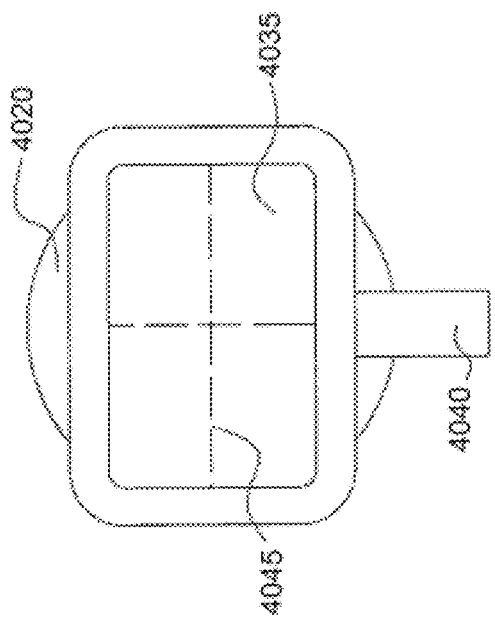

FIGS. 40A and 40B schematically show a measurement device 4005 according to certain embodiments. The device 4005 comprises a lens 4015 for receiving light from a sample. The lens 4015 is surrounded by excitation sources 4010 forming a ring light for lighting the sample. Filters can be placed before the excitation sources or output fibers to control the light that is sent to the studied sample. In an alternative embodiment, the light is provided by lasers or via light fibers which transport the light from a distant light source to the device 4005. The excitation sources or alternative light source(s) will emit light at a suitable wavelength for the application of the device. It is possible to provide multiple sets of light sources in the ring light for various applications. It is also possible to make the ring light module exchangeable, so that a suitable ring light module can be installed for an application of the device 4005. The device 4005 further has a housing 4020 attached to the ring light and a handle 4040 for holding the device 4005. Inside the housing 4020, the device comprises a imaging system 4025 and a processing unit 4030. At the back surface, opposite the lens 4015 surface, the device may have an LCD display 4030 (FIG. 40B) connected to the processing unit 4030. The display 4030 may be a touch panel, so that the user of the device can interact with the processing unit 4030 via the touch panel.

In operation, light from the sample will be collected by lens 4015 and sent to the imaging system 4025. The processing unit 4030 analyses the data collected by the sampling units of the imaging system, and provides an output picture. In the example of FIG. 40B, the system 4025 comprises one 2D sampling unit and two spectral sampling units. The display shows the 2D image and the scan lines corresponding to the two spectral sampling units. In addition, the 2D image may show the extrapolated parameter value as calculated by the processing unit as overlay on top of the 2D image (for more details on the calculation see FIG. 44).

In some embodiments, the camera system may resemble the schematic of the camera device shown in FIG. 41. In some embodiments, the camera may be fastened to a holder as depicted in 4105. In some embodiments, the camera system may be composed on multiple components 4110 (i.e. the light engine, camera sensor and processing unit, and laparoscopic tools.)

Figure 42:
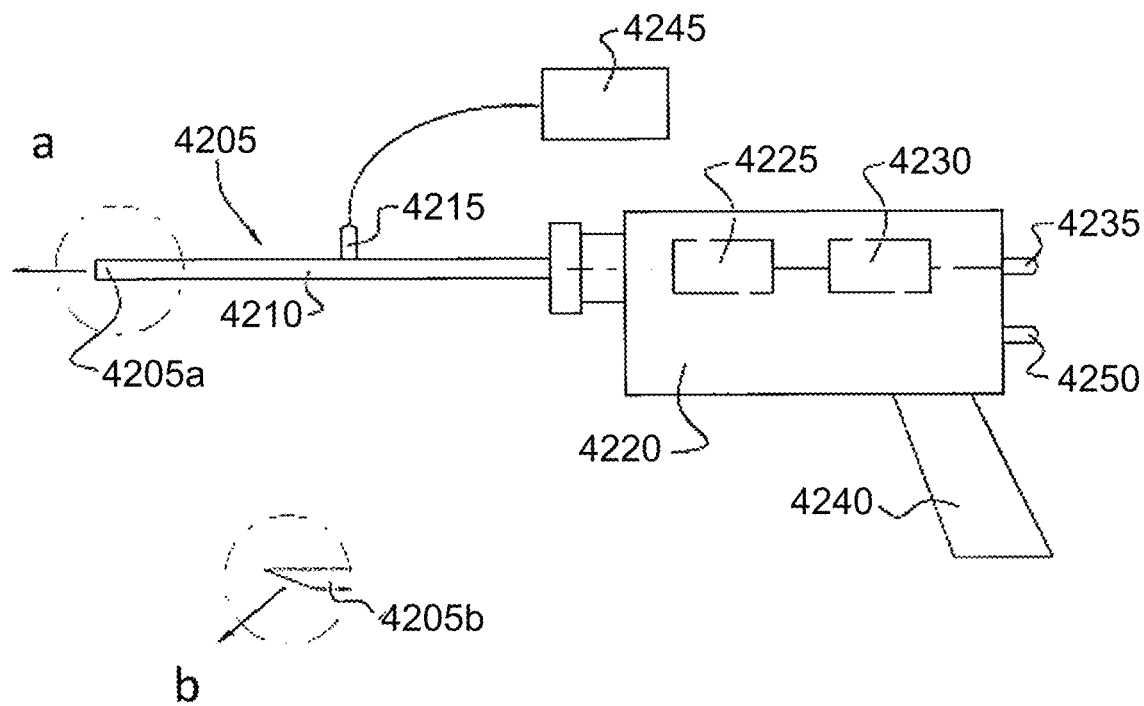
FIG. 42 schematically shows a laparoscope according to an embodiment of the present disclosure.

FIG. 42 schematically shows a laparoscope 4205 according to an embodiment. The laparoscope has an end 4205a comprising a lens. Alternatively, a diagonal end surface 4205b with lens may be provided. The laparoscope 4200 has an elongate body 4210 with a connector 4215 for coupling in light from a light engine 4245. The laparoscope 4205 has a main housing 4220 connected to the elongate body 4210 and a handle 4240 for holding the laparoscope. The housing 4220 comprises an imaging system 4225 and a processing unit 4230. The housing further comprises a connector 4235 for connecting to an external display and a connector 4250 for connecting a power source.

When connected to an external display via connector 4110, the laparoscope 4005 functions analogously to the measurement device of FIGS. 40A and 40B, where the external display takes the place of display 4045 (FIGS. 40A, 40B), the light engine 4245 takes the place of the ring light, and the lens in ending 4210a or 4210b takes the place of lens 4015.

Signal Processing

Figure 43:
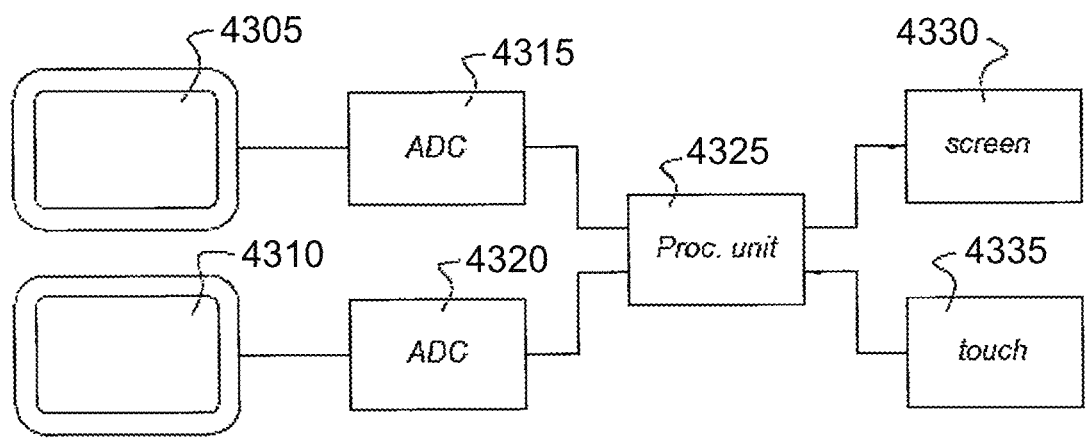
FIG. 43 schematically shows a processing device according to an embodiment of the present disclosure.

FIG. 43 schematically shows a processing device according to an embodiment, such as may be used in the devices of FIGS. 40A, 40B, and 41. The 2D sensor units 111 and 112 output an analogous signal which is digitized by Analog-to-Digital-Convertors (ADCs) 113 and 114 respectively. The digital signals are analyzed by processing unit 115, which is connected to a touch panel comprising display 116 and touch sensor unit 117. The ADC may be integrated in the sensor, as is for example done in CMOS sensors.

Figure 44:
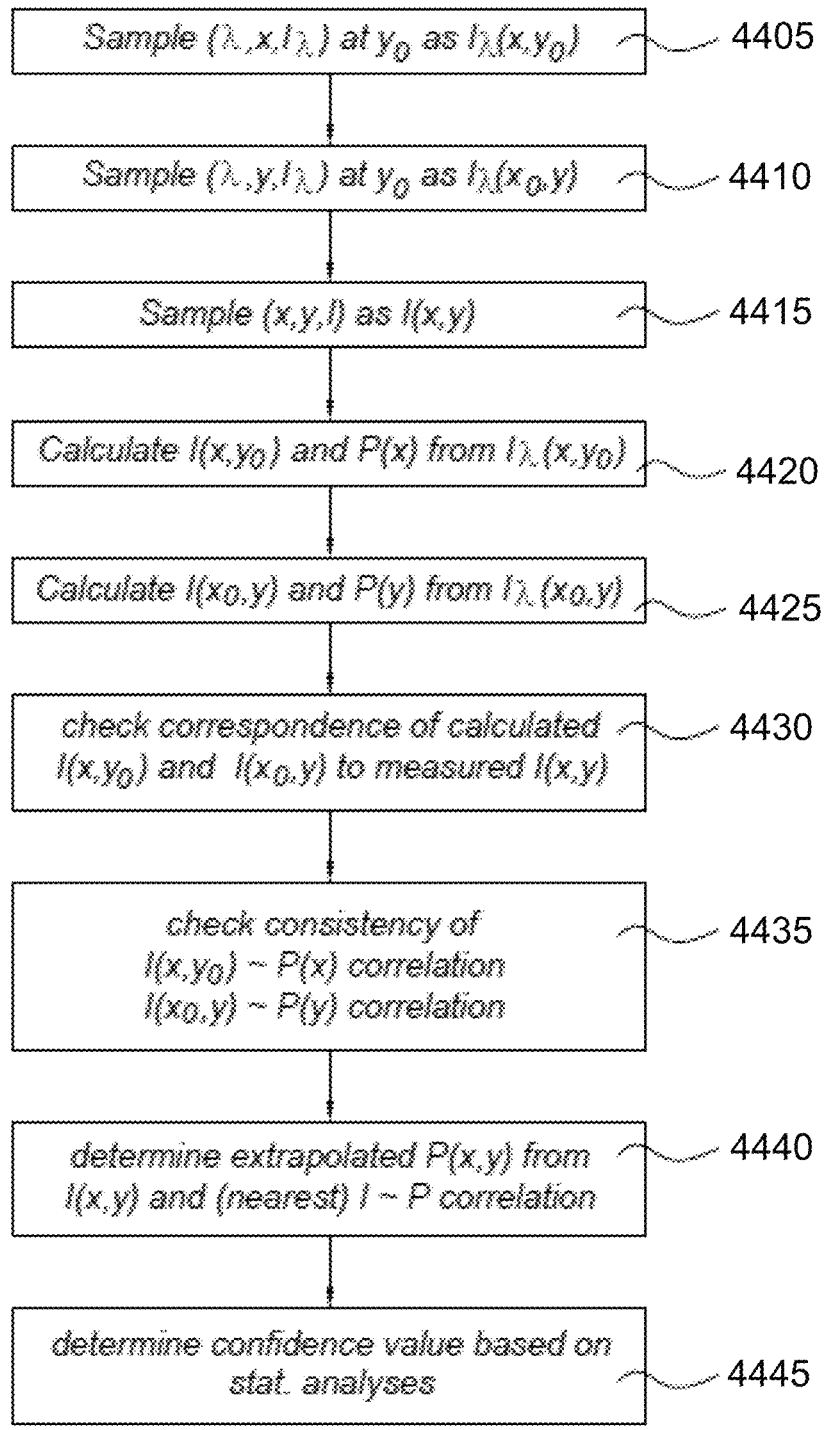
FIG. 44 shows a method for determining a parameter according to an embodiment of the present disclosure.

FIG. 44 schematically shows a method 120 for determining a parameter P(x, y) as a function of location (x, y) in the sample, according to an embodiment. The parameter P can be any measureable quantity that can be determined from a spectrum measurement. It is noted that the particular order of the steps in method 4400 is generally not important. Many steps can be performed in arbitrary order, provided of course that the necessary data is measured before it is processed. An optional step, not shown in FIG. 44, is to perform a relative or absolute measurement for environment lighting, so that the influence of environment lighting on the determined (spectral) intensities can be separated in a further processing step.

The example of FIG. 44 focuses on an exemplary imaging system having one 2D sampling unit, providing (x, y, I), and two spectral sampling units, providing (x, x, I) and (x, y, I). The sampled data can be represented as a sampled mathematical functions I(x, y) (as sampled by the 2D sampling unit) and $I_x(x, y0)$ and $I_x(x0, y)$ (as sampled by the two spectral sampling units). Here the subscript x in $I_x$ indicates that the intensity is provided as a function of wavelength x. Value x0 represents the x value of the vertical scan line (see e.g. line 51 in FIG. 28) and y0 represents the y value of the horizontal scan line (see e.g. line 52 in FIG. 28). In steps 3205, 3210, and 3215 the sampled data for functions I(x, y), $I_x(x, y0)$, and $I_x(x0, y)$ is collected, respectively.

In step 4420, data representing function I(x, y0) and P(x, y0) is calculated from $I_x$(x, y0). I(x, y0) may be calculated by integrating function Ix(x, y0) over the range of wavelengths that is sampled by the 2D image sampler used to obtain I(x, y). In practice, the integral will be evaluated using a weighted sum of $I_x$(x, y0) for a number of frequency samples. P(x, y0) is calculated according to the method for determining parameter P. The calculation of P may comprise a spectrum separation (through e.g. curve fitting) as disclosed in reference to FIGS. 30A-30D. In general, the calculation may comprise curve fitting and calculating relative and absolute peak intensities. For example, often the ratio between two peak intensities is a parameter to be determined. Step 4425 is similar to step 4420, except now I(x0, y) and P(x0, y) is calculated from $I_x$(x0, y).

In step 4430, a first consistency check is done. The values I(x, y0) as calculated should, while accounting for any background radiation that may have been removed from the spectral measurements during processing, correspond to the measured values of I(x, y) along the line y=y0. The same holds for I(x0, y): these calculated values should correspond to the measured values of I(x, y) along the line x=x0. Step 4430 is optional, but may advantageously serve to detect errors in measurements or calibration.

In step 4435, a second consistency check is done. The correlation between the calculated I(x, y0) and P(x, y0) values and the calculated I(x0, y) and P(x0, y) values is checked. Like intensities I should give like parameter values P, otherwise the assumption at the basis of the extrapolation of P(x, y) is not valid. The correlation can also serve as input for a statistical analysis of the confidence interval of an extrapolated P(x, y) value.

The extrapolated values P(x, y), or dataset (x, y, P), is determined in step 4440. Using I(x, y) as input, the correlation between I(x, y0) and P and/or the correlation between I(x0, y) and P is used to estimate P(x, y). Various methods can be used to determine P(x, y) based on I(x, y) and P(x, y0) and P(x0, y). In particular, the calculated values of P at points close to (x, y) can be given a greater weight than P values calculated for more remote points.

In optional step 4445, a confidence value or interval is calculated, indicating the expected error in P(x, y). Depending on the statistical methods used, the skilled person can apply standard statistical techniques for calculating such a confidence value or interval.

In the above description of method 4400, a cross-hair configuration of two scan lines has been used. It will be clear to a skilled person that the method may also be modified to be applied to calculating P(x, y) for any number of scan lines in any configuration.

It may be that more than one parameter P can be calculated from the spectral data $I_{o_\lambda}$. For example, let intensity I1 be indicative of parameter P1, and intensity I2 indicative of parameter P2. An imaging unit that is configured to measure two 2D images (x, y, I1) and (x, y, I2) and any number of scan lines $I_{o_\lambda}$ can then be used to calculate extrapolated values for P1(x, y) and P2(x, y).

It is an advantage of the method of FIG. 44 and its variants that it allows real-time display of calculated and measured parameters P on top of (as overlay of) visible light image data. The overlay is synchronized with the visible light image data, so that even samples with internal movement can be measured. In addition, the extrapolation is based on an analysis of the full spectrum, so that any background radiation not contributing to the peaks of interest can be effectively disregarded in the calculation of P.

Figure 45A:
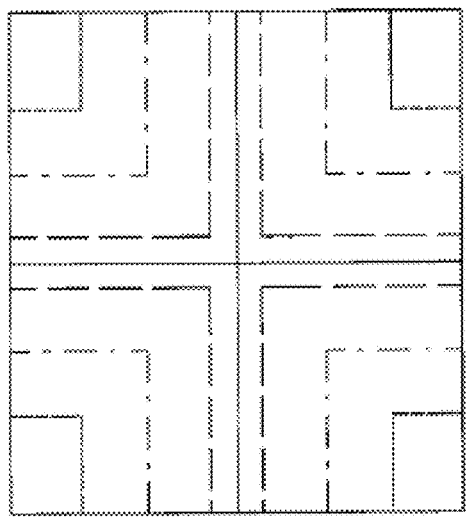
FIGS. 45A and 45B schematically show confidence areas of a parameter determined according to an embodiment of the present disclosure.
Figure 45B:
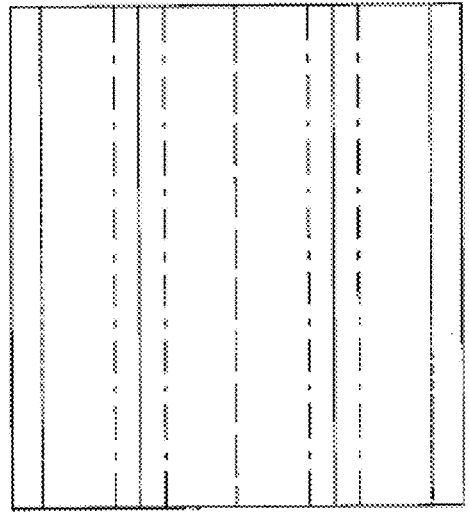

To further illustrate the comments made in reference to steps 4440 and 4445, FIGS. 45A and 45B schematically illustrate the estimated accuracy (confidence value) levels of the 2D parameter determination. The drawn lines represent the scan lines, with FIG. 45A having the scan line configuration of FIG. 29 and FIG. 45B having the alternative scan line configuration of FIG. 28. The dotted lines, located closest to the scan lines, represent lines in the 2D range where there is relatively high confidence in the extrapolated parameters. The dashed lines represent lines in the 2D range where there is a reduced confidence in the extrapolated parameters. It will be clear to a skilled person that this is but one metric that can be used to determine confidence intervals. Other mathematical methods may be used to link a position (x, y) in the 2D range to a confidence value based on the relative location of the one or more scan lines. In addition, the internal consistency of the spectral measurements can be a factor in determining the confidence value. For example, if all spectral measurements are nearly identical, this is an indication that the 2D range is of a fairly homogeneous composition and confidence in extrapolated values will be high. In contrast, if the spectral measurements have a strong spatial dependency along a scan line, this can be an indication that the sample composition is spatially inhomogeneous, and the extrapolated values may have low confidence. For example, the standard deviation of a parameter as determined from the spectral measurements can be factor in determining the confidence value of the extrapolated parameter values—the confidence value can be taken to be inversely proportional to the standard deviation.

Figure 46:
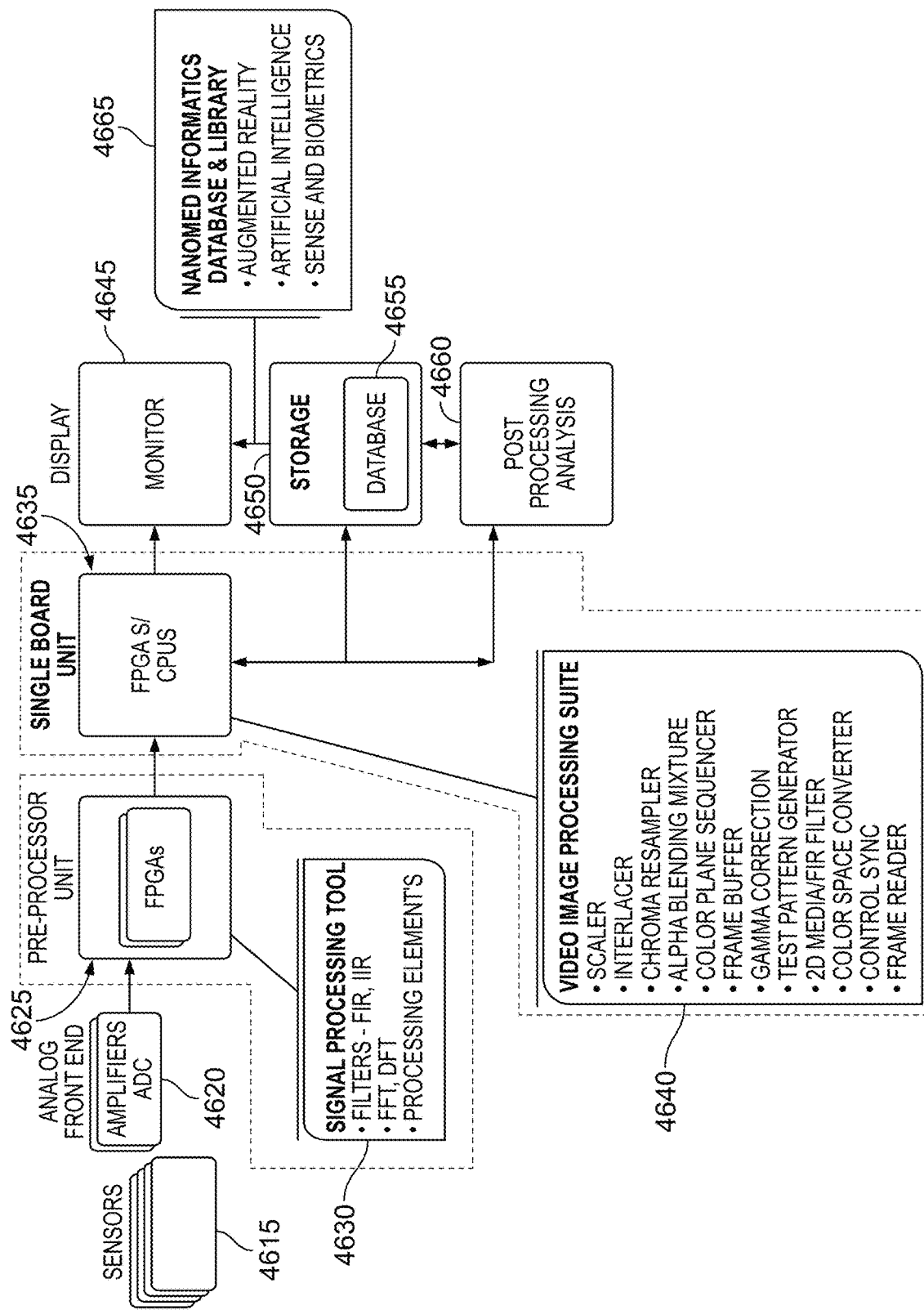
FIG. 46 schematically shows a block diagram of the system camera including, but not limited to, a pre-processing, processing, display unit and its compatibility with a medical imaging data repository for system integration, in accordance with an embodiment of the present disclosure.

FIG. 46 is an exemplary schematic of video processing operations performed on each of the one or more video streams collected by the camera, in accordance with an embodiment of the present disclosure. In certain embodiments, the present disclosure provides for methods and systems for simultaneously detecting radiation of different wavelengths from different probe species within a subject and discriminating between signals received from each probe species. In some embodiments, this is accomplished with an apparatus comprising a light source configured to deliver multiple excitation wavelengths of light to excite a plurality of fluorescent reporters, thereby producing fluorescent light at two or more distinguishable wavelengths; a prism configured to direct light received through a lens onto a plurality of spatially-separated detectors such that said detectors can measure, in real-time, different emitted signals simultaneously; and a processor configured to process signals corresponding to the detected fluorescent light at the two or more distinguishable wavelengths to provide images of fluorescence within a subject. In some embodiments, this involves multiplexing of signals.

The intrinsic programmable nature of Field Programmable Gate Arrays (FPGAs), Application Specific Integrated Circuits (ASICs), and/or CPUs of the pre-processor 4625 enables improved decision-making, performance capabilities, and computational processing speeds that can be achieved based on the digital signals acquired through sensors 4615 and data converters 4620. The preprocessor unit 4625 is designed to contain re-configurable FPGAs that introduce flexibility into the computational approaches used for processing data, as well as enable the insertion of advanced optimization capabilities in the form of signal processing tools. These tools include the use of digital filters and mathematical algorithms to convert acquired optical signals to the frequency domain. Integration to the remainder of the processing unit 4635 is achieved by combining additional FPGAs with multicore CPUs; this hardware combination enables the expansion of image processing capabilities, such as image enhancement and restoration, image and data compression, wavelet transformation and color space conversion. In addition, advanced modeling algorithms are implemented for 2D image generation through FFT functions of the frequency domain that sharpen and spatially de-blur acquired images while reducing noise in real-time. The inclusion of an FPGA processor within the Single Board Unit 4635 eliminates delays in processing and display, and facilitates the addition of communication protocols to the system, conversion from wired to wireless access, and expanded storage capabilities on a range of media plug-in devices. Importantly, these components are internally integrated into the camera system pipeline (versus off-line processing/display), which further increases processing speeds, frame rates, and dynamic range. The pipeline integration further enables user-friendly GUI controls including predefined and manual settings for light engine power control, and other camera controls, such as gain and exposure time, display controls, image orientation functions and selection of multiple video displays according to the user preference.

The analog front end 4620 processes video signals collected by the one or more sensors 4615. The analog front end 4620 amplifies the collected analog video signals and converts them to digital video streams. In various embodiments, the high speed of FPGAs enable synchronous operation so that pixels captured via the various channels of video data correspond to an identical time of capture. After digital conversion the video streams are directed to pre-processor unit 4625. The pre-processor unit 4625 comprises one or more FPGAs, ASICs and/or CPUs configured to modify the signal using for example, finite impulse response (FIR) and/or infinite impulse response (IIR) digital filters, fast Fourier transforms (FFTs) and/or discrete Fourier transforms (DFTs), and other pre-processing elements. After pre-processing, the digital video signals are further modified by FPGAs, ASICs, and/or CPUs (the single board unit 4635) as part of a video image processing suite 4640 configured to perform video image processing. In certain embodiments, the video signals are multiplexed and/or demultiplexed either prior to or after the pre-processing and/or image processing operations. Examples of video image processing operations performed by the single board unit 4635 include scaling, interlacing, chroma resampling, alpha blending mixture, color plane sequencing, frame buffering, gamma correction, test pattern generation, 2D media FIR filtering, color space conversion, control synchronization, frame reading, image enhancement and restoration, image and data compression, wavelet transformation and color space conversion. In certain embodiments, a processed video signal is directly displayed on a monitor 4645 and/or stored in storage medium 4650 (e.g., a network storage device, a physical or logical storage volume, a cloud-computing device, etc.), for example, in a database 4655. In some embodiments, two or more of the processed video signals are multiplexed for display. In certain embodiments, a broad-spectrum video signal (i.e., unfiltered video or filtered video comprising all light except the excitation light) is multiplexed with one or more of the filtered fluorescent video signals. In further embodiments, the video signals, either multiplexed or individually, are subjected to further post-processing analysis by a post-processing analysis unit 4660, such as an FPGA, ASIC, and/or CPU. The post-processing analysis unit is configured to perform various analytical operations on the video streams, including but not limited to edge detection, automatic deconvolution, fluorescent reporter flow tracking, and spatial texture based classifiers to decipher the tissue type and heterogeneity associated with each of the plurality of image pixels for visualization. In various embodiments, one or more of the pre-processing, image processing, and post-processing operations are performed on individual FPGAs, ASICs, and/or CPUs. In some embodiments, the distinction between processing units is merely symbolic and the operations are performed on the same device. In certain embodiments, the various operations performed in this exemplary description are considered to be in, or are actually performed at a different stage of processing than herein described. In some embodiments, each of the video signals is processed on discrete hardware elements, up to and including individual FPGAs, ASICs, and/or CPUs for processing operation (for example, filtering, fourier transforms, interlacing, gamma correction, and compression are each handles on a discrete device.) In other embodiments, multiple processing operations are performed by a single device, and may or may not be limited to analysis of a single video channel.

The multichannel video data collected presents a unique and useful method of extracting highly precise visualization of the subject of the application. By combining the visual information from each fluorescent spectra it is possible to dramatically reduce the effect of background light and other unwanted data. In one embodiment, two or more video signals are represented as S1 and S2. Let P1 and P2 be the wavelength-dependent fluorescence radiation and B be the background emission. Since the background emission is substantially wavelength independent, the collected signal S1 is approximately equal to P1+B, and the signal S2 is approximately P2+B. By performing linear operations on the signals the background emissions B can be eliminated so that a signal comprising substantially no background emission, S3, can be displayed. In further embodiments, more signals at various wavelengths improve background emission removal. In other embodiments, various fluorescent species are administered to the subject, wherein the species are more readily absorbed by certain tissue types in the subject (e.g., cancer tissue, nerve tissue, etc.) Based on this information, the post-processing analysis unit is enabled to visually discriminate between the tissue types and provide a visualization that emphasizes the tissue types being displayed.

Graphical Enhancement

In one embodiment, a tissue type T1 (e.g., normal tissue or a particular type) and a cancer tissue C absorb a fluorescent species F1 that provides light emissions of wavelength W1. A second species F2 with wavelength W2 is readily absorbed by a tissue type T2 and the cancer tissue C. Since only the cancer tissue C will present fluorescence of wavelengths W1 and W2, tissue exhibiting fluorescence of only W1 and W2 may be omitted from display by the post-processing analysis unit, providing a visualization of only the cancer tissue C. This is roughly analogous to the binary operation W1 AND W2. In another embodiment, the fluorescent species F1 and F2 are independently absorbed only by the target tissues T1 and T2, respectively. Similarly, the use of various fluorescence species with appropriate tissue absorption properties (corresponding to the desired tissue visualization) and various analogous binary operations or combinations thereof (such as AND, NOT, OR, XOR) provides enhanced tissue visualization and analysis based on the corresponding tissue absorption properties of the fluorescent species. In some embodiments, combinations of two, three, or more fluorescent species enable more complex combinations of tissue absorption properties (e.g., T1 AND T2 NOT T3, etc.). In a further embodiment, each of the tissue types of interest are absorbed by a unique fluorescent species. In one embodiment, a nerve tissue T1 and a nodal tissue T2 absorb two distinct fluorescent species F1 and F2 respectively. An embodiment of the multichannel apparatus herein described facilitates detection of each of the species F1 and F2 in separate video channels. Thusly, a first channel C1 represents the fluorescent emissions associated with the nerve tissue T1, and a second channels C2 represents the fluorescent emissions associated with the nodal tissue T2. In a further embodiment, the post-processing analysis unit enhances a visual representation of the area of interest with a particular color or visual texture (e.g., red) associated with the nerve tissue T1, and second color or visual texture (e.g., blue) with the nodal tissue T2, enabling a practitioner to easily and efficiently identify the corresponding tissue types in real-time. Such enhanced visualization facilitates a practitioner to more precisely remove only the desired tissue (e.g., the nodal tissue) while avoiding accidental removal of the non-desired tissue (e.g., the nerve tissue). In various embodiments of the present disclosure, leveraging the tissue absorption properties of various fluorescent species enables the post-processing analysis unit to perform image enhancement operations that clearly and efficiently visually discriminate between multiple tissue types using for example, different colors or visual textures (e.g., display nerve tissue in red and nodal tissue in blue).

Medical Imaging Data Repository

The medical imaging data repository 4665 (e.g., the Nanomed database) is a computer or other electronic device configured to provide database-assisted analysis on the area of interest using one or more of the video signals at various stages of processing (using, for example, an unprocessed video signal, a pre-processed video signal, an image processed video signal, and/or a multiplexed video signal). The video signal(s) used for database-assisted analysis may vary depending on the application of the present disclosure that is being performed. In certain embodiments, analysis of the appropriate video signals is performed directly by the medical imaging data repository 4665. In other embodiments, analysis is performed by the post processing analysis unit 4660 and information in the medical imaging data repository 4665 is retrieved and/or requested as needed. The medical imaging data repository 4665 provides the practitioner performing the operation or investigation with the benefit of large volumes of information on the subject of the application, in some embodiments, in real-time, e.g., permitting advantageous intraoperative implementation. The medical imaging data repository 4665 is configured to augment the video displayed on the monitor 4645 with useful information such as enhanced color distinction between targeted tissue types, surgical guidelines, magnitude of deviation from objectively normal tissue formations, etc. By using artificial intelligence methods, the medical imaging data repository 4665 is enabled to identify the subject of a video stream, retrieve information related to the subject of the video stream for display, and augment the video stream with useful information. In some embodiments, the medical imaging data repository 4665 is configured to perform sense and biometric analysis on the subject of the video stream.

In a further embodiment, each of the data collected, as part of a particular study, operation, investigation, or analysis, are tagged with a unique identifier and annotated. These data used in the construction and expansion of a database for optically-driven or optical-PET driven cancer nanomedicine studies. The database contents can include text (i.e., particle type/composition, ligand, animal model, dose/volume of injectate), optical/PET imaging parameters (i.e., max pixel intensity, % ID/g), camera performance parameters (i.e., gain, exposure time), nodal fluorescence spectral signatures (signal distribution), histology (tumor burden) or other feature-based strings or binaries. As a more expansive database is developed, optimization of data queries (i.e., specific types of data retrieval) are performed using ODBC (Open Data Base Connectivity) Applications Programming Interface (API). The processing of queries on the medical imaging data repository 4665 is accelerated by inclusion of an FPGA on the coprocessor board. An augmented reality tool interface is integrated with the database to provide computer generated artificial intelligence based sensing and biometrics for real-time comparison or information on the region of interest or subject of interest.

In addition, several tools for improved post-processing and spectral and image visualization in both animal and human studies are provided. The post processing imaging unit 4660 is leveraged for the computationally intensive tasks of automatic deconvolution of each acquired optical spectrum, fluorescent particle reporters flow tracking and spatial texture based classifiers to decipher the tissue type and heterogeneity associated with each of the plurality of image pixels for visualization. The tracking of particle flow within tissues using one or more particle probes (i.e., multiplexing) is performed with post-processing motion-tracking algorithms to map the spatio-temporal distributions of acquired optical signals in a given region of interest. This information is further analyzed using spatial texture-based classifiers for disease staging and to assess the heterogeneity of particle distributions.

In some embodiments, graphically augmenting comprises superimposing on one or more video streams, or any multiplexed combination thereof, additional data (e.g., graphically rendering a combined video stream comprising medical text, retrieved from the Nanomed database, related to the subject of a particular video stream and one or more video streams). In certain embodiments, more than one additional data is superimposed onto a video stream and displayed on a monitor. Monitors may include traditional screens, as well as wearable displays, flexible displays, and/or other portable displays. In some embodiments, the additional data assists with the operation being performed by a practitioner (e.g., cutting guides in surgery, highlighting of important tissues or tissue barriers, etc.) In various embodiments, the additional data can comprise any one of text (i.e., particle type/composition, ligand, animal model, dose/volume of injectate, etc.), optical/PET imaging parameters (i.e., max pixel intensity, % ID/g, etc.), camera performance parameters (i.e., gain, exposure time, etc.), nodal fluorescence spectral signature (e.g., signal distribution, etc.), or histology (e.g., tumor burden, etc.).

Figure 47:
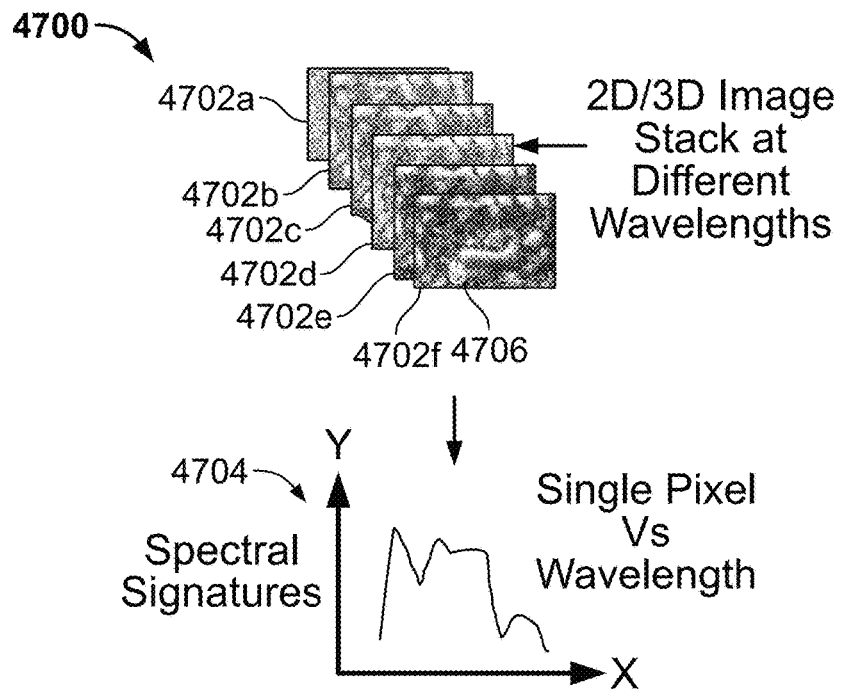
FIG. 47 depicts a graphical stack of multispectral images and illustrates corresponding spectral signature analysis, in accordance with an embodiment of the present disclosure.

FIG. 47 is an example of pixel-based wavelength analysis of a multichannel video stream. Video signals filtered to display only the wavelength corresponding to the fluorescent species administered are examined on a pixel-by-pixel basis. Due to the synchronicity of the video capture device, the pixel 4706 represents an exact 2D spatial position at each of the fluorescent wavelengths represented in images 4702*a*, 4702*b*, 4702*c*, 4702*d*, 4702*e* (collectively 4702). The spectral signature plot 4704 approximates the spectral intensity at each wavelength. In some embodiments, each of the one or more images 4702 is displayed in a "stack" on the display device and the practitioner is enabled to switch between them as desired.

Multispectral Deconvolution

In certain embodiments, fluorescent species produce an observable "shine-through" effect caused by leakage of the fluorescent agent to non-targeted tissues and fluids and nonlinearity in the signal changes. Additionally, various tissues exhibit different absorption and relaxation mechanisms, and as a consequence, the relationship between the fluorescent marker concentration and the visual signals differ between tissue types. Analyzing the contrast enhancement on a pixel-by-pixel basis using fluorescent marker weighted visual signals gives better appreciation of tissue heterogeneity, and the signal intensity obtained can be used to track a dose of fluorescent agent through the tissue and a concentration time curve for each pixel can be calculated. The tracking provides a primary assessment of tumors where the presence of increased enhancement may indicate areas of increased aggressiveness, enabling improved accuracy of tumor staging, improved detection of tumor recurrence, and enhanced ability to monitor and predict response to treatment. In a further embodiment, the amount of blood passing through a given region per unit time is defined as the blood flow rate. Assuming a linear relationship between a concentration time curve and the fluorescence relaxation rate and that proton density is not changed by uptake of the agent, the presence of the fluorescent agent reduces the relaxation rate at each time and is approximated from the pixel intensity as a linear function of relaxation rate and fluorescent agent concentration. Further, the temporal variation of fluorescent agent concentration after injection is estimated by comparing the post-injection intensity of the pixels at a particular moment in time and average pre-injection baseline signal intensity. For example, the passage of fluorescent agent through a given pixel of interest $C_{poi}(t)$ can be expressed as the convolution of the arterial input function (AIF) $C_a(t)$ with the residue function R(t), as follows:

$$C_{poi}(t) = \int_0^N C_a(t) R(t-a) da$$

where $C_{poi}(t)$ is the measured concentration in the tissue as a function of time, $C_a(t)$ is the fluorescent agent concentration in the artery as a function of time, R(t) is the amount of fluorescent agent still present in the vasculature at time t, and a is the fluorescent relaxivity.

For each imaging pixel, the tissue concentration time curve is deconvolved using, for example, the nonparametric single value decomposition (SVD) method, with AIF to calculate the residue function. The deconvolution is achieved by the SVD of an algebraic reformulation of the blood flow rate, and is compared with blood volume in the analyzed tissue region by calculating and integrating tissue densities in the region of interest. Such analysis enables the creation of parametric maps on a pixel-by-pixel based and is assisted by the increased signal-to-noise ratio enabled by the various embodiments of the present disclosure. For multiplexed fluorescence imaging detection studies, the algorithm is further modified to deconvolve spectral outputs at different wavelengths.

Figure 48:
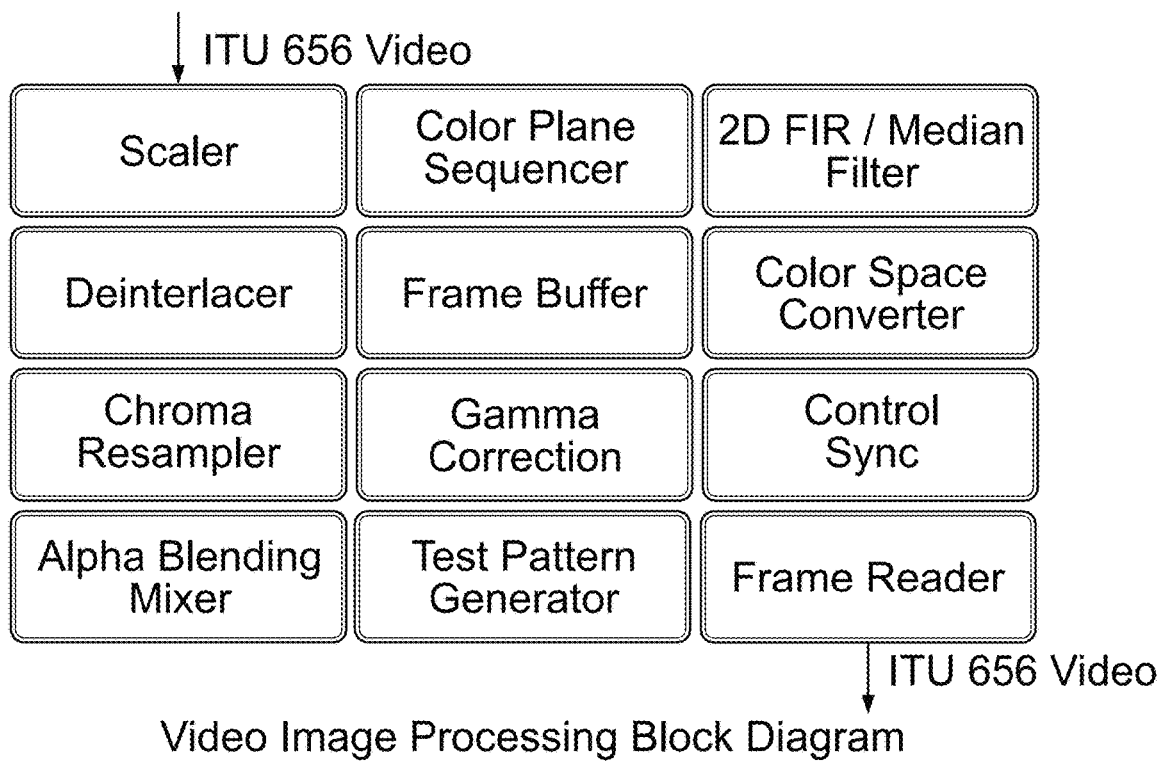
FIG. 48 is a block diagram representing a set of image processing operations performed on at least one channel of an ITU 656 video signal, in accordance with an embodiment of the present disclosure.

FIG. 48 is a block diagram of a video image processing sequence. ITU 656 video is processed using various image processing operations, including a scaler, color plane sequencer, 2D FIR/Median filter, deinterlacer, frame buffer, color space converter, chroma resampler, gamma correction, control synchronizer, alpha blending mixer, test pattern generator, and frame reader, for example. Processed ITU 656 is then directed to a display device, storage device, and/or additional processing elements.

Figure 49:
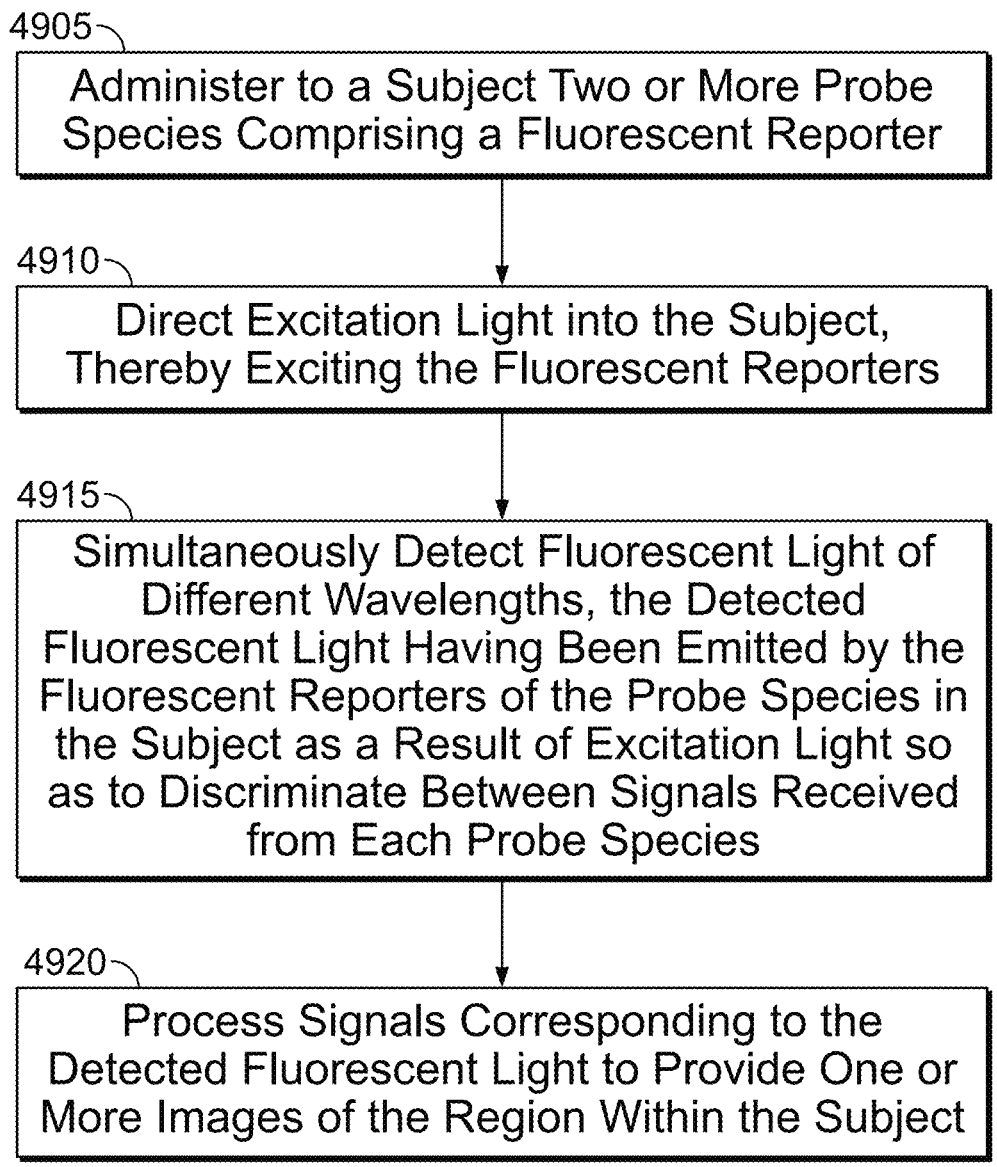
FIG. 49 depicts a flowchart demonstrating the steps for carrying out a method in accordance with an embodiment of the present disclosure.

In some embodiments, the method may operate as depicted in FIG. 49 in steps 4905, 4910, 4915, and 4920.

In some embodiments, the system is as depicted in FIG. 50. A light source in 5005 is configured to deliver multiple excitation wavelengths of light to excite a plurality of fluorescent reporters, thereby producing fluorescent light at two or more distinguishable wavelengths. A prism (5010) is configured to direct light received through a lens onto a plurality of spatially-separated detectors such that said detectors can receive, in real-time, different emitted signals simultaneously. A processor (5015) configured to process said signals corresponding to the detected fluorescent light at the two or more distinguishable wavelengths provide images of fluorescence within a subject.

Computing Environment

Figure 51:
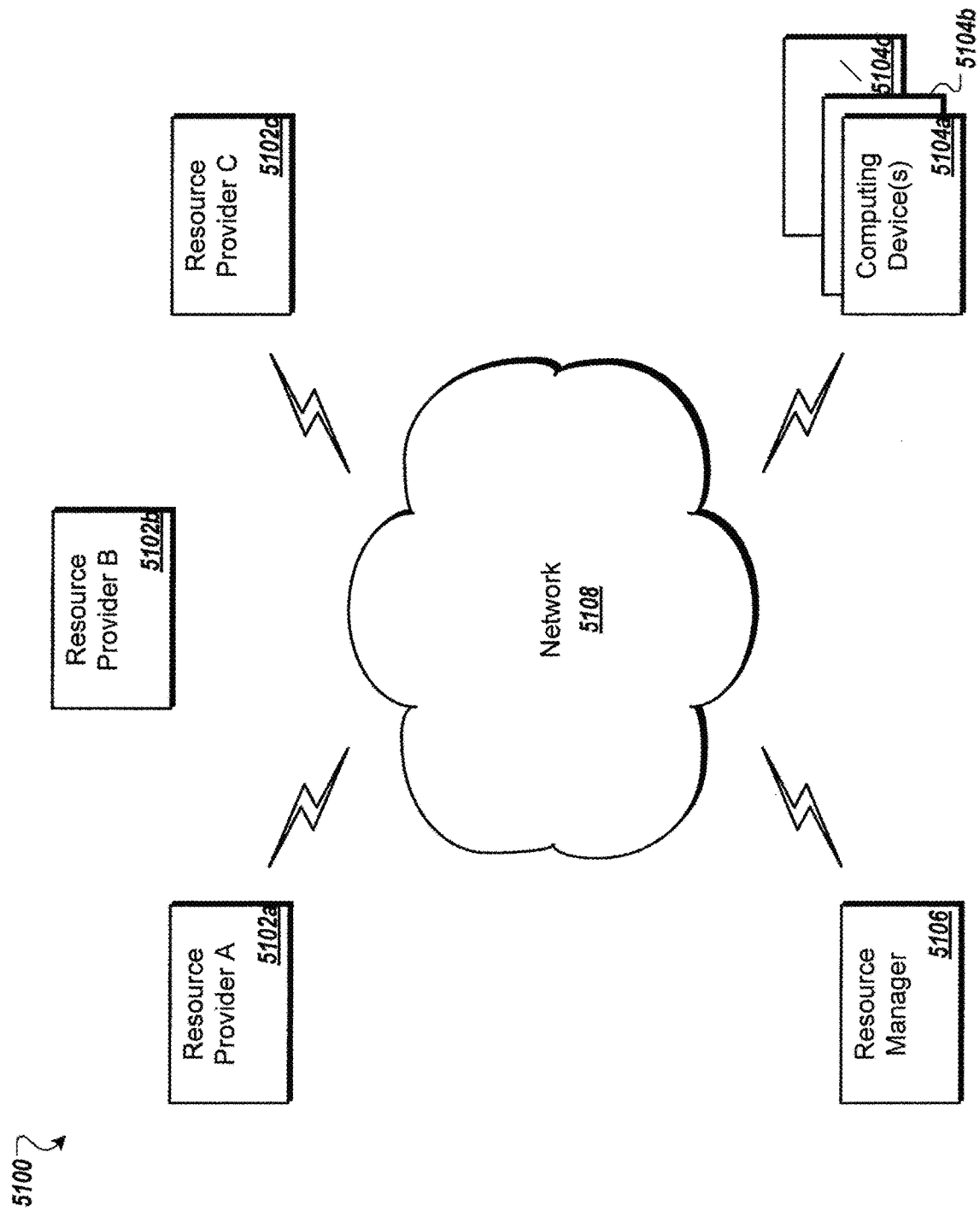
FIG. 51 is a block diagram of an example network environment for use in the methods and systems for analysis of multichannel image data, according to an illustrative embodiment.

FIG. 51 shows an illustrative network environment 5100 for use in the methods and systems for analysis of spectrometry data corresponding to particles of a sample, as described herein. In brief overview, referring now to FIG. 51, a block diagram of an exemplary cloud computing environment 5100 is shown and described. The cloud computing environment 5100 may include one or more resource providers 5102a, 5102b, 5102c (collectively, 5102). Each resource provider 5102 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 5102 may be connected to any other resource provider 5102 in the cloud computing environment 5100. In some implementations, the resource providers 5102 may be connected over a computer network 5108. Each resource provider 5102 may be connected to one or more computing device 5104a, 5104b, 5104c (collectively, 5104), over the computer network 5108.

The cloud computing environment 5100 may include a resource manager 5106. The resource manager 5106 may be connected to the resource providers 5102 and the computing devices 5104 over the computer network 5108. In some implementations, the resource manager 5106 may facilitate the provision of computing resources by one or more resource providers 5102 to one or more computing devices 5104. The resource manager 5106 may receive a request for a computing resource from a particular computing device 5104. The resource manager 5106 may identify one or more resource providers 5102 capable of providing the computing resource requested by the computing device 5104. The resource manager 5106 may select a resource provider 5102 to provide the computing resource. The resource manager 5106 may facilitate a connection between the resource provider 5102 and a particular computing device 5104. In some implementations, the resource manager 5106 may establish a connection between a particular resource provider 5102 and a particular computing device 5104. In some implementations, the resource manager 5106 may redirect a particular computing device 5104 to a particular resource provider 5102 with the requested computing resource.

Figure 52:
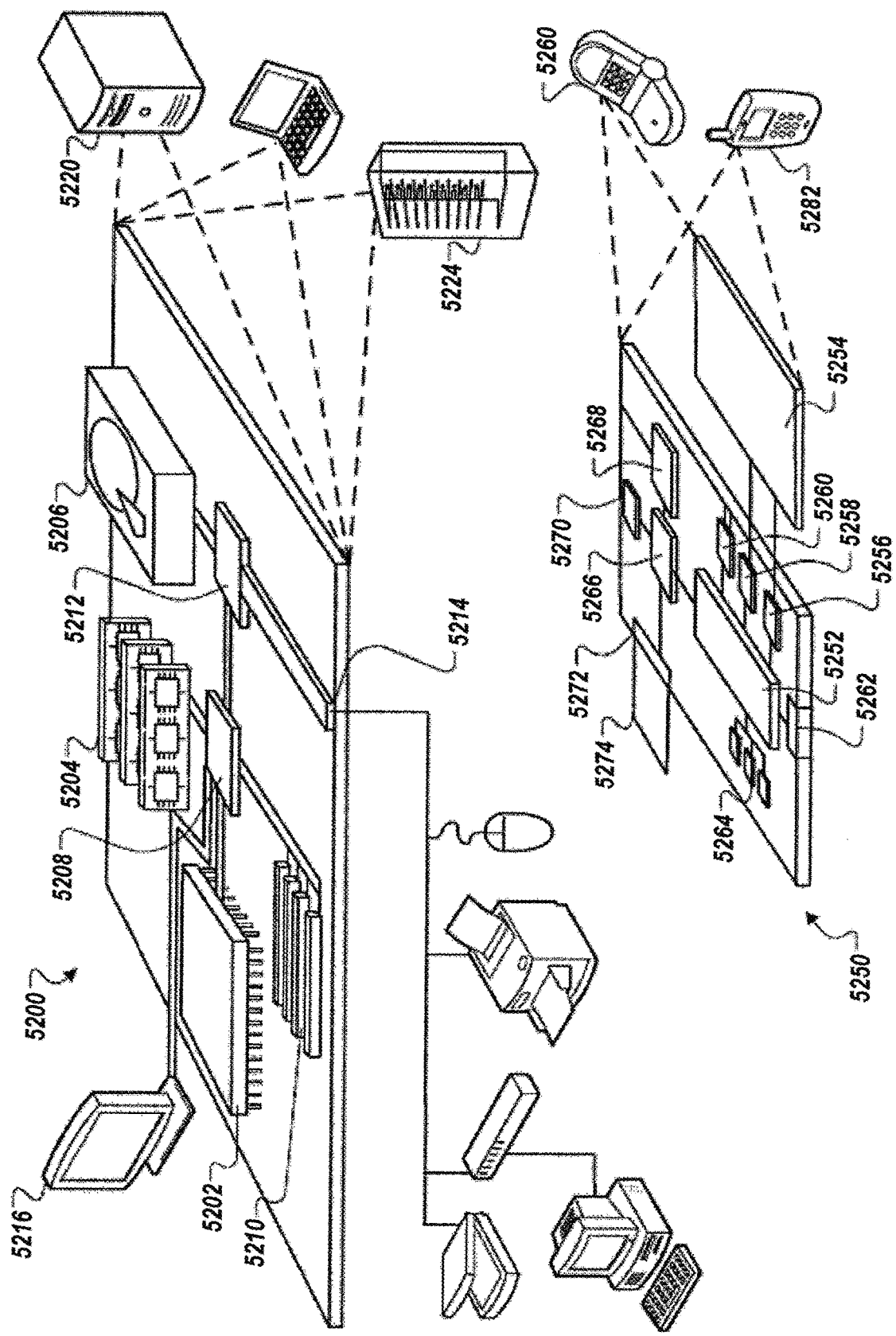
FIG. 52 is a block diagram of an example computing device and an example mobile computing device, for use in illustrative embodiments of the invention.

FIG. 52 shows an example of a computing device 5200 and a mobile computing device 5250 that can be used in the methods and systems described in this disclosure. The computing device 5200 is intended to represent various forms of digital computers, such as laptops, desktops, workstations, personal digital assistants, servers, blade servers, mainframes, and other appropriate computers. The mobile computing device 5250 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 5200 includes a processor 5202, a memory 5204, a storage device 5206, a high-speed interface 5208 connecting to the memory 5204 and multiple high-speed expansion ports 5210, and a low-speed interface 5212 connecting to a low-speed expansion port 5214 and the storage device 5206. Each of the processor 5202, the memory 5204, the storage device 5206, the high-speed interface 5208, the high-speed expansion ports 5210, and the low-speed interface 5212, are interconnected using various busses, and may be mounted on a common motherboard or in other manners as appropriate. The processor 5202 can process instructions for execution within the computing device 5200, including instructions stored in the memory 5204 or on the storage device 5206 to display graphical information for a GUI on an external input/output device, such as a display 5216 coupled to the high-speed interface 5208. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 5204 stores information within the computing device 5200. In some implementations, the memory 5204 is a volatile memory unit or units. In some implementations, the memory 5204 is a non-volatile memory unit or units. The memory 5204 may also be another form of computer-readable medium, such as a magnetic or optical disk.

The storage device 5206 is capable of providing mass storage for the computing device 5200. In some implementations, the storage device 5206 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 5202), perform one or more methods, such as those described above. The instructions can also be stored by one or more storage devices such as computer- or machine-readable mediums (for example, the memory 5204, the storage device 5206, or memory on the processor 5202).

The high-speed interface 5208 manages bandwidth-intensive operations for the computing device 5200, while the low-speed interface 5212 manages lower bandwidth-intensive operations. Such allocation of functions is an example only. In some implementations, the high-speed interface 5208 is coupled to the memory 5204, the display 5216 (e.g., through a graphics processor or accelerator), and to the high-speed expansion ports 5210, which may accept various expansion cards (not shown). In the implementation, the low-speed interface 5212 is coupled to the storage device 5206 and the low-speed expansion port 5214. The low-speed expansion port 5214, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 5200 may be implemented in a number of different forms, as shown in the figure. For example, it may be implemented as a standard server 5220, or multiple times in a group of such servers. In addition, it may be implemented in a personal computer such as a laptop computer 5222. It may also be implemented as part of a rack server system 5224. Alternatively, components from the computing device 5200 may be combined with other components in a mobile device (not shown), such as a mobile computing device 5250. Each of such devices may contain one or more of the computing device 5200 and the mobile computing device 5250, and an entire system may be made up of multiple computing devices communicating with each other.

The mobile computing device 5250 includes a processor 5252, a memory 5264, an input/output device such as a display 5254, a communication interface 5266, and a transceiver 5268, among other components. The mobile computing device 5250 may also be provided with a storage device, such as a micro-drive or other device, to provide additional storage. Each of the processor 5252, the memory 5264, the display 5254, the communication interface 5266, and the transceiver 5268, are interconnected using various buses, and several of the components may be mounted on a common motherboard or in other manners as appropriate.

The processor 5252 can execute instructions within the mobile computing device 5250, including instructions stored in the memory 5264. The processor 5252 may be implemented as a chipset of chips that include separate and multiple analog and digital processors. The processor 5252 may provide, for example, for coordination of the other components of the mobile computing device 5250, such as control of user interfaces, applications run by the mobile computing device 5250, and wireless communication by the mobile computing device 5250.

The processor 5252 may communicate with a user through a control interface 5258 and a display interface 5256 coupled to the display 5254. The display 5254 may be, for example, a TFT (Thin-Film-Transistor Liquid Crystal Display) display or an Oexcitation light (Organic Light Emitting Diode) display, or other appropriate display technology. The display interface 5256 may comprise appropriate circuitry for driving the display 5254 to present graphical and other information to a user. The control interface 5258 may receive commands from a user and convert them for submission to the processor 5252. In addition, an external interface 5262 may provide communication with the processor 5252, so as to enable near area communication of the mobile computing device 5250 with other devices. The external interface 5262 may provide, for example, for wired communication in some implementations, or for wireless communication in other implementations, and multiple interfaces may also be used.

The memory 5264 stores information within the mobile computing device 5250. The memory 5264 can be implemented as one or more of a computer-readable medium or media, a volatile memory unit or units, or a non-volatile memory unit or units. An expansion memory 5274 may also be provided and connected to the mobile computing device 5250 through an expansion interface 5272, which may include, for example, a SIMM (Single In Line Memory Module) card interface. The expansion memory 5274 may provide extra storage space for the mobile computing device 5250, or may also store applications or other information for the mobile computing device 5250. Specifically, the expansion memory 5274 may include instructions to carry out or supplement the processes described above, and may include secure information also. Thus, for example, the expansion memory 5274 may be provided as a security module for the mobile computing device 5250, and may be programmed with instructions that permit secure use of the mobile computing device 5250. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 5252), perform one or more methods, such as those described above. The instructions can also be stored by one or more storage devices, such as one or more computer- or machine-readable mediums (for example, the memory 5264, the expansion memory 5274, or memory on the processor 5252). In some implementations, the instructions can be received in a propagated signal, for example, over the transceiver 5268 or the external interface 5262.

The mobile computing device 5250 may communicate wirelessly through the communication interface 5266, which may include digital signal processing circuitry where necessary. The communication interface 5266 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 5268 using a radio-frequency. In addition, short-range communication may occur, such as using a Bluetooth®, Wi-Fi™, or other such transceiver (not shown). In addition, a GPS (Global Positioning System) receiver module 5270 may provide additional navigation- and location-related wireless data to the mobile computing device 5250, which may be used as appropriate by applications running on the mobile computing device 5250.

The mobile computing device 5250 may also communicate audibly using an audio codec 5260, which may receive spoken information from a user and convert it to usable digital information. The audio codec 5260 may likewise generate audible sound for a user, such as through a speaker, e.g., in a handset of the mobile computing device 5250. Such sound may include sound from voice telephone calls, may include recorded sound (e.g., voice messages, music files, etc.) and may also include sound generated by applications operating on the mobile computing device 5250.

The mobile computing device 5250 may be implemented in a number of different forms, as shown in the figure. For example, it may be implemented as a cellular telephone 5280. It may also be implemented as part of a smart-phone 5282, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Equivalents

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A portable imaging system, comprising a portable imaging apparatus and a plurality of different fluorescent reporters that produce fluorescent light at two or more distinguishable wavelengths, wherein:
   the portable imaging apparatus comprises:
      a light source configured to deliver multiple excitation wavelengths of light to excite the plurality of different fluorescent reporters that produce fluorescent light at two or more distinguishable wavelengths, wherein the light source is configured to deliver an even distribution of light via a plurality of emission points disposed in a planar configuration around a single axis optical lens;
      a prism configured to direct light received through a lens onto a plurality of spatially-separated detectors via at least three discrete optical pathways, such that said detectors can simultaneously measure, in real-time, different emitted fluorescent signals at the two or more distinguishable wavelengths; and
      a processor configured to process signals corresponding to the detected fluorescent light at the two or more distinguishable wavelengths to provide images of fluorescence of the plurality of different fluorescent reporters within a subject;
   and wherein each of the plurality of different fluorescent reporters comprises a silica nanoparticle.

2. The imaging system of claim 1, wherein the silica nanoparticle comprises from about 1 to about 20 ligands attached thereto.

3. The imaging system of claim 2, wherein the light source comprises two or more lasers and/or a light engine.

4. The imaging system of claim 2, wherein the portable imaging apparatus further comprises a multi-band filter positioned in front of the lens, wherein the multi-band filter is configured to block any excitation light coming from the light source, but will be transparent for all other light.

5. The imaging system of claim 2, wherein the portable imaging apparatus comprises narrow band filters each positioned between the prism and a respective detector.

6. The imaging system of claim 2, wherein the prism is a dichroic prism.

7. The imaging system of claim 2, wherein the prism comprises at least two surfaces each comprising a different coating.

8. The imaging system of claim 2, wherein the portable imaging apparatus further comprises:
   a first signal pre-conditioning module for performing a first set of image processing operations on a first signal of the plurality of signals, the first signal corresponding to a first unique reporter within the subject;
   a second signal pre-conditioning module for performing the first set of image processing operations on a second signal of the plurality of signals, the second signal corresponding to a second fluorescent reporter within the subject, wherein the first and second signal conditioning modules are configured to synchronously perform image processing on their respective signals;
   a third and/or subsequent signal pre-conditioning modules for performing the first set of image processing operations on a third and/or subsequent signal of the plurality of signals, each signal corresponding to a unique reporter; and
   a monitor for displaying the processed signals.

9. The imaging system of claim 8, wherein each of the first and second signal pre-conditioning modules and the third and/or subsequent signal pre-conditioning modules is a member selected from the group consisting of a field programmable gate array, an application-specific integrated circuit, and a central processing unit.

10. The imaging system of claim 8, wherein the first and second signal pre-conditioning modules and the third and/or subsequent signal pre-conditioning modules exist on a single physical device.

11. The imaging system of claim 8, wherein the first set of image processing operations comprises one or more members selected from the group consisting of fast Fourier transformation, discrete Fourier transformation, finite impulse response filtering, and infinite impulse response filtering.

12. The imaging system of claim 8, further comprising:
   a first signal post-conditioning module for performing a second set of image processing operations on the first signal;

a second signal post-conditioning module for performing the second set of image processing operations on the second signal, wherein the first and second signal post-conditioning modules are configured to synchronously perform image processing on their respective signals; and, a third and/or subsequent signal post-conditioning module for performing the second set of image processing operations on a third and/or subsequent signal of the plurality of signals, wherein the second set of image processing operations comprises one or more members selected from the group consisting of scaling, interlacing chroma resampling, alpha blend mixing, color plane sequencing, frame buffering, test pattern generation, 2D media filtering, color space conversion, control synchronization, and frame reading.

13. The imaging system of claim 12, wherein each of the first and second signal post-conditioning modules and the third and/or subsequent signal post-conditioning module(s) is a member selected from the group consisting of a field programmable gate array, an application-specific integrated circuit, and a central processing unit.

14. The imaging system of claim 12, wherein the first and second signal post-conditioning modules and the third and/or subsequent signal post-conditioning module(s) exist on a single board unit.

15. The imaging system of claim 8, further comprising a multiplexing module configured to multiplex the first signal and second signal.

16. The imaging system of claim 15, wherein the multiplexing module is additionally configured to multiplex the third and/or subsequent signals.

17. The imaging system of claim 15, comprising a processor configured to retrieve additional data from a medical imaging data repository and graphically render the additional data with the multiplexed signals, wherein the multiplexing module is additionally configured to superimpose and/or graphically augment the additional data with the multiplexed signals.

18. The imaging system of claim 1, wherein one of at least three discrete optical pathways comprises a RGB color channel.

19. The imaging system of claim 1, wherein two of the at least three discrete optical pathways comprises two or more dedicated channels for fluorophores.

20. The imaging system of claim 8, wherein the first and second signal pre-conditioning modules or the first and second post-conditioning modules are configured to perform the operations at the same time.

21. The imaging system of claim 20, wherein each signal comprises a video stream and wherein each frame of the video stream is processed by both the first and second signal post-conditioning device at the same time as each other, followed by the respective next video frames being processed at the same time as each other.

* * * * *